US010287546B2

(12) United States Patent
Chambers et al.

(10) Patent No.: US 10,287,546 B2
(45) Date of Patent: May 14, 2019

(54) KITS FOR NEURAL CONVERSION OF HUMAN EMBRYONIC STEM CELLS

(71) Applicant: MEMORIAL SLOAN-KETTERING CANCER CENTER, New York, NY (US)

(72) Inventors: Stuart Chambers, San Francisco, CA (US); Lorenz Studer, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 385 days.

(21) Appl. No.: 14/169,286

(22) Filed: Jan. 31, 2014

(65) Prior Publication Data
US 2017/0159012 A1 Jun. 8, 2017
US 2018/0362924 A9 Dec. 20, 2018

Related U.S. Application Data

(62) Division of application No. 13/201,137, filed as application No. PCT/US2010/024487 on Feb. 17, 2010, now Pat. No. 8,642,334.

(60) Provisional application No. 61/296,796, filed on Jan. 20, 2010, provisional application No. 61/207,763, filed on Feb. 17, 2009.

(51) Int. Cl.
C12N 5/0793 (2010.01)

(52) U.S. Cl.
CPC ........ C12N 5/0619 (2013.01); C12N 2501/41 (2013.01); C12N 2501/415 (2013.01); C12N 2501/60 (2013.01); C12N 2506/02 (2013.01)

(58) Field of Classification Search
None
See application file for complete search history.

(56) References Cited

U.S. PATENT DOCUMENTS

| | | | |
|---|---|---|---|
| 5,166,065 A | 11/1992 | Williams et al. |
| 5,340,740 A | 8/1994 | Petitte et al. |
| 5,453,357 A | 9/1995 | Hogan |
| 5,523,226 A | 6/1996 | Wheeler |
| 5,589,376 A | 12/1996 | Anderson et al. |
| 6,610,540 B1 | 8/2003 | Csete et al. |
| 6,787,356 B1 | 9/2004 | Studer et al. |
| 6,833,269 B2 | 12/2004 | Carpenter |
| 6,887,706 B2 | 5/2005 | Zhang et al. |
| 7,005,252 B1 | 2/2006 | Thomson |
| 7,011,828 B2 | 3/2006 | Reubinoff et al. |
| 7,112,437 B2 | 9/2006 | Pera |
| 7,211,434 B2 | 5/2007 | Van Der Ko et al. |
| 7,252,995 B2 | 8/2007 | Fu et al. |
| 7,294,510 B2 | 11/2007 | Okano et al. |
| 7,297,539 B2 | 11/2007 | Mandalam et al. |
| 7,332,336 B2 | 2/2008 | Ochiya et al. |
| 7,368,115 B2 | 5/2008 | Ohta et al. |
| 7,763,463 B2 | 7/2010 | Carpenter et al. |
| 7,892,830 B2 | 2/2011 | Bergendahl et al. |
| 8,153,422 B2 | 4/2012 | Isacson et al. |
| 8,153,428 B2 | 4/2012 | Carpenter et al. |
| 8,252,585 B2 | 8/2012 | Carpenter |
| 8,252,586 B2 | 8/2012 | Carpenter et al. |
| 8,323,971 B2 | 12/2012 | Pedersen et al. |
| 8,551,783 B2 | 10/2013 | Kim et al. |
| 8,642,334 B2 | 2/2014 | Chambers et al. |
| 8,883,502 B2 | 11/2014 | Zhang et al. |
| 8,932,857 B2 | 1/2015 | Yamanaka et al. |
| 9,249,389 B2 | 2/2016 | Isacson et al. |
| 9,453,198 B2 | 9/2016 | Studer et al. |
| 9,487,751 B2 | 11/2016 | Anderson et al. |
| 2003/0036195 A1 | 2/2003 | Studer et al. |
| 2003/0211605 A1 | 11/2003 | Lee et al. |
| 2004/0005704 A1 | 1/2004 | Csete et al. |
| 2004/0087478 A1 | 5/2004 | Gillen et al. |
| 2004/0214324 A1 | 10/2004 | Isacson et al. |
| 2005/0260747 A1 | 11/2005 | Reubinoff et al. |
| 2006/0078543 A1 | 4/2006 | Reubinoff et al. |
| 2007/0224650 A1 | 9/2007 | Jessell et al. |
| 2009/0035285 A1 | 2/2009 | Condie et al. |
| 2010/0009442 A1 | 1/2010 | Sasai et al. |
| 2010/0093090 A1 | 4/2010 | Deng et al. |
| 2010/0099772 A1 | 4/2010 | Bean et al. |
| 2011/0229441 A1 | 9/2011 | Benchoua et al. |
| 2012/0094381 A1 | 4/2012 | Chambers et al. |
| 2012/0142093 A1 | 6/2012 | Takahashi et al. |
| 2012/0148549 A1 | 6/2012 | Anderson et al. |
| 2012/0322146 A1 | 12/2012 | Carpenter et al. |
| 2013/0108669 A1 | 5/2013 | Cooper et al. |
| 2013/0183674 A1 | 7/2013 | Studer et al. |
| 2014/0199274 A1 | 7/2014 | Kim et al. |
| 2014/0248696 A1 | 9/2014 | Zhang et al. |
| 2014/0314721 A1 | 10/2014 | Semechkin et al. |
| 2015/0010514 A1 | 1/2015 | Studer et al. |
| 2015/0010515 A1 | 1/2015 | Schoeler et al. |
| 2015/0030570 A1 | 1/2015 | Pan et al. |

(Continued)

FOREIGN PATENT DOCUMENTS

| | | |
|---|---|---|
| CA | 2923592 A1 | 3/2015 |
| CN | 102191221 A | 9/2011 |

(Continued)

OTHER PUBLICATIONS

U.S. Appl. No. 13/697,274 (U.S. Pat. No. 9,453,198), filed Jan. 22, 2013 (Sep. 27, 2016).

(Continued)

Primary Examiner — Daniel C Gamett
(74) Attorney, Agent, or Firm — Baker Botts L.L.P.

(57) ABSTRACT

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. Specifically, methods are provided for obtaining neural tissue, floor plate cells, and placode including induction of neural plate development in hESCs for obtaining midbrain dopamine (DA) neurons, motorneurons, and sensory neurons. Further, neural plate tissue obtained using methods of the present inventions are contemplated for use in co-cultures with other tissues as inducers for shifting differentiation pathways, i.e. patterning.

31 Claims, 39 Drawing Sheets
Specification includes a Sequence Listing.

(56) References Cited

U.S. PATENT DOCUMENTS

| | | | |
|---|---|---|---|
| 2015/0086481 | A1 | 3/2015 | Ganat et al. |
| 2015/0087541 | A1 | 3/2015 | Gonzalez et al. |
| 2015/0265652 | A1 | 9/2015 | George et al. |
| 2015/0353888 | A1 | 12/2015 | Inoue et al. |
| 2016/0108362 | A1 | 4/2016 | Su et al. |
| 2016/0115444 | A1 | 4/2016 | Studer et al. |
| 2016/0115448 | A1 | 4/2016 | Studer et al. |
| 2016/0145582 | A1 | 5/2016 | Yu |
| 2016/0201032 | A1 | 7/2016 | Studer et al. |
| 2016/0326491 | A1 | 11/2016 | Chambers et al. |

FOREIGN PATENT DOCUMENTS

| | | |
|---|---|---|
| EP | 1 645 286 A1 | 4/2006 |
| KR | 101331034 B1 | 11/2013 |
| WO | WO 2003/000868 A1 | 1/2003 |
| WO | WO 2007/113505 A2 | 10/2007 |
| WO | WO 2008/018190 A1 | 2/2008 |
| WO | WO 2009/099152 A1 | 8/2009 |
| WO | WO 2010/063848 A1 | 6/2010 |
| WO | WO 2010/096496 A2 | 8/2010 |
| WO | WO 2010/141622 A2 | 12/2010 |
| WO | WO 2011/019092 A1 | 2/2011 |
| WO | WO 2011/108766 A1 | 9/2011 |
| WO | WO 2011/159726 A2 | 12/2011 |
| WO | WO 2015/054526 A2 | 4/2015 |
| WO | WO 2015/143622 A1 | 10/2015 |
| WO | WO 2016/063985 A1 | 4/2016 |
| WO | WO 2016/162747 A2 | 10/2016 |

OTHER PUBLICATIONS

U.S. Appl. No. 14/168,835 (US 2017/0130199), filed Jan. 30, 2014 (May 11, 2017).
U.S. Appl. No. 14/356,042 (US 2015/0010514), filed May 2, 2014 (Jan. 8, 2015).
U.S. Appl. No. 14/922,110 (US 2016/0115448), filed Oct. 23, 2015 (Apr. 28, 2016).
U.S. Appl. No. 15/077,012 (US 2016/0201032), filed Mar. 22, 2016 (Jul. 14, 2016).
U.S. Appl. No. 13/697,274, Aug. 19, 2016 Issue Fee Payment.
U.S. Appl. No. 13/697,274, May 20, 2016 Notice of Allowance.
U.S. Appl. No. 13/697,274, Apr. 7, 2016 Request for Continued Examination (RCE).
U.S. Appl. No. 13/697,274, Mar. 24 2016, Notice of Allowance.
U.S. Appl. No. 13/697,274, Mar. 24, 2016 Applicant Initiated Interview Summary.
U.S. Appl. No. 13/697,274, Mar. 22, 2016 Issue Fee Payment.
U.S. Appl. No. 13/697,274, Dec. 23, 2015 Notice of Allowance.
U.S. Appl. No. 13/697,274, Nov. 4, 2015 Response to Non-Final Office Action.
U.S. Appl. No. 13/697,274, May 5, 2015 Non-Final Office Action.
U.S. Appl. No. 13/697,274, Mar. 26, 2015 Response to Restriction Requirement.
U.S. Appl. No. 13/697,274, Dec. 26, 2014 Restriction Requirement.
U.S. Appl. No. 14/168,835, May 22, 2017 Non-Final Office Action.
U.S. Appl. No. 14/168,835, Jan. 27, 2017 Office of Petitions Decision.
U.S. Appl. No. 14/168,835, Sep. 15, 2016 Petition for review by the Office of Petitions.
U.S. Appl. No. 14/168,835, Mar. 15, 2016 Office of Petitions Decision.
U.S. Appl. No. 14/168,835, Nov. 26, 2014 Petition for review by the Office of Petitions.
U.S. Appl. No. 14/168,835, Sep. 30, 2014 Notice of Abandonment.
U.S. Appl. No. 14/356,042, May 12, 2017 Response to Non-Final Office Action.
U.S. Appl. No. 14/356,042, Feb. 22, 2017 Non-Final Office Action.
U.S. Appl. No. 14/356,042, Feb. 2, 2017 Amendment and Request for Continued Examination (RCE).
U.S. Appl. No. 14/356,042, Aug. 2, 2016 Final Office Action.
U.S. Appl. No. 14/356,042, Jul. 11, 2016 Response to Non-Final Office Action.
U.S. Appl. No. 14/356,042, Mar. 9, 2016 Non-Final Office Action.
U.S. Appl. No. 14/356,042, Feb. 8, 2016 Response to Restriction Requirement.
U.S. Appl. No. 14/356,042, Dec. 8, 2015 Restriction Requirement.
U.S. Appl. No. 15/077,012, Jun. 12, 2017 Non-Final Office Action.
"DAPI Nucleic Acid Stain," Molecular Probes, Invitrogen, Ltd. pp. 1-5 (2006).
Aoki, et al., "Sox1O Regulates the Development of Neural Crest-Derived Melanocytes in Xenopus," Developmental Biology, 259(1):19-33 (2003).
Bansal et al., "Specific Inhibitor of FGF Receptor Signaling: FGF-2-Mediated Effects on Proliferation, Differentiation, and MAPK Activation Are Inhibited by PD 173074 in Oligodendrocyte-Lineage Cells," Journal of Neuroscience, Research, 74(4):486-493 (2003).
Bennett et al., "Regulation of Wnt Signaling During Adipogenesis," J Biol Chem., 277(34):30998-31004 (2002).
Brivanlou and Darnell, "Signal Transduction and the Control of Gene Expression," Science, 295(5556):813-818 (2002).
Bystron et al., "The First Neurons of the Human Cerebral Cortex," Nat Neurosci., 9(7):880-886 (2006).
Cadigan and Liu, "Wnt Signaling: Complexity at the Surface," J Cell Sci., 119(Pt 3):395-402 (2006).
Chambers et al., "Combined small-molecule inhibition accelerates developmental timing and converts human pluripotent stem cells into nociceptors," Nature Biotechnology 30(7):715-720 (2012).
Chambers et al., "Dual-SMAD Inhibition/WNT Activation-Based Methods to Induce Neural Crest and Derivatives from Human Pluripotent Stem Cells," Methods in Molecular Biology (2013) DOI 10.1007/7651_2013_59.
Chen et al., "Immortalization and characterization of a nociceptive dorsal root ganglion sensory neuronal line," J Peripher Nery Syst., 12(2):121-130 (2007).
Cooper et al., "Differentiation of human ES and Parkinson's disease iPS cells into ventral midbrain dopaminergic neurons requires a high activity form of SHH, FGF8a and specific regionalization by retinoic acid", Molecular and Cellular Neurosciences, 45(3):258-266 (2010).
Crawford et al., "The Notch Response Inhibitor DAPT Enhances Neuronal Differentiation in Embryonic Stem Cell-Derived Embryoid Bodies Independently of Sonic Hedgehog Signaling," Developmental Dynamics, 236:886-892 (2007).
Cuny et al., "Structure-Activity Relationship Study of Bone Morphogenetic Protein (BMP) Signaling Inhibitors," Bioorg Med Chem Lett., 18(15):4388-4392 (2008).
Doble and Woodgett, "GSK-3: Tricks of the Trade for a Multi-Tasking Kinase," Journal of Cell Science, 116(7):1175-1186 (2003).
Dorsky et al., "Control of Neural Crest Cell Fate by the Wnt Signalling Pathway," Nature, 396(6709):370-373 (1998).
Dovey et al., "Functional Gamma-Secretase Inhibitors Reduce Beta-Amyloid Peptide Levels in Brain," J Neurochem., 76(1):173-181 (2001).
Ebendal et al., "Bone Morphogenetic Proteins and Their Receptors: Potential Functions in the Brain," Journal of Neuroscience, Research, 51(2):139-146 (1998).
Extended European Search Report dated Mar. 10, 2015 issued in European Patent Application No. 12846715.6.
Fang et al., "Electrophysiological Differences Between Nociceptive and Non-Nociceptive Dorsal Root Ganglion Neurones in the Rat in Vivo," The Journal of Physiology, 565(3):927-943 (2005).
George et al., "Nociceptive Sensory Neurons Derive From Contralaterally Migrating, Fate-Restricted Neural Crest Cells," Nat Neurosci., 10(10):1287-1293 (2007).
Gerdes et al., "Production of a Mouse Monoclonal Antibody Reactive With a Human Nuclear Antigen Associated With Cell Proliferation," Int J Cancer, 31(1):13-20 (1983).
Gerrero et al., "Bm-3.0: A POU-Domain Protein Expressed in the Sensory, Immune, and Endocrine Systems That Functions on Elements Distinct From Known Octamer Motifs," PNAS USA, 90(22):10841-10845 (1993).

(56) References Cited

OTHER PUBLICATIONS

Gordon et al., "Wnt Signaling. Multiple Pathways, Multiple Receptors, and Multiple Transcription Factors," The Journal of Biological Chemistry, 281(32):22429-22433 (2006).
Graves et al., "Derivation and Characterization of Putative Pluripotential Embryonic Stem Cells from Preimplantation Rabbit Embryos," Mol. Reprod and Dev., 36:424-433 (1993).
Hendzel et al., "Mitosis-Specific Phosphorylation of Histone H3 Initiates Primarily Within Pericentromeric Heterochromatin During G2 and Spreads in an Ordered Fashion Coincident With Mitotic Chromosome Condensation," Chromosoma., 106(6):348-360 (1997).
Hogan, "Bone Morphogenetic Proteins: Multifunctional Regulators of Vertebrate Development," Genes Dev., 10(13):1580-1594 (1996).
International Search Report dated Mar. 29, 2013 in International Patent Application No. PCT/US2012/063339.
International search report dated Sep. 26, 2014 in International Application No. PCT/US2014/035760.
ISR PCT/US2011/037179 dated Feb. 24, 2012.
Jin et al., "MAPK/ERK and Wnt/β-Catenin pathways are synergistically involved in proliferation of Sca-1 positive hepatic progenitor cells", Biochemical and Biophysical Research Communications 409:803-807 (2011).
Joannides et al., "Automated Mechanical Passaging: A Novel and Efficient Method for Human Embryonic Stem Cell Expansion," Stem Cells, 24(2):230-235 (2006).
Joksimovic et al., "Wnt antagonism of Shh facilitates midbrain floor plate neurogenesis," Developmental Biology, vol. 331, No. 2, Jul. 15, 2009, pp. 507-508.
Katoh et al., "Cross-talk of WNT and FGF Signaling Pathways at GSK3β to Regulate β-Catenin and SNAIL Signaling Cascades," Cancer Biology & Therapy, 5(9):1059-1064.
Kikuchi et al., "Multiplicity of the Interactions of Wnt Proteins and Their Receptors," Cell Signal, 19(4):659-671 (2007).
Kim et al., "Robust Enhancement of Neural Differentiation From Human ES and iPS Cells Regardless of Their Innate Difference in Differentiation Propensity," Stem Cell Reviews and Reports, 6(2):270-281 (2010).
Kirkeby et al., "Predictive Markers Guide Differentiation to Improve Graft Outcome in Clinical Translation of hESC Based Therapy for Parkinson's Disease," Cell Stem Cell, available online Oct. 27, 2016 (2016), downloaded Feb. 2, 2017 from <http://dx.doi.org/10.1016/j.stem.2016.09.004>.
Kitao et al., "Neurogenesis of Subpopulations of Rat Lumbar Dorsal Root Ganglion Neurons Including Neurons Projecting to the Dorsal Column Nuclei," The Journal of Comparative Neurology, 371(2):249-257 (1996).
Kodama et al., "Neurogenic Potential of Progenitors Derived from Human Circulating CD14+ Monocytes," Immunol. Cell Biol., 84(2):209-217 (2006).
Kriks S. et al., "Dopamine neurons derived from human ES cells efficiently engraft in animal models of Parkinson's disease," Nature, 480(7378):547-551 (2011).
Lee et al., "Instructive Role of Wnt/B-Catenin in Sensory Fate Specification in Neural Crest Stem Cells," Science, 303(5660): 1020-1023 (2004).
Lee et al., "The Expression and Posttranslational Modification of a Neuron-Specific B-Tubulin Isotype During Chick Embryo genesis," Cell Motility and the Cytoskeleton, 17(2):118-132 (1990).
Letinic et al., "Origin of GABAergic neurons in the human neocortex," Nature, 2002, vol. 417, No. 6889, pp. 645-649.
Li et al., "Rapid induction and long-term self-renewal of primitive neural precursors from human embryonic stem cells by small molecule inhibitors," PNAS 108(20):8299-8304 (2011).
Lin et al., "Foxa1 and Foxa2 function both upstream of and cooperatively with Lmx1a and Lmx1b in a feedforward loop promoting mesodiencephalic dopaminergic neuron development," Genome & Development Control, Developmental Biology 333:386-396 (2009).
Ma et al., "Neurogenin1 and Neurogenin2 Control Two Distinct Waves of Neurogenesis in Developing Dorsal Root Ganglia," Genes Dev., 13(13):1717-1728 (1999).
MacDonald et al., "Wnt/β-catenin signaling components, mechanisms, and diseases," Developmental Cell, 17(1):9-26 (2009).
Marmigere and Ernfors, "Specification and Connectivity of Neuronal Subtypes in the Sensory Lineage," Nat Rev Neurosci., 8(2):114-127 (2007).
Maroof et al., "Directed differentiation and functional maturation of cortical interneurons from human embryonic stem cells", Cell Stem Cell, Epub. May 2, 2013, vol. 12, No. 5, pp. 559-572.
Mehler et al., "Bone Morphogenetic Proteins in the Nervous System," Trends Neurosci., 20(7):309-317 (1997).
Menendez et al., "Wnt signaling and a Smad pathway blockade direct the differentiation of human pluripotent stem cells to multi potent neural crest cells," PNAS, 2011, vol. 108, No. 48, pp. 19240-19245.
Papapetrou et al., "Stoichiometric and Temporal Requirements of Oct4, Sox2, Klf4, and c-Myc Expression for Efficient Human Ipsc Induction and Differentiation," PNAS USA, 106(31):12759-12764 (2009).
Paterson et al., "Preclinical Studies of Fibroblast Growth Factor Receptor 3 As a Therapeutic Target in Multiple Myeloma," Br. J. Haematol., 124(5):595-603 (2004).
Raymon et al., "Immortalized Human Dorsal Root Ganglion Cells Differentiate into Neurons with Nociceptive Properties," J. Neurosci. 19(13):5420-5428 (1999).
Saha et al., "Technical Challenges in Using Human Induced Pluripotent Stem Cells to Model Disease," Cell Stem Cell, 5(6):584-595 (2009).
Schlosser et al., "Development of Neurogenic Placodes in *Xenopus laevis*," The Journal of Comparative Neurology, 418:121-146 (2000).
Schlosser et al., "Induction and Specification of Cranial Placodes," Dev Biol., 294(2):303-351 (2006) A: pp. 303-327.
Schlosser et al., "Induction and Specification of Cranial Placodes," Dev Biol., 294(2):303-351 (2006) B: pp. 328-351.
Steinbeck et al., "Optogenetics enables functional analysis of human embryonic stem cell-derived grafts in a Parkinson's disease model," Nature Biotechnology, 33(2):204-209 (2015).
Stem Cells: Scientific Progress and Future Research Directions. Department of Health and Human Services. Jun. 2001. Chapter 4. pp. 23-42.
Sun et al., "A Central Role for Islet1 in Sensory Neuron Development Linking Sensory and Spinal Gene Regulatory Programs," Nat Neurosci., 11(11): 1283-1293 (2008).
Sun et al., "Design, Synthesis, and Evaluations of Substituted 3-[(3- or 4-Carboxyethylpyrrol-2-yl)Methylidenyl]indolin-2-ones as Inhibitors of VEGF, FGF, and PDGF Receptor Tyrosine Kinases," J Med Chem., 42(25):5120-5130 (1999).
Takahashi et al., "Induction of Pluripotent Stem Cells From Mouse Embryonic and Adult Fibroblast Cultures by Defined Factors," Cell, 126(4):663-676 (2006).
Tanaka et al., "FGF-Induced Vesicular Release of Sonic Hedgehog and Retinoic Acid in Leftward Nodal Flow Is Critical for Left-Right Determination," Nature, 435(7039):172-177 (2005).
Theos et al., "The Silver Locus Product Pmell 7/Gp100/Silv/Me20: Controversial in Name and in Function," Pigment Cell Res., 18(5):322-336 (2005).
Thomson et al., "Isolation of a primate embryonic stem cell line," PNAS, 92:7844-7848 (1995).
Vierbuchen et al., "Direct Conversion of Fibroblasts to Functional Neurons by Defined Factors," Nature, 463 (7284): 1035-1041 (2010).
Wang et al., "Stem Cells from Human-Exfoliated Deciduous Teeth Can Differentiate into Dopaminergic Neuron-Like Cells," Stem Cells and Development, 19(9): 1375-1383 (2010).
Willert et al., "Wnt Proteins," CSH Perspectives in Biology, 4:1-13 (2012).
Woolf and Ma, "Nociceptors—Noxious Stimulus Detectors," Neuron, 55(3):353-364 (2007).
Written Opinion of the International Searching Authority dated Mar. 29, 2013 in International Patent Application No. PCT/US2012/063339.

(56) References Cited

OTHER PUBLICATIONS

Yamashita et al., "Bone Morphogenetic Protein Receptors," Bone, 19(6):569-574 (1996).
Yan et al., "Directed Differentiation of Dopaminergic Neuronal Subtypes from Human Embryonic Stem Cells," Stem Cells, 23(6):781-790 (2005).
Yu et al., "BMP type I receptor inhibition reduces heterotopic ossification," Nature Medicine 14(12):1363-1369 (2008).
Zhang and Zhang, "Differentiation of Neural Precursors and Dopaminergic Neurons from Human Embryonic Stem Cells," Methods Mal Biol., 584:355-366 (2010).
Zhou et al., "High-Efficiency Induction of Neural Conversion in Human ESCs and Human Induced Pluripotent Stem Cells With a Single Chemical Inhibitor of Transforming Growth Factor Beta Superfamily Receptors," Stem Cells, 28(10):1741-1750 (2010).
Zhu et al., "Functional Smoothened Is Required for Expression of Gli3 in Colorectal Carcinoma Cells," Cancer Letters, 207(2):205-214 (2004).
Zietlow et al., "The Survival of Neural Precursor Cell Grafts Is Influenced by In Vitro Expansion," Journal of Anatomy, 207(3):227-240 (2005).
U.S. Appl. No. 13/201,137 (U.S. Pat. No. 8,642,334), filed Nov. 10, 2011 (Feb. 4, 2014).
U.S. Appl. No. 13/201,137, Dec. 23, 2013 Issue Fee Payment.
U.S. Appl. No. 13/201,137, Sep. 24, 2013 Notice of Allowance.
U.S. Appl. No. 13/201,137, Sep. 17, 2013 Response after Final Action.
U.S. Appl. No. 13/201,137, Jul. 24, 2013 Final Office Action.
U.S. Appl. No. 13/201,137, Jun. 6, 2013 Response to Non-Final Office Action.
U.S. Appl. No. 13/201,137, Mar. 7, 2013 Non-Final Office Action.
U.S. Appl. No. 13/201,137, Jan. 24, 2013 Response to Restriction Requirement.
U.S. Appl. No. 13/201,137, Jan. 3, 2013 Restriction Requirement.
Agarwal et al., "Efficient Differentiation of Functional Hepatocytes from Human Embryonic Stem Cells," Stem Cells, 26:1117-1127 (2008).
Bailey et al., "Sensory Organs: Making and Breaking the Pre-Placodal Region," Current Topics in Developmental Biology, 72:167-204 (2006).
Baker et al., "Establishing neuronal identity in vertebrate neurogenic placodes," Development, 127:3045-3056 (2000).
Baker et al., "Vertebrate cranial placodes I. Embryonic induction," Dev Biol., 232(1):1-61, pp. 1-30 (2001a).
Baker et al., "Vertebrate cranial placodes I. Embryonic induction," Dev Biol., 232(1):1-61, pp. 31-61(2001b).
Barberi et al., "Derivation of engraftable skeletal myoblasts from human embryonic stem cells," Nat Med, 13(5):642-648 (2007).
Barberi et al., "Derivation of Multipotent Mesenchymal Precursors from Human Embryonic Stem Cells," PLoS Med, 2(6):e161 (2005).
Barberi et al., "Neural subtype specification of fertilization and nuclear transfer embryonic stem cells and application in parkinsonian mice," Nat Biotechnol. 10:1200-1207 (2003).
Bhattacharyya et al., "Hierarchy of regulatory events in sensory placode development," Curr Opin Genet Dev. 14(5):520-6 (2004).
Bouwmeester et al., "Cerberus is a head-inducing secreted factor expressed in the anterior endoderm of Spemann's organizer," Nature, 382:595-601 (1996).
Bradley et al., "Formation of germ-line chimaeras from embryo-derived teratocarcinoma cell lines," Nature 309:255-256 (1984).
Briscoe and Ericson, "The specification of neuronal identity by graded Sonic Hedgehog signalling," Semin Cell Dev Biol. 3:353-62 (1999).
Callaerts et al., "PAX-6 in Development and Evolution," Annu. Rev. Neurosci. 20:483-532 (1997).
Chambers et al., "Highly efficient neural conversion of human ES and iPS cells by dual inhibition of SMAD signaling," Nat Biotechnol., 27(3):275-280 (2009).
Chambers, et al., "Highly efficient neural conversion of human ES and iPS cells by dual inhibition of SMAD signaling," Nat Biotechnol, Corrigendum: in Nature Biotechnology 27(5):485.
Charrier et al., "Dual origin of the floor plate in the avian embryo," Development 129:4785-4796 (2002).
Charron et al., "The Morphogen Sonic Hedgehog Is an Axonal Chemoattractant that Collaborates with Netrin-1 in Midline Axon Guidance," Cell 113:11-23 (2003).
D'Amour et al., "Efficient differentiation of human embryonic stem cells to definitive endoderm," Nat Biotechnol, 23(12):1534-1541 (2005).
Dennis et al., "DAVID: Database for Annotation, Visualization, and Integrated Discovery," Genome Biology 4:R60 (2003).
Dezawa et al., "Potential of Bone Marrow Stromal Cells in Applications for Neuro-Degenerative, Neuro-Traumatic and Muscle Degenerative Diseases," Current Neuropharmacology, 3:257-266 (2005).
Doetschman et al. "Establishment of Hamster Blastocyst-Derived Embryonic Stem (ES) Cells," Dev Biol., 127:224-227 (1988).
Eiraku et al., "Self-organized formation of polarized cortical tissues from ESCs and its active manipulation by extrinsic signals," Cell Stem Cell, 3:519-53 (2008).
Elkabetz et al., "Human ES cell-derived neural rosettes reveal a functionally distinct early neural stem cell stage," Genes Dev., 22:152-165 Erratum (2008).
Elkabetz et al., "Human ES Cell-Derived Neural Rosettes Reveal a Functionally Distinct Early Neural Stem Cell Stage," Genes Dev., 22(2):152-165 (2008).
Erceg et al., "Human Embryonic Stem Cell Differentiation Toward Regional Specific Neural Precursors," Stem Cells, 27:78-87 (2009).
Ericson et al., "Two Critical Periods of Sonic Hedgehog Signaling Required for the Specification of Motor Neuron Identity," Cell, 87:661-673 (1996).
Evans et al., "Derivation and preliminary characterization of pluripotent cell lines from porcine and bovine blastocysts," Theriogenology, 33(1):125-128 (1990).
Evans et al., "Establishment in culture of pluripotential cells from mouse embryos," Nature, 292:154-156 (1981).
Fasano et al., "shRNA knockdown of Bmi-1 reveals a critical role for p21-Rb pathway in NSC self-renewal during development," Cell Stem Cell, 1:87-99 (2007).
Fasano et al., "Bmi-1 cooperates with Foxgl to maintain neural stem cell self-renewal in the fore brain," Genes Dev., 23:561-574 (2009).
Fasano et al., "Bmi-1 cooperates with Foxgl to maintain neural stem cell self-renewal in the fore brain," Genes Dev., 23:561-574 Suppl. Fig. 1 (2009).
Fasano et al., "Bmi-1 cooperates with Foxgl to maintain neural stem cell self-renewal in the fore brain," Genes Dev., 23:561-574 Suppl. Fig. 2 (2009).
Fasano et al., "Bmi-1 cooperates with Foxgl to maintain neural stem cell self-renewal in the fore brain," Genes Dev., 23:561-574 Suppl. Fig. 3 (2009).
Fasano et al., "Bmi-1 cooperates with Foxgl to maintain neural stem cell self-renewal in the fore brain," Genes Dev., 23:561-574 Suppl. Fig. 4 (2009).
Fasano et al., "Bmi-1 cooperates with Foxgl to maintain neural stem cell self-renewal in the fore brain," Genes Dev., 23:561-574 Suppl. Fig. legends (2009).
Fasano et al., "Bmi-1 cooperates with Foxgl to maintain neural stem cell self-renewal in the fore brain," Genes Dev., 23:561-574 Suppl. Materials (2009).
Fasano et al., "Efficient Derivation of Functional Floor Plate Tissue from Human Embryonic Stem Cells," Cell Stem Cell, 6(4):336-347 (2010).
Giles et al., "Pluripotency of Cultured Rabbit Inner Cell Mass Cells Detected by Isozyme Analysis and Eye Pigmentation of Fetuses Following Injection into Blastocysts or Morulae," Mol. Reprod and Dev., 36:130-138 (1993).
Glinka et al., "Dickkopf-1 is a member of a new family of secreted proteins and functions in head induction," Nature, 391:357-362 (1998).
Grappe et al., "Structural basis of BMP signalling inhibition by the cystine knot protein Noggin," Nature, 420:636-642 (2002).

(56) References Cited

OTHER PUBLICATIONS

Hemmati-Brivanlou et al., "Follistatin, an Antagonist of Activin, is Expressed in the Spemann Organizer and Displays Direct Neuralizing Activity," Cell, 77:283-295 (1994).
Huang et al., "Bioinformatics enrichment tools: paths toward the comprehensive functional analysis of large gene lists," Nucleic Acids Res., 37(1):1-13 (2009).
Huang et al., "Systematic and integrative analysis of large gene lists using DAVID Bioinformatics Resources," Nat Protoc., 4(1):44-57 (2009).
Hunter et al., "Retinoic acid stimulates neurite outgrowth in the amphibian spinal cord," PNAS USA, 88:3666-3670 (1991).
Iannaccone et al., "Pluripotent Embryonic Stem Cells from the Rat Are Capable of Producing Chimeras," Dev. Biol. 163:288-292 (1994).
International Search Report dated Nov. 11, 2010 in International Patent Application No. PCT/US10/024487.
Ivanova et al., "Dissecting self-renewal in stem cells with RNA interference," Nature, 442:533-538 (2006).
Jessell et al., "Polarity and patterning in the neural tube: the origin and function of the floor plate," Ciba Found Symp., 144:255-276, pp. 255-266 (1989a).
Jessell et al., "Polarity and patterning in the neural tube: the origin and function of the floor plate," CibaFound Symp., 144:255-276, pp. 267-276 (1989b).
Jessell et al., Polarity and patterning in the neural tube: the origin and function of the floor plate. Ciba Found Symp., (discussion) 144:276-280, 290-295 (1989).
Jessell, "Neuronal specification in the spinal cord: inductive signals and transcriptional codes," Nat Rev Genet., 1:20-29 (2000).
Jeong et al., "Distinct regulators of SHH transcription in the floor plate and notochord indicate separate origins for these tissues in the mouse node," Development, 130:3891-3902 (2003).
Jeong et al., "A functional screen for sonic hedgehog regulatory elements across a 1 Mb interval identifies long-range ventral forebrain enhancers," Development, 133:7761-7772 (2005).
Joksimovic et al., "Wnt antagonism of SHH facilitates midbrain floor plate neurogenesis," Nat Neurosci., 12:125-131 (2009).
Kakegawa et al, International Association for Dental Research, General Session and Exhibition, Jun. 28-Jul. 1, Abstract #0267, Brisbane Australia.
Kawasaki et al., "Induction of Midbrain Dopaminergic Neurons from ES Cells by Stromal Cell-Derived Inducing Activity," Neuron, 28:31-40 (2000).
Kim et al., "Oct4-Induced Pluripotency in Adult Neural Stem Cells," Cell, 136:411-419 (2009).
Kimura-Yoshida et al., "Crucial roles of Foxa2 in mouse anterior-posterior axis polarization via regulation of anterior visceral endoderm-specific genes," PNAS, 104:5919-59249 with Data Supplement Figs. Legends SFig. 5 and SFig. 6 (2006).
Kittappa et al, "The foxa2 Gene Controls the Birth and Spontaneous Degeneration of Dopamine Neurons in Old Age," PLoS Biol., 5(12):e325 (2007).
Laflamme et al., "Cardiomyocytes derived from human embryonic stem cells in pro-survival factors enhance function of infarcted rat hearts," Nat Biotechnol., 25(9):1015-1024 (2007).
Lee et al., "Directed Differentiation and Transplantation of Human Embryonic Stem Cell-Derived Motoneurons," Stem Cells, 25:1931-1939 (2007).
Lee et al., "Isolation and Directed Differentiation of Neural Crest Stem Cells Derived From Human Embryonic Stem Cells," Nat Biotechnol., 25(12):1468-1475 (2007).
Lee et al., "Modeling Pathogenesis and Treatment of Familial Dysautonomia using Patient-Specific iPSCs," Nature, 461(7262):402-406 (2009).
Li et al., "Specification of Motoneurons From Human Embryonic Stem Cells," Nat Biotechnol., 23(2):215-221 (2005).
Li et al., "Directed differentiation of ventral spinal progenitors and motor neurons from human embryonic stem cells by small molecules," Stem Cells, 4:886-893 (2008).
Lois et al., "Germline Transmission and Tissue-Specific Expression of Transgenes Delivered by Lentiviral Vectors," Science, 295:868-872 (2002).
Lyuksyutova et al., "Anterior-Posterior Guidance of Commissural Axons by Wnt-Frizzled Signaling," Science, 302:1984-1988 (2003).
Martin, "Isolation of a pluripotent cell line from early mouse embryos cultured in medium conditioned by teratocarcinoma stem cells," PNAS USA, 78(12):7634-7638 (1981).
Matise et al., "Gli2 is required for induction of floor plate and adjacent cells, but not most ventral neurons in the mouse central nervous system," Development, 125:2759-2770 (1998).
Mizuseki et al., "Generation of neural crest-derived peripheral neurons and floor plate cells from mouse and primate embryonic stem cells," PNAS USA, 100:5828-5833 (2003).
Mizuseki et al., "Generation of neural crest-derived peripheral neurons and floor plate cells from mouse and primate embryonic stem cells," PNAS USA, 100:5828-5833 Supporting Information List (2003).
Mizuseki et al., "Generation of neural crest-derived peripheral neurons and floor plate cells from mouse and primate embryonic stem cells," PNAS USA, 100:5828-5833 Supporting Materials and Methods (2003).
Mizuseki et al., "Generation of neural crest-derived peripheral neurons and floor plate cells from mouse and primate embryonic stem cells," PNAS USA, 100:5828-5833 Supporting Information Fig. 6 (2003).
Mizuseki et al., "Generation of neural crest-derived peripheral neurons and floor plate cells from mouse and primate embryonic stem cells," PNAS USA, 100:5828-5833 Supporting Fig. 6 (2003).
Mizuseki et al., "Generation of neural crest-derived peripheral neurons and floor plate cells from mouse and primate embryonic stem cells," PNAS USA, 100:5828-5833 Supporting Information Fig. 7 (2003).
Mizuseki et al., "Generation of neural crest-derived peripheral neurons and floor plate cells from mouse and primate embryonic stem cells," PNAS USA, 100:5828-5833 Supporting Fig. 7 (2003).
Mizuseki et al., "Generation of neural crest-derived peripheral neurons and floor plate cells from mouse and primate embryonic stem cells," PNAS USA, 100:5828-5833 Supporting Information Fig. 8 (2003).
Mizuseki et al., "Generation of neural crest-derived peripheral neurons and floor plate cells from mouse and primate embryonic stem cells," PNAS USA, 100:5828-5833 Supporting Fig. 8 (2003).
Mizuseki et al., "Generation of neural crest-derived peripheral neurons and floor plate cells from mouse and primate embryonic stem cells," PNAS USA, 100:5828-5833 Supporting Information Fig. 9 (2003).
Mizuseki et al., "Generation of neural crest-derived peripheral neurons and floor plate cells from mouse and primate embryonic stem cells," PNAS USA, 100:5828-5833 Supporting Fig. 9 (2003).
Mukhopadhyay et al., "Dickkopf1 is required for embryonic head induction and limb morphogenesis in the mouse," Dev Cell, 3:423-434 (2001).
Mullor et al., "Pathways and consequences: Hedgehog signaling in human disease," Trends Cell Biol 12:562-569 (2002).
Munoz-Sanjuan et al., "Neural Induction, The Default Model and Embryonic Stem Cells," Nat Rev Neurosci., 3:271-280 (2002).
Notarianni et al., "Maintenance and differentiation in culture of pluripotential embryonic cell lines from pig blastocysts," J. Reprod. Fert. Suppl., 41:51-56 (1990).
Ono et al., "Differences in neurogenic potential in floor plate cells along an anteroposterior location: midbrain dopaminergic neurons originate from mesencephalic floor plate cells," Development, 134:3213-3225 (2007).
Ono et al., "Differences in neurogenic potential in floor plate cells along an anteroposterior location: midbrain dopaminergic neurons originate from mesencephalic floor plate cells," Development, 134:3213-3225 Data Supplement (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 1 (2007).

(56) References Cited

OTHER PUBLICATIONS

Ono et al., "Differences in neurogenic potential in floor plate cells along an anteroposterior location: midbrain dopaminergic neurons originate from mesencephalic floor plate cells," Development, 134:3213-3225 Supplemental Fig. 2 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 3 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 4 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 5 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 6 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 7 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 8 (2007).
Patten et al., "Distinct modes of floor plate induction in the chick embryo," Development, 130:4809-4821 (2003).
Perrier et al., "Derivation of midbrain dopamine neurons from human embryonic stem cells," PNAS USA, 101:12543-12548 (2004).
Perrier et al., "Derivation of midbrain dopamine neurons from human embryonic stem cells," PNAS USA, 101:12543-12548 Supporting Materials, Methods, Supplemental Data, and Supporting Fig. 6 (2004).
Placantonakis et al., "BAC Transgenesis in Human Embryonic Stem Cells as a Novel Tool to Define the Human Neural Lineage," Stem Cells 27:521-532 (2009).
Placzek and Briscoe, "The Floor Plate: Multiple Cells, Multiple Signals," Nat. Rev. Neurosci., 6:230-240 (2005).
Placzek et al., "Induction of floor plate differentiation by contact-dependent, homeogenetic signals," Development, 117:205-218 (1993).
Placzek, "The role of the notochord and floor plate in inductive interactions," Curr Opin Genet Dev., 5:499-506 (1995).
Reubinoff et al., "Neural progenitors from human embryonic stem cells," Nature Biotechnology, 19:1134-1140 (2001).
Roelink et al., "Floor plate and motor neuron induction by vhh-1, a vertebrate homolog of hedgehog expressed by the notochord," Cell, 76:761-775 (1994).
Sasai et al., "Xenopus chordin: a Novel Dorsalizing Factor Activated by Organizer-Specific Homeobox Genes," Cell, 79(5):779-790 (1994).
Shen et al., "The timing of cortical neurogenesis is encoded within lineages of individual progenitor cells," Nat Neurosci., 9:743-751 (2006).
Shirasaki et al., "Guidance of cerebellofugal axons in the rat embryo: directed growth toward the floor plate and subsequent elongation along the longitudinal axis," Neuron, 14:961-972 (1995).
Smith et al., "Expression Cloning of noggin, a New Dorsalizing Factor Localized to the Spemann organizer in Xenopus Embryos," Cell, 70:829-840 (1992).
Smith et al., "Inhibition of Activin/Nodal signaling promotes specification of human embryonic stem cells into neuroectoderm," Dev Biol., 313:107-117 (2008).
Streit, "Early development of the cranial sensory nervous system: from a common field to individual placodes," Dev Biol., 276:1-15 (2004).

Sukoyan et al., "Embryonic Stem Cells Derived from Morulae, Inner Cell Mass, and Blastocysts of Mink Comparisons of Their Pluripotencies," Mol. Reprod. Dev., 36:148-158 (1993).
Sukoyan et al., "Isolation and Cultivation of Blastocyst-Derived Stem Cell Lines from American Mink (*Mustela vison*)," Mol. Reprod. Dev., 33:418-431 (1992).
Sumi et al., "Defining early lineage specification of human embryonic stem cells by the orchestrated balance of canonical Wnt/β-catenin, Activin/Nodal and BMP signaling," Development, 135:2969-2979 (2008).
Suter et al., "A Sox1 to Pax6 switch drives neuroectoderm to radial glia progression during differentiation of mouse embryonic stem cells," Stem Cells, 27(1):49-58 (2009).
Takahashi et al., "Induction of Pluripotent Stem Cells from Adult Human Fibroblasts by Defined Factors," Cell, 131:861-872 (2007).
Tesar et al., "New cell lines from mouse epiblast share defining features with human embryonic stem cells," Nature, 448:196-199 (2007).
Tomishima et al., "Production of Green Fluorescent Protein Transgenic Embryonic Stem Cells Using the GENSAT Bacterial Artificial Chromosome Library," Stem Cells, 25(439-45 (2007).
Valenzuela et al., "Identification of Mammalian Noggin and Its Expression in the Adult Nervous System," J. Neurosci., 15(9):6077-6084 (1995).
Vallier et al., "Nodal Inhibits Differentiation of Human Embryonic Stem Cells Along the Neuroectodermal Default Pathway," Dev Biol., 275(2):403-421 (2004).
Venezia et al., "Molecular Signatures of Proliferation and Quiescence in Hematopoietic Stem Cells," PLoS Biol., 2(10):e301 (2004).
Wang et al., "Noggin and bFGF cooperate to maintain the pluripotency of human embryonic stem cells in the absence of feeder layers," Biochem Biophys Res Commun., 330:934-942 (2005).
Watanabe et al., "A ROCK inhibitor permits survival of dissociated human embryonic stem cells," Nat. Biotechnol., 25(6):681-686 (2007).
Watanabe et al., "Directed differentiation of telencephalic precursors from embryonic stem cells," Nat. Neuro., 3:288-296 (2005).
Weinstein et al., "Neural Induction," Annu Rev Cell Dev Biol., 15:411-433, pp. 411-424 (1999a).
Weinstein et al., "Neural Induction," Annu Rev Cell Dev Biol., 15:411-433, pp. 425-433 (1999b).
Wichterle et al., "Directed Differentiation of Embryonic Stem Cells into Motor Neurons," Cell, 110:385-397 (2002).
Xu et al., "BMP4 initiates human embryonic stem cell differentiation to trophoblast," Nat Biotechnol., 20(12):1261 (2002).
Xu et al., "Basic FGF and suppression of BMP signaling sustain undifferentiated proliferation of human ES cells," Nat Methods, 2:185-190 (2005).
Xu et al., "NANOG is a Direct Target of TGFβ/Activin-Mediated SMAD Signaling in Human ESCs," Cell Stem Cell, 3:196-206 (2008).
Zhang et al., "In vitro differentiation of transplantable neural precursors from human embryonic stem cells," Nature Biotechnology, 19:1129-1133 (2001).
Zoltewicz et al., "oto is a homeotic locus with a role in anteroposterior development that is partially redundant with Lim1," Development, 126:5085-5095 (1999).
U.S. Appl. No. 15/077,012, Sep. 12, 2017 Response to Non-Final Office Action.
U.S. Appl. No. 14/922,110, Jul. 10, 2017 Restriction Requirement.
U.S. Appl. No. 14/356,042, Sep. 19, 2017 Final Office Action.
U.S. Appl. No. 14/356,042, Aug. 21, 2017 Response after Final Action.
U.S. Appl. No. 14/356,042, Jul. 24, 2017 Final Office Action.
Eldar-Finkelman et al., "GSK-3 inhibitors: preclinical and clinical focus on CNS," Frontiers in Molecular Neuroscience 4(32):1-18 (2011).
El Maarouf et al., "Use of polysialic acid in repair of the central nervous system," PNAS 103(45):16989-16994 (2006).
U.S. Appl. No. 14/168,835, Apr. 25, 2018 Non-Final Office Action.
U.S. Appl. No. 14/168,835, Apr. 16, 2018 Applicant Initiated Interview Summary.

(56) References Cited

OTHER PUBLICATIONS

U.S. Appl. No. 14/168,835, Apr. 16, 2018 Request for Continued Examination (RCE).
U.S. Appl. No. 14/168,835, Apr. 10, 2018 Advisory Action.
U.S. Appl. No. 14/168,835, Mar. 16, 2018 Response after Final Action.
U.S. Appl. No. 14/168,835, Jan. 17, 2018 Final Office Action.
U.S. Appl. No. 14/168,835, Nov. 16, 2017 Response to Non-Final Office Action.
U.S. Appl. No. 14/356,042, May 16, 2018 Non-Final Office Action.
U.S. Appl. No. 14/356,042, Mar. 19, 2018 Amendment and Request for Continued Examination (RCE).
U.S. Appl. No. 14/356,042, Mar. 14, 2018 Applicant Initiated Interview Summary.
U.S. Appl. No. 14/922,110, May 17, 2018 Non-Final Office Action.
U.S. Appl. No. 14/922,110, Jan. 3, 2018 Response to Restriction Requirement.
U.S. Appl. No. 15/077,012, Mar. 22, 2018 Notice of Allowance.
U.S. Appl. No. 15/077,012, Jan. 16, 2018 Response to Restriction Requirement.
U.S. Appl. No. 15/077,012, Nov. 3, 2017 Restriction Requirement.
Brevini et al., "No shortcuts to pig embryonic stem cells," Theriogenology, 74:544-550 (2010).
Cai et al., "BMP and TGF-β pathway mediators are critical upstream regulators of Wnt signaling during midbrain dopamine differentiation in human pluripotent stem cells," Developmental Biology, 376:62-73 (2013).
Lupo et al., "Multiple roles of Activin/Nodal, bone morphogenetic protein, fibroblast growth factor and Wnt/β-catenin signaling in the anterior neural patterning of adherent human embryonic stem cell cultures," Open Biol., 3:120167 (2013) (13 pages).
Maroof et al., "Prospective Isolation of Cortical Interneuron Precursors from Mouse Embryonic Stem Cells," J. Neurosci, 30(13):4667-4675 (2010).
Munoz et al., "Constraints to Progress in Embryonic Stem Cells from Domestic Species," Stem Cell Rev. and Rep., 5:6-9 (2009).
NIH (Stem Cell: Scientific Progress and Future Research Directions, Department of Health and Human Services, Chapter 1, pp. 1-4, Jun. 2001.
Oliveri, "Epigenetic dedifferentiation of somatic cells into pluripotency: cellular alchemy in the age of regenerative medicine?" Regen. Med., 2(5):795-816 (2007).
Paris et al., "Equine embryos and embryonic stem cells: Defining reliable markers of pluripotency," Theriogenology, 74:516-524 (2010).
Patel et al., "Advances in Reprogramming Somatic Cells to Induced Pluripotent Stem Cells," Stem Cell Rev., 6(3):367-380 (2010).
Wang et al., "Identification of select glucocorticoids as Smoothened agonists: Potential utility for regenerative medicine," PNAS 107(20):9323-9328 (2010).
Andersson et al., "Identification of Intrinsic Determinants of Midbrain Dopamine Neurons," Cell 124:393-405 (2006).
Deng et al., "Specific and integrated roles of Lmx1a, Lmx1b and Phox2a in ventral midbrain development," Development 138:3399-3408 (2011).

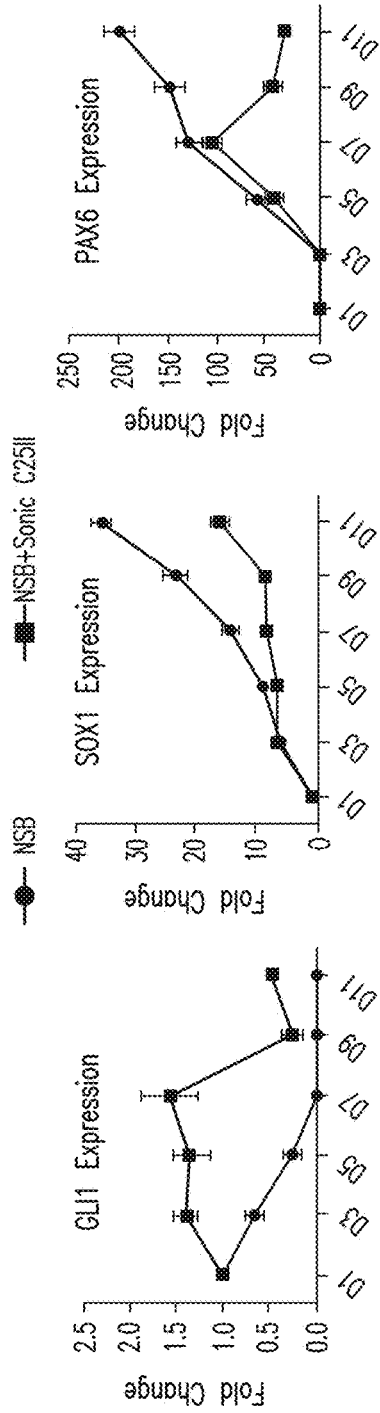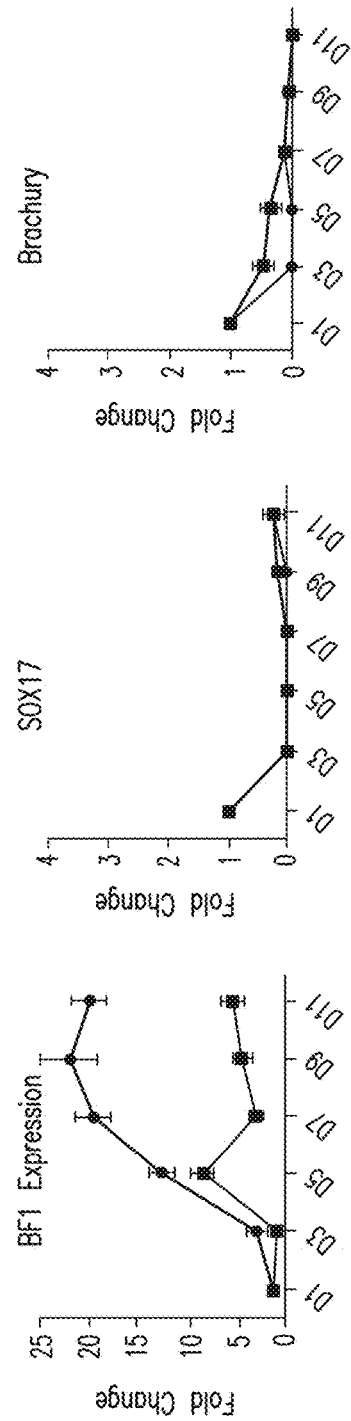

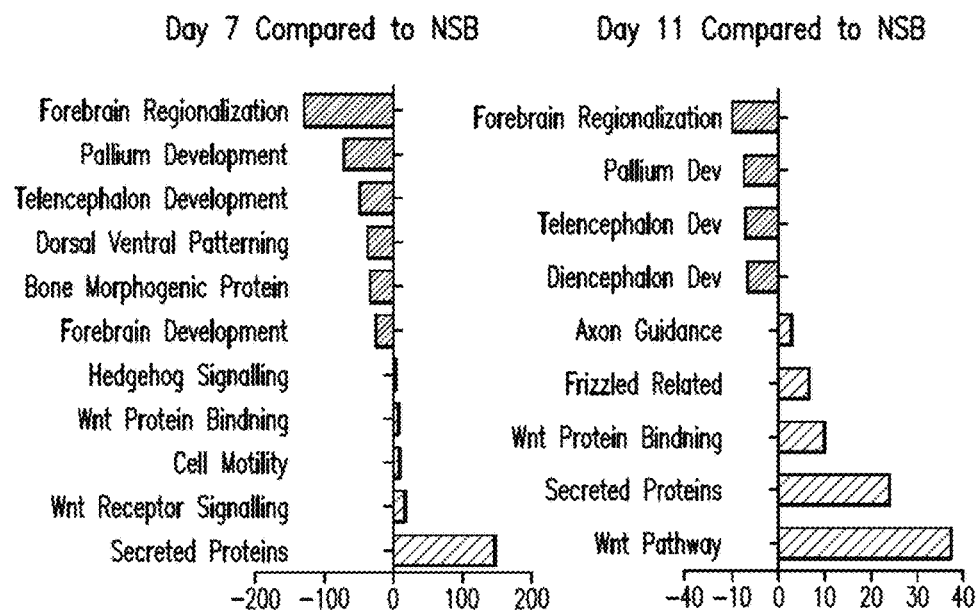
FIG. 18M
FIG. 18N
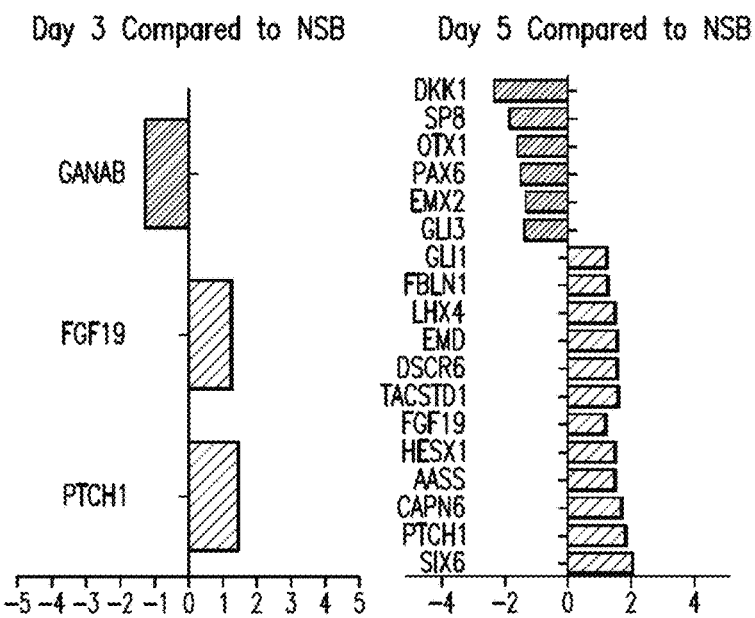
FIG. 18O
FIG. 18P

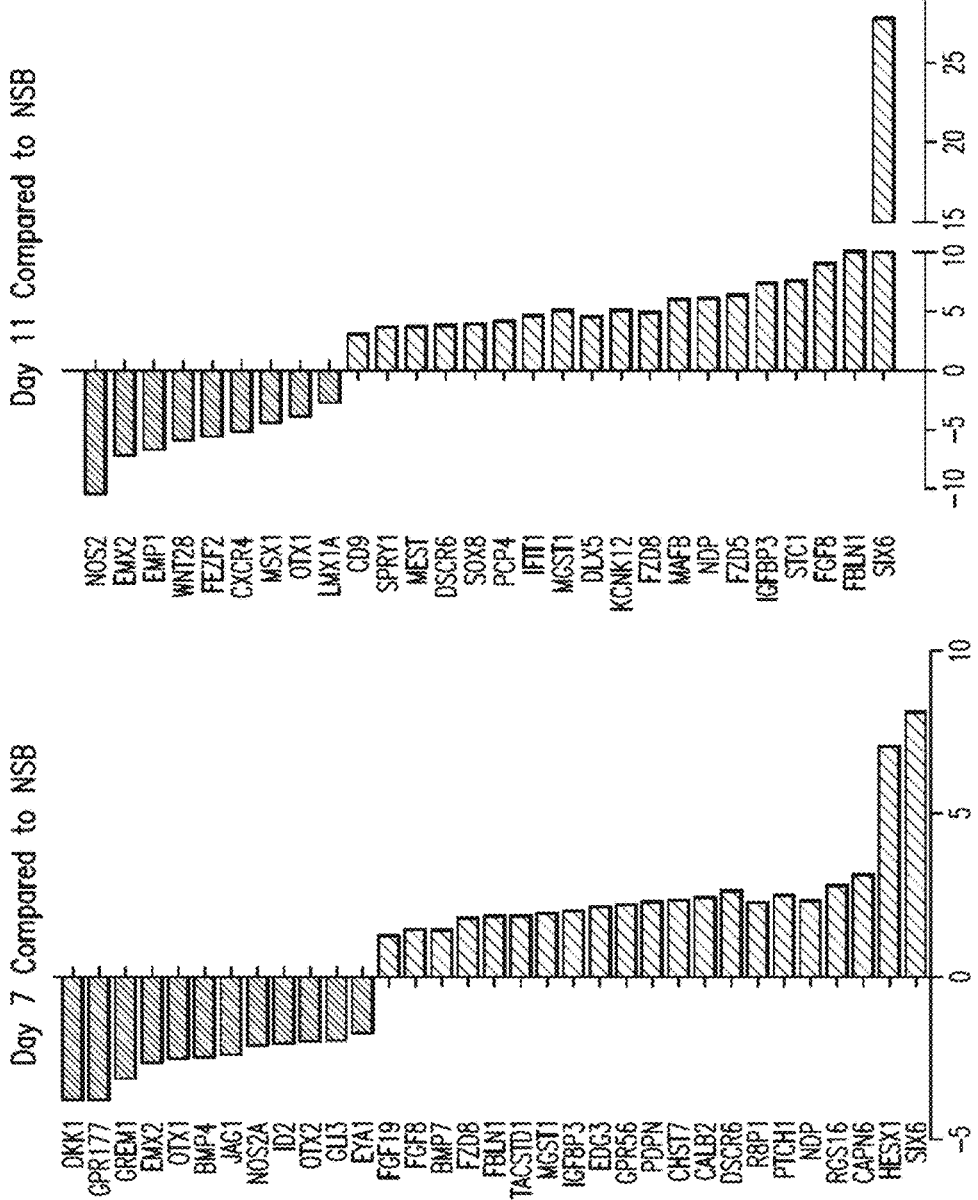

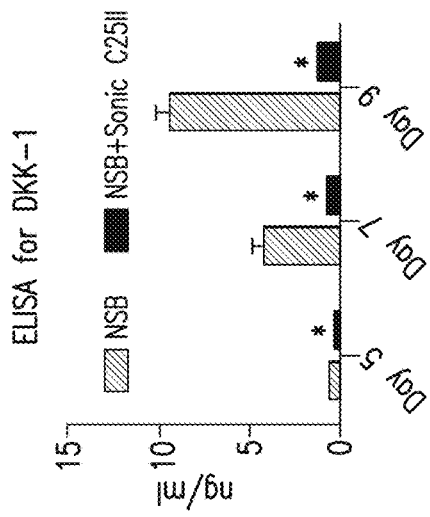
FIG. 19A
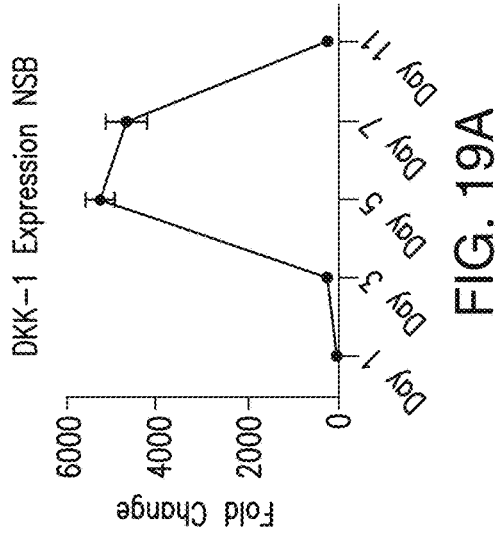
FIG. 19B
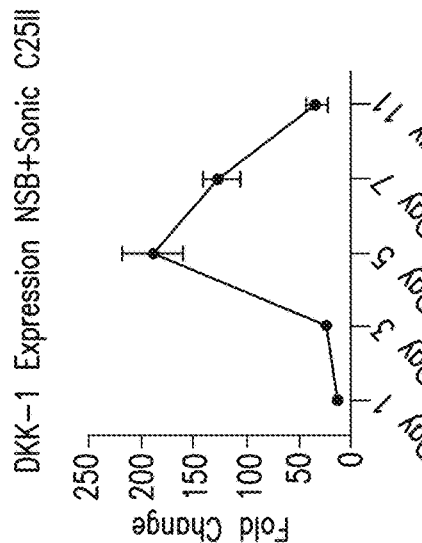
FIG. 19C
FIG. 19D

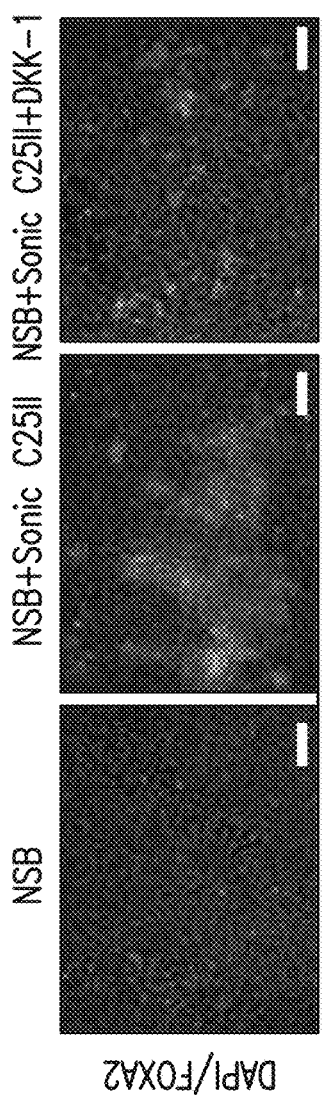
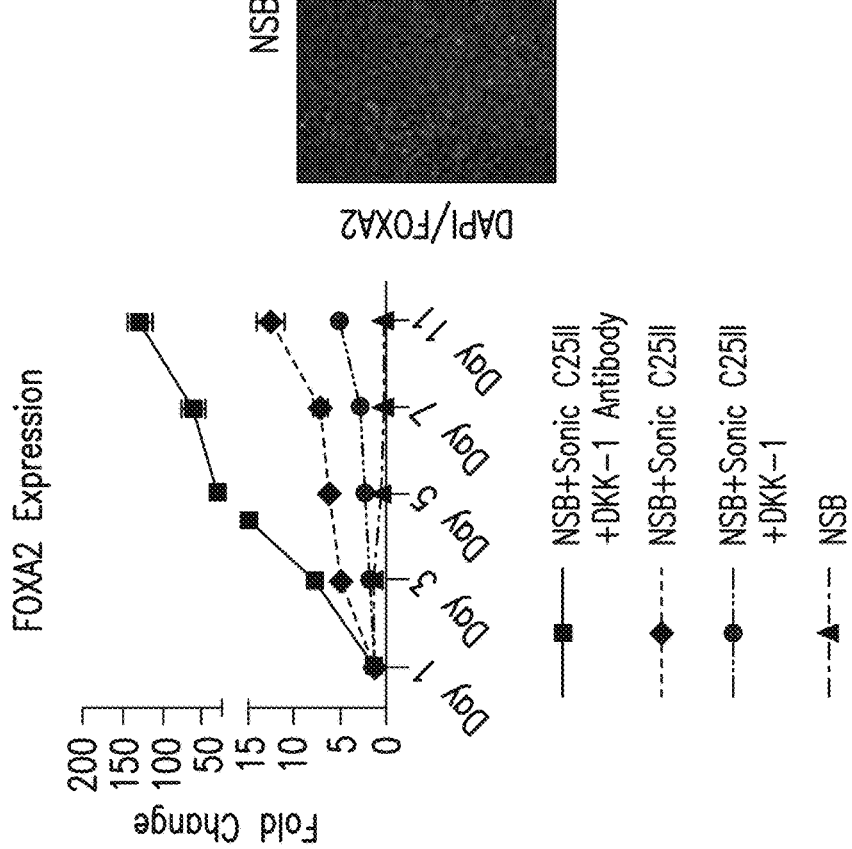
FIG. 19F
FIG. 19E

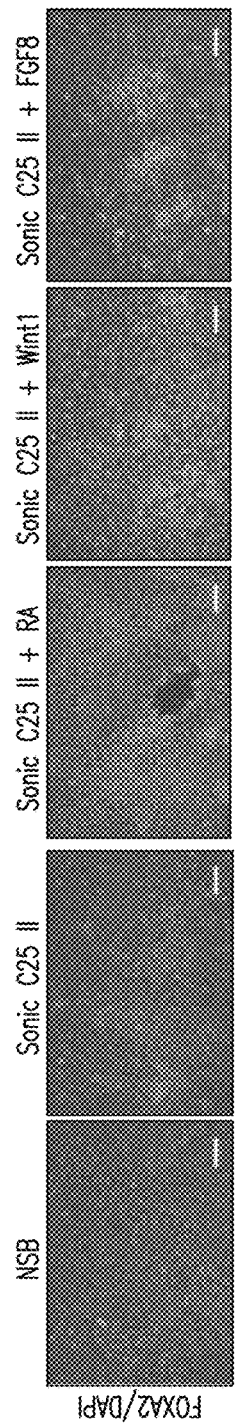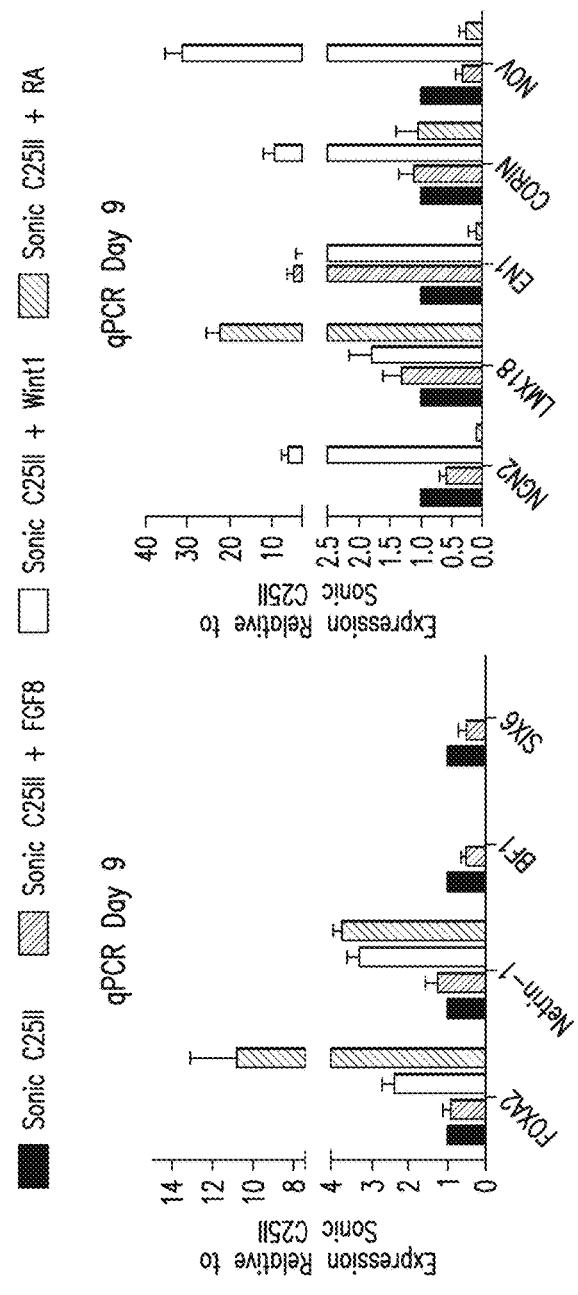
FIG. 20A
FIG. 20B
FIG. 20C

KITS FOR NEURAL CONVERSION OF HUMAN EMBRYONIC STEM CELLS

CROSS REFRERENCE TO RELATED APPLICATIONS

The present application is a Divisional of U.S. patent application Ser. No. 13/201,137 filed Nov. 10, 2011, which issued as U.S. Pat. No. 8,642,334, which is a United States National Stage Application under 35 U.S.C. § 371 of International Application No. PCT/US10/24487 filed Feb. 17, 2010, which claims priority to United States Provisional Application No. 61/296,796 filed Jan. 20, 2010, and United States Provisional Application No. 61/207,763 filed Feb. 17, 2009, the contents of each of which are incorporated by reference in their entireties herein, and priority to each of which is claimed.

GRANT INFORMATION

This invention was made with government support under NS052671 awarded by the National Institutes of Health. The government has certain rights in the invention.

FIELD OF THE INVENTION

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. Specifically, methods are provided for obtaining neural tissue, floor plate cells, and placode including induction of neural plate development in hESCs for obtaining midbrain dopamine (DA) neurons, motoneurons, and sensory neurons. Further, neural plate tissue obtained using methods of the present inventions are contemplated for use in co-cultures with other tissues as inducers for shifting differentiation pathways, i.e. patterning.

BACKGROUND OF THE INVENTION

The differentiation capacity of embryonic and somatic stem cells have opened possibilities for cell replacement therapies for genetic, malignant, and degenerative diseases. Neurodegenerative disorders, conditions, and diseases, and their treatment by cell-based therapies represent a promising means of preventing, reducing or eliminating the symptoms. Such disorders include Huntington's disease, Alzheimer's, Parkinson's, and amyotrophic lateral sclerosis. They also provide a source of cells for screening for critical small molecules (i) that could be useful in for treatment of disease; or (ii) for determining the cell fate of neural tissue. Further, these cells were studied in order to characterize key genes, mRNA transcripts, and proteins relevant in normal or pathological lineages.

Neural development is dictated in time and space by a complex set of signals that instruct neural precursor identity. While significant progress was made in animal models, human neural development remains much less understood.

Previous studies reported directed differentiation of mouse (Wichterle et al., 2002; Barberi et al., 2003; Watanabe et al., 2005) and human (Perrier et al., 2004; Li et al., 2008; Eiraku et al., 2008) ESCs into specific neuron types in response to patterning factors defining anterior/posterior (A/P) and dorso-/ventral (DN) CNS identity. These studies demonstrate evolutionary conservation of signaling systems that specify the major CNS regions. In mammals, sonic hedgehog (SHH) is the key ventralizing factor acting in a dose-dependent manner to specify the various ventral cell types including cells expressing floor plate (FP) in primary neural explants (Briscoe and Ericson, 1999) and in mouse ES cells (Mizuseki et al., 2003). While application of SHH to hESC-derived neural cells was shown to induce various ventral neuron types, the derivation of floor plate (FP) tissue itself was not reported. As FP is one of the most important signaling centers for inducing differentiation pathways and subsequent committed cell linage, the ability to produce FP from human ES cells would be a major step forward in furthering studies of early human neural development. Furthermore, little is known about FP development in humans, due to lack of accessibility to tissue.

In animals, the FP is a major site of SHH production and several human developmental disorders are related to alterations in midline SHH signaling (Mullor et al., 2002) including certain forms of holoprosencephaly and microphthalmia, skeletal disorders including various cleft plate syndromes, and tumor conditions such as Gorlin's syndrome; a rare genetic disorder caused by a mutation in the SHH receptor Patched 1. However it is not known whether similar alterations in midline SHH signaling would induce these diseases in humans.

Therefore there is a critical need for inducing human floor plate tissue from human embryonic stem cells (hESCs) for providing a source of human floor plate cells. These human floor plate cells are necessary for use in medical research for determining causes and treatments of developmental diseases in humans and for comparative developmental studies of human neural patterning and axonal pathfinding.

SUMMARY OF THE INVENTION

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. Specifically, methods are provided for obtaining neural tissue, floor plate cells, and placode including induction of neural plate development in hESCs for obtaining midbrain dopamine (DA) neurons, motorneurons, and sensory neurons. Further, neural plate tissue obtained using methods of the present inventions are contemplated for use in co-cultures with other tissues as inducers for shifting differentiation pathways, i.e. patterning.

The present invention is related to methods of obtaining populations of neural progenitor cells derived from human embryonic stem cells (hESCs), in particular for obtaining neural plate tissue. Specifically, methods of the present inventions induce neural plate floor development in hESCs for obtaining dopamine (DA) nerve cells. Further, neural plate floor tissue obtained using methods of the present inventions are contemplated for use in co-cultures with other tissues as inducers for shifting differentiation pathways, i.e. patterning.

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions.

The present inventions provide a method of producing a human neural cell (neural stem cells, neuronal subtypes, mature neurons, cells of a neural lineage) by (i) obtaining stem cells (hESCs, hiPSCs, somatic stem cells, cancer stem cells, human or mammalian pluripotent or multipotent cells); and (ii) culturing the human stem cell under conditions that block SMAD signaling. In a preferred embodiment, the methods for culture include conditions in a feeder-free system. In a preferred embodiment, the stem cells are cultured in a monolayer. A preferred embodiment contemplated the use of media that is supplemented with compounds Noggin and/or Dorsomorphin and SB431542.

In one embodiment the inventions provide a kit comprising a first inhibitor of Small Mothers Against Decapentaplegic (SMAD) protein signaling and a second inhibitor of Small Mothers Against Decapentaplegic (SMAD) protein signaling. In one embodiment, said first inhibitor is selected from the group consisting of a disulfide-linked homodimer of Noggin (SEQ ID NO:1), Dorsomorphin, LDN-193189, combination thereof and mixture thereof. In one embodiment, said Noggin is selected from mouse, human, rat, and xenopus. In one embodiment, said is Noggin is (SEQ ID NO:1) In one embodiment, said second inhibitor inhibits an anaplastic lymphoma kinase signaling pathway. In one embodiment, said second inhibitor inhibits a signaling pathway selected from the group consisting of Lefty, Activin, and TGFbeta. In one embodiment, said second inhibitor inhibits both activins and nodal signaling. In one embodiment, said second inhibitor is 4-[4-(1,3-benzodioxol-5-yl)-5-(2-pyridinyl)-1H-imidazol-2-yl]benzamide (SB431542) and derivatives thereof. In one embodiment, said kit further comprises a human stem cell. In one embodiment, the kit further comprises instructions.

In one embodiment the inventions provide a composition comprising a stem cell, a first inhibitor of Small Mothers Against Decapentaplegic (SMAD) protein signaling and a second inhibitor of Small Mothers Against Decapentaplegic (SMAD) protein signaling. In one embodiment, said first inhibitor is selected from the group consisting of a disulfide-linked homodimer of Noggin, Dorsomorphin, LDN-193189, combination thereof and mixture thereof. In one embodiment, said is Noggin is selected from mouse, human, rat, and xenopus. In one embodiment, said is Noggin is (SEQ ID NO:1) In one embodiment, said second inhibitor inhibits the Lefty/Activin/TGFbeta pathways by blocking phosphorylation of the ALK4, ALK5 and ALK7 receptors. In one embodiment, said second inhibitor inhibits activin/nodal signaling. In one embodiment, said second inhibitor is 4-[4-(1,3-benzodioxol-5-yl)-5-(2-pyridinyl)-1H-imidazol-2-yl]benzamide (SB431542) and derivatives thereof. In one embodiment, said stem cell is selected from the group consisting of human embryonic stem cells (hESC), somatic stem cells, and induced human pluripotent stem cells (hiPSC).

In one embodiment the inventions provide a method for inducing differentiation in stem cell, comprising, a) providing: i) a cell culture comprising human stem cells, ii) a first inhibitor of Small Mothers Against Decapentaplegic (SMAD) protein signaling, iii) a second inhibitor of Small Mothers Against Decapentaplegic (SMAD) protein signaling, and b) contacting said stem cells with said first inhibitor of Small Mothers Against Decapentaplegic (SMAD) protein signaling and said test compound under conditions for inducing differentiation in a stem cell into a non-default differentiated cell. In one embodiment, said first inhibitor is selected from the group consisting of a disulfide-linked homodimer of Noggin, Dorsomorphin, LDN-193189, combination thereof and mixture thereof. In one embodiment, said is Noggin is selected from mouse, human, rat, and xenopus. In one embodiment, said is Noggin is (SEQ ID NO:1) In one embodiment, said second inhibitor is a ALK4 receptor inhibitor. In one embodiment, said second inhibitor is 4-[4-(1,3-benzodioxol-5-yl)-5-(2-pyridinyl)-1H-imidazol-2-yl]benzamide (SB431542) and derivatives thereof. In one embodiment, said non-default differentiated cell is a neural progenitor cell. In one embodiment, said non-default differentiated cell is a part of a population of cultured cells. In one embodiment, said non-default differentiated cell is at least 10% up to 100% of said population of cultured cells. In one embodiment, said non-default differentiated cell in a population of cultured cells expresses paired box gene 6 protein. In one embodiment, said paired box gene 6 protein is expressed in at least 10% of said population of cultured cells. In one embodiment, said stem cell is selected from the group consisting of human embryonic stem cells (hESC), human somatic stem cells, and induced human pluripotent stem cells (hiPSC). In one embodiment, said non-default differentiated cell is a neural cell. In one embodiment, said neural cell is selected from the group consisting of dopamine positive neurons and floor plate cells.

In one embodiment the inventions provide a composition comprising isolated human embryonic neural cells. In one embodiment, said isolated human embryonic neural cells were derived from human embryonic cells. In one embodiment, said human embryonic neural cells are cultured in vitro. In one embodiment, said human embryonic neural cells are attached cells. In one embodiment, said composition is a co-culture further comprising a second cell type.

In one embodiment the inventions provide a method for screening biological agents, comprising, a) providing: i) a cell culture comprising human embryonic stem cells (hESCs), and ii) a test compound, and b) contacting said stem cells with said test compound under conditions for inducing neural floor plate cells. In one embodiment, said test compound is sonic hedgehog or fragment thereof. In one embodiment, said human embryonic stem cells are rosette-stage neural cells.

In one embodiment the inventions provide a method for providing differentiated cells, comprising, a) providing: i) a cell culture of human embryonic stem cells (hESCs), and ii) a compound for inducing differentiation, and b) contacting said stem cells with said test compound under conditions for inducing neural floor plate cells. In one embodiment, said compound is sonic hedgehog protein or fragment thereof. In one embodiment, said inducing consists of increasing a characteristic selected from the group consisting of flat cellular morphology, expressing sonic hedgehog, expressing forkhead box protein A2 (FOXA2), expressing Netrin-1, and expressing F-Spondin compared to said characteristic expressed in said human embryonic stems cells cultured without said test compound. In one embodiment, said inducing consists of decreasing a characteristic selected from the group consisting of rosette structures, BF1 expression, paired box homeotic gene-6 (PAX6) expression, NK6 homeobox 1 (NKX6.1), homeobox protein SIX6 expression compared to said characteristic in said human embryonic stems cells cultured without said test compound. In one embodiment, the method further provides and comprises a Noggin protein and an agent for blocking phosphorylation of a receptor selected from the group consisting of activin receptor-like kinase 4 (ALK4), activin receptor-like kinase 5 (ALK5) and activin receptor-like kinase 7 (ALK7) receptors and contacting said human stem cells with said noggin and said agent to human stem cells before adding said compound. In one embodiment, the method further provides an antibody, wherein said antibody is dickkopf homolog 1 (DKK-1) antibody, and contacting said stem cells with said antibody for reducing DKK-1 protein function. In one embodiment, the method further provides and comprises a caudalizing factor selected from the group consisting of wingless-type MMTV integration site family, member 1 (Wnt-1), and Retinoic Acid (RA). In one embodiment, the method further provides and comprises a neuron inducing compound and step c) adding said neuron inducing compound for inducing progenitor neurons. In one embodiment, said dopamine neurons express a marker selected from the group consisting of corin, serine peptidase (CORIN) and nephroblastoma overexpressed gene (NOV). In one embodiment, said progenitor neurons are dopamine neurons express a marker selected from the group consisting of LIM homeobox transcription factor 1, beta (LMX1B) and neurogenin 2 (NGN2). In one embodiment, the method further provides and comprises a stem cell, and step d) co-culturing said human neural floor plate cells with said stem cells for producing neurite outgrowth from said stem cells.

In one embodiment the inventions provide a neural floor plate cell produced by the methods described herein. In one embodiment the inventions provide a placode cell produced by the methods described herein. In one embodiment the inventions provide a lens cell produced by the methods described herein.

The invention contemplates methods for assessing the neural identity of the derived neural cells. This method may be through morphological means, functional assessment, and measurement of expression or downregulation of proteins associated with certain lineages. In a preferred method, dopaminergic activity or functional assays for motor neurons are utilized.

The present method can by employed to deliver agents or neural cells to the brain in an effective amount for diagnosis, prevention, treatment of disease, disorders, or for patients suffering from nerve damage form stroke. Such cells were co-committed towards a neural fate.

In one embodiment, the present invention contemplates a composition comprising isolated human embryonic floor plate cells. In one embodiment, the isolated human embryonic floor plate cells were derived from human embryonic cells. In one embodiment, the human embryonic floor plate cells are cultured in vitro. In one embodiment, the human embryonic floor plate cells are attached cells. In one embodiment, the composition is a co-culture further comprising a second cell type.

In one embodiment, the present invention contemplates a method for screening biological agents, comprising, a) providing: i) a cell culture comprising human embryonic stem cells (hESCs), and ii) a test compound, and b) contacting said stem cells with said test compound under conditions for inducing neural floor plate cells. In one embodiment, the test compound is sonic hedgehog or fragment thereof. In one embodiment, the human embryonic stem cells are rosette-stage neural cells.

In one embodiment, the present invention contemplates a method for providing differentiated cells, comprising, a) providing: i) a cell culture of human embryonic stem cells (hESCs), and ii) a compound for inducing differentiation, and b) contacting said stem cells with said test compound under conditions for inducing neural floor plate cells. In one embodiment, the compound is sonic hedgehog protein or fragment thereof. In one embodiment, the inducing consists of increasing a characteristic selected from the group consisting of flat cellular morphology, expressing sonic hedgehog, expressing forkhead box protein A2 (FOXA2), expressing Netrin-1, and expressing F-Spondin compared to said characteristic expressed in said human embryonic stems cells cultured without said test compound. In one embodiment, the inducing consists of decreasing a characteristic selected from the group consisting of rosette structures, BF1 expression, paired box homeotic gene-6 (PAX6) expression, NK6 homeobox 1 (NKX6.1), homeobox protein SIX6 expression compared to said characteristic in said human embryonic stems cells cultured without said test compound. In one embodiment, the method further provides Noggin protein and an agent for blocking phosphorylation of a receptor selected from the group consisting of activin receptor-like kinase 4 (ALK4), activin receptor-like kinase 5 (ALK5) and activin receptor-like kinase 7 (ALK7) receptors and contacting said human stem cells with said noggin and said agent to human stem cells before adding said compound. In one embodiment, the method further provides an antibody, wherein said antibody is dickkopf homolog 1 (DKK-1) antibody, and contacting said stem cells with said antibody for reducing DKK-1 protein function. In one embodiment, the method further provides a caudalizing factor selected from the group consisting of wingless-type MMTV integration site family, member 1 (Wnt-1), and Retinoic Acid (RA). In one embodiment, the further comprises, providing, a neuron inducing compound and step e) adding said neuron inducing compound for inducing progenitor neurons. In one embodiment, the dopamine neurons express a marker selected from the group consisting of corin, serine peptidase (CORIN) and nephroblastoma overexpressed gene (NOV). In one embodiment, the progenitor neurons are dopamine neurons express a marker selected from the group consisting of LIM homeobox transcription factor 1, beta (LMX1B) and neurogenin 2 (NGN2). In one embodiment, the method further comprises, providing, stem cells, and step d) co-culturing said human neural floor plate cells with said stem cells for producing neurite outgrowth from said stem cells.

Figure 3:
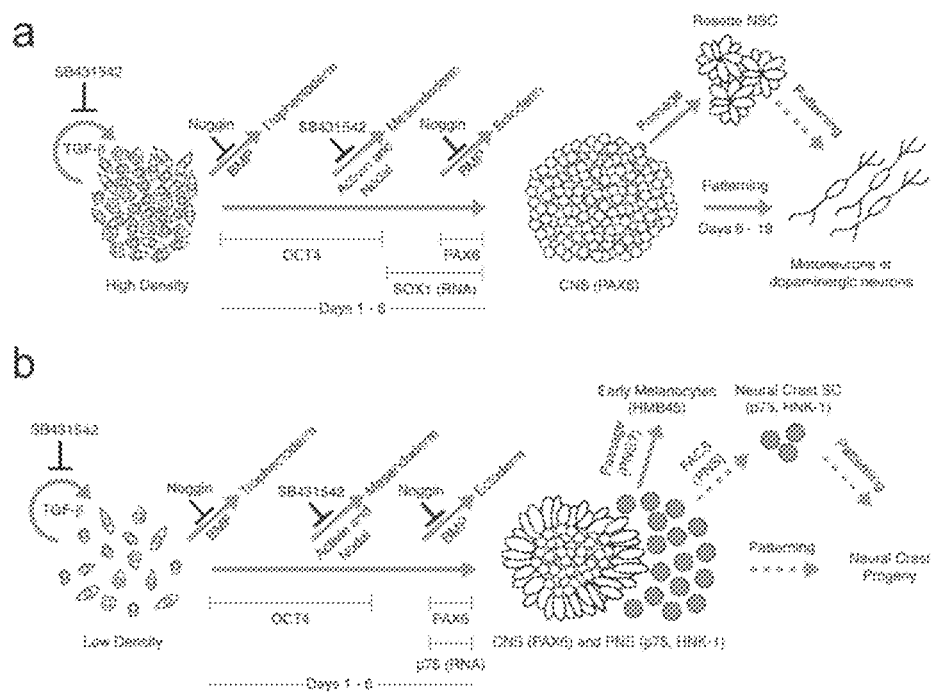

FIG. 3 showing an exemplary model of proposed mechanisms that contribute to the action of Noggin and SB431542. These include destabilizing the TGF/activin- and Nanog-mediated pluripotency network, suppression of mesendodermal fates by inhibiting endogenous activin and nodal signals, and promoting neuralization of primitive ectoderm through BMP inhibition. (a) At high density, primarily CNS cells that are PAX6+ are formed, which are capable of giving rise to R-NS cells and patternable neuronal populations of motoneurons and dopaminergic neurons within 19 d of differentiation. (b) At lower densities, both CNS fates with the properties described in (a) and neural crest fates are observed. Neural crest lineages include melanocytes and neural crest precursor cells amenable to patterning and subtype specification responses. In addition to cell density, it is likely that further manipulation of signaling pathways, including BMP pathways, will skew that ratio of CNS versus neural crest fates. Solid arrows indicate demonstrated cell fate potential; dashed arrows indicate proposed cell fates on the basis of current literature.

Figure 4:
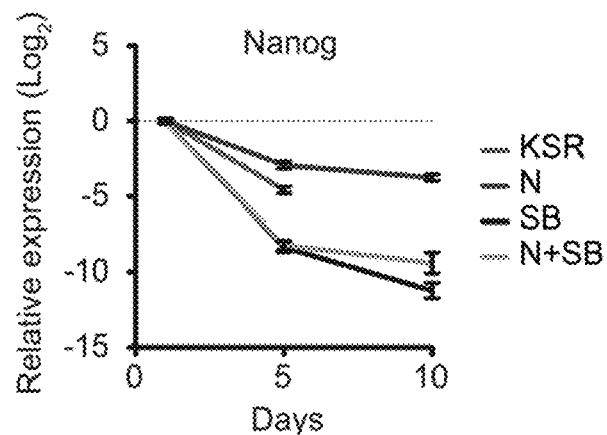

FIG. 4 showing exemplary nanog Real-Time gene expression. hESC treated with knock-out serum (KSR), Noggin (N), SB431542 (SB), or Noggin and SB431542 (N+SM) in KSR were examined for Nanog expression. The most dramatic downregulation was observed with the addition of SB431542. The error bars represent S.E.M.

Figure 5:
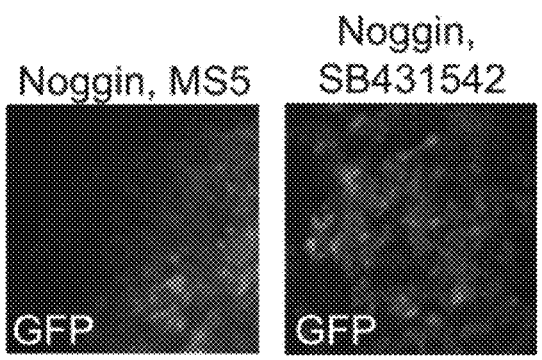

FIG. 5 showing exemplary GFP expression of HES5-GFP BAC reporter hESC line. GFP were observed under both conditions for neural induction (Noggin on MS5s or Noggin with SB431542 at day 13 of differentiation.

Figure 6:
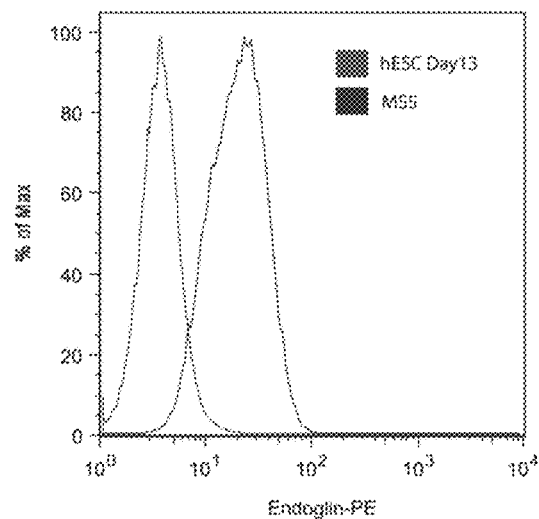

FIG. 6 showing exemplary endoglin (CD105) expression on MS5 feeder cells. MS5 cells used to differentiate hESC are uniformly positive for Endoglin (CD105) expression based on FACS analysis compared to hESC differentiated on day 13 using combined SMAD suppression. Endoglin expression was used to discriminate and remover MS5 cells from HES5-BAC hESC.

Figure 7:
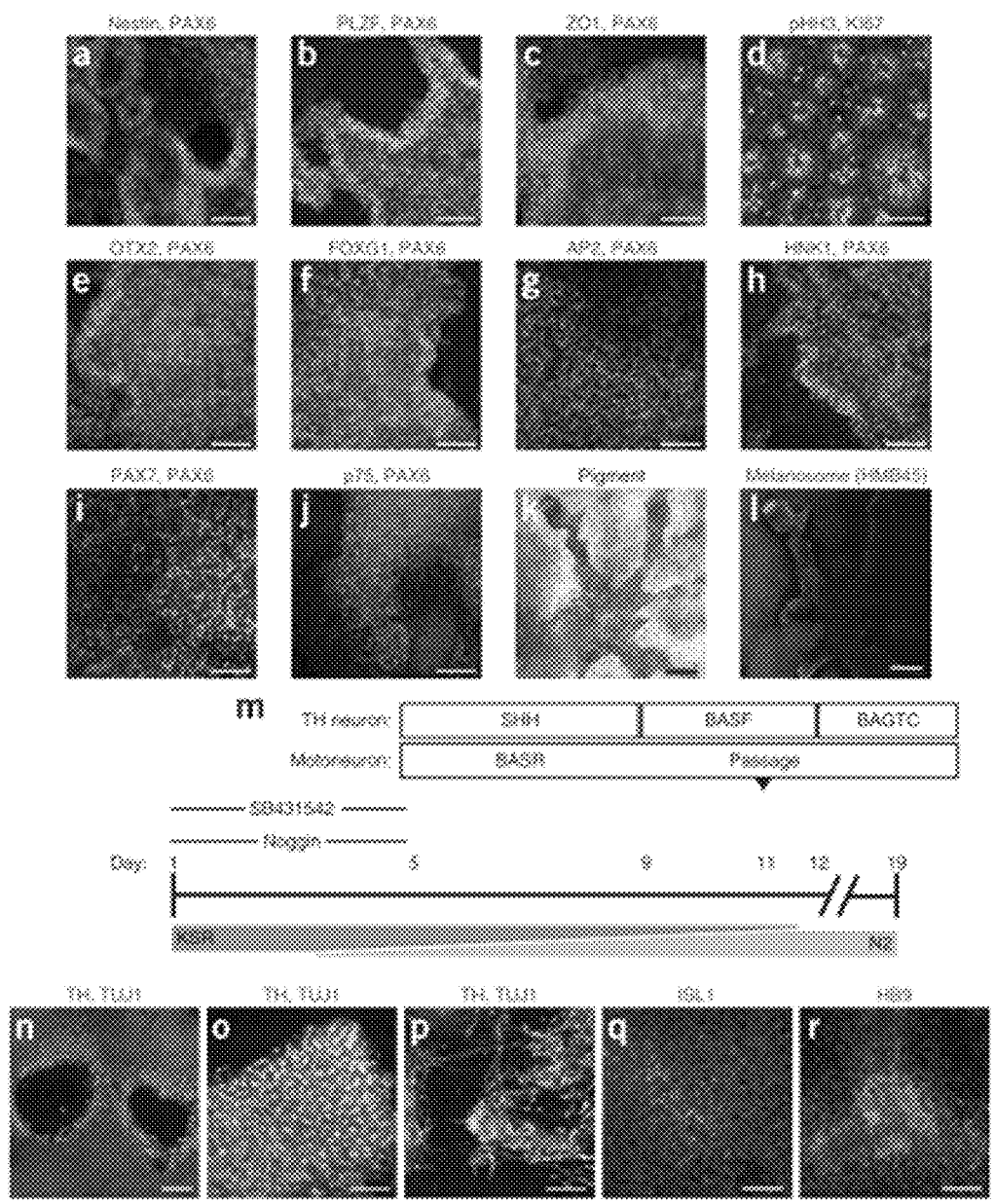

FIG. 7 showing exemplary neuralization of hESC by dual SMAD inhibition permits a pre-rosette, neural stem cell with dopaminergic and motor neuronal potential. The PAX6 positive neural tissue (green) expressed rosette markers (red) (a) Nestin, (b) PLZF, (c) ZO1. (d) Rosettes are formed when PAX6+ tissue is passaged to conditions promoting rosettes (BASF) confirmed by KI67 (green) and luminal phospho-Histone H3 (red) expression, evidence of interkinetic nuclear migration. In the absence of factors that confer regional neuronal specificity, the PAX6+ neural tissue (green) expressed (e) OTX2, and (f) BF1, indicating that the tissue defaults to forebrain specification. Neural crest could be identified on the periphery of the PAX6 positive tissue (green) based on (g) AP2, (h) HNK1, (i) PAX7, and (j) p75 expression (red). Upon passage, the neural crest cells gave rise to (k) pigmented cells (l) that expressed HMB45 (green), indicating melanosome synthesis. (m) Dopaminergic neuronal patterning was initiated with the addition of super sonic on day 5-9, followed by the addition of BDNF, ascorbic acid, sonic hedgehog, and FGF8 on day 9-12. Dopaminergic cells were matured on days 12-19 with BDNF, ascorbic acid, GDNF, TGFb3, and cAMP. Motor neuronal patterning was initiated at day 5 with the addition of BDNF, ascorbic acid, sonic hedgehog, and retinoic acid. Cells were passaged on day 11. (n-p) Without passage, tyrosine hydroxylase (TH) positive cells could be observed by day 19. (p) When passaged en bloc on day 12, more mature processes from TH positive cells were observed. For motoneuron induction, nuclear expression of the motor neuron markers (q) ISL1 and (r) HB9 were observed within a total of 19 days of differentiation from hESC. Scale bars: (a, b, c, e, f, g, h, i, j, o, p, q, and r)—100 μm; (c,d)—50 μm; (k,l,n)—200 μm.

Figure 8:
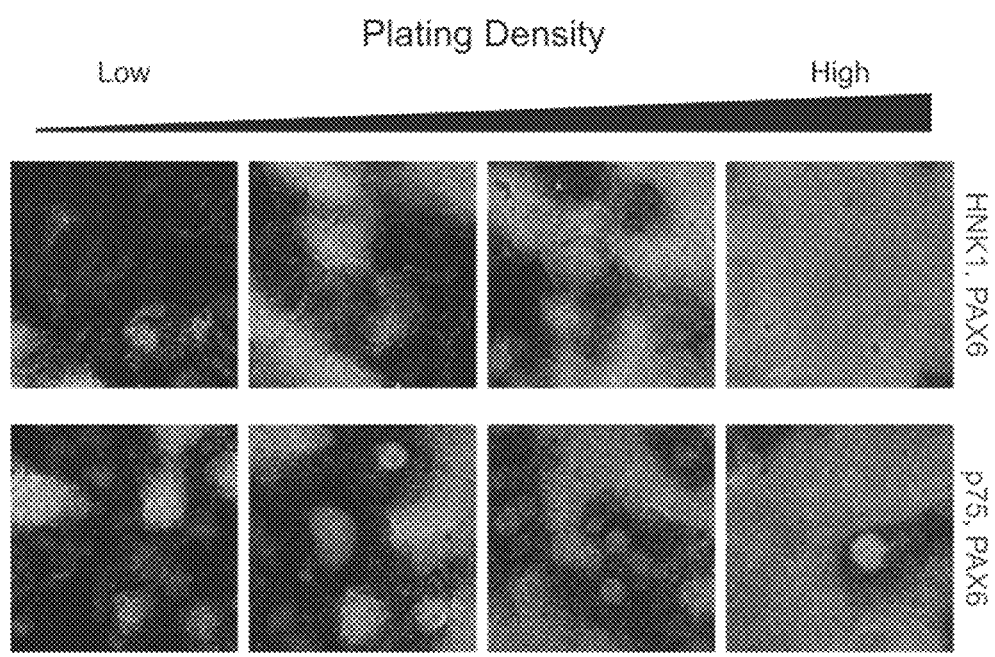

FIG. 8 showing exemplary plating density influences PNS vs. CNS cell generation. Initial hESC plating density determines the ratio of neural-crest (HNK1, p75; red) to neural tissue (PAX6; green) present at day 11 of differentiation, with higher densities favoring neural differentiation.

Figure 9:
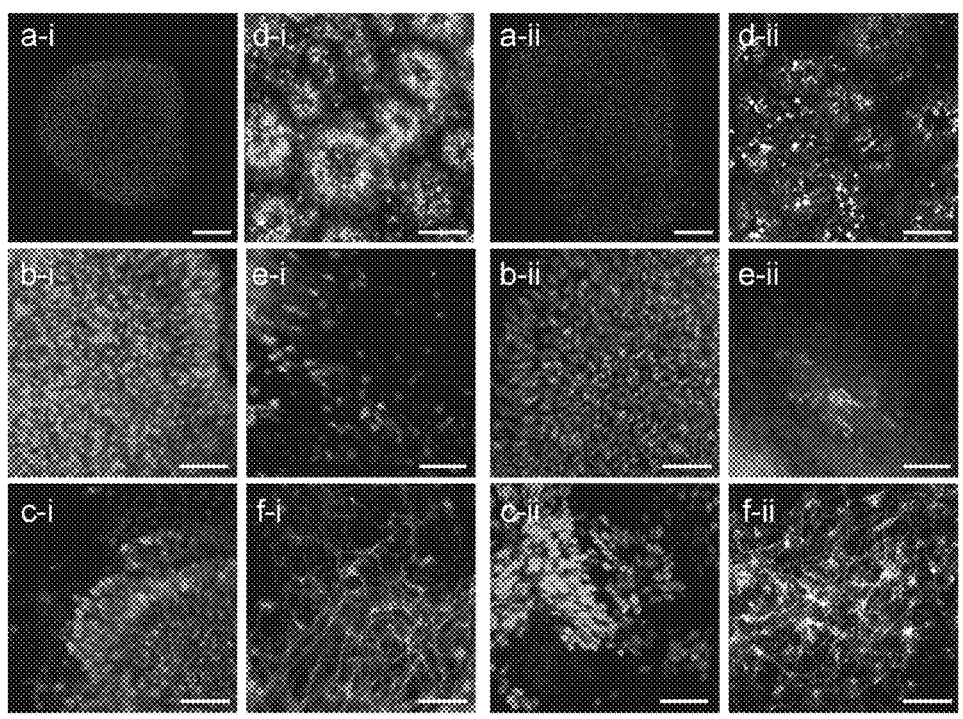

FIG. 9 showing exemplary induced pluripotent stem cells (IPS) were differentiated to neural tissue using dual SMAD inhibition and are patternable to dopaminergic neurons and motor neurons. (a-i, ii) Two IPS clones ($IPS^{C14}$, $IPS^{C27}$) were generated and screened for OCT4 (red) as well as additional pluripotency factors (Tra-1-81, Tra-1-60, SSEA-4 and Nanog). (b-i,ii) the two clones were neuralized by dual SMAD inhibition (PAX6 expression, green), and neural crest could be observed by HNK1 staining (c-i,ii). Neural tissue from the IPS clones could be induced to form rosette-NSCs (d-i,ii) based on KI-67 (red) and phospho-histone H3 (green) expression, motor neurons (e-i,ii) based on HB9 expression (green), and dopaminergic neurons (f-i,ii) based on TUJ1 (green) and TH (red) co-expression. Scale bars: 200 μm—(a); 50 μm—(b,c,d,e,f).

Figure 10:
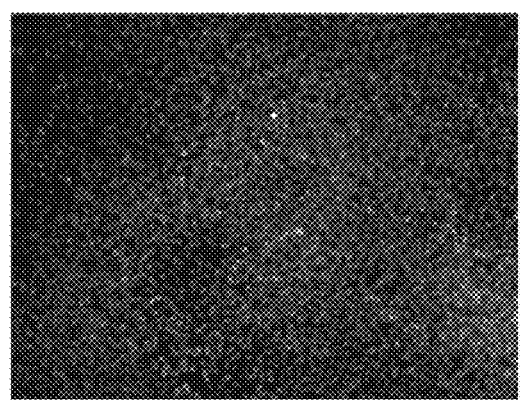

FIG. 10 showing exemplary combined SMAD inhibition during the first 5 days of neural-induction. Homogeneous PAX6 expression was observed on day 11 when SB431542 and Noggin, supplemented in the media, were withdrawn on day 5.

Figure 11:
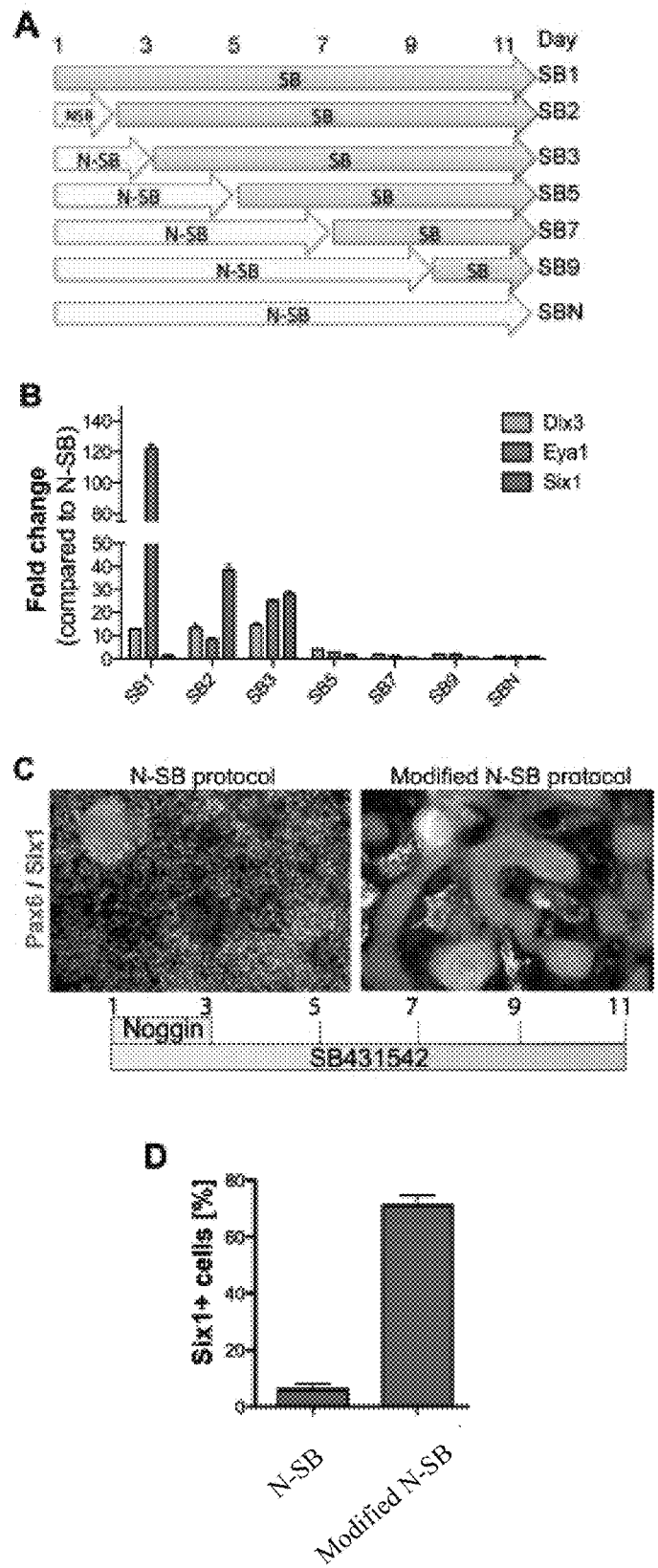

FIG. 11 showing exemplary derivation of Six1+ placodal precursors using a modified N-SB protocol. A) Schematic illustration of timed noggin withdrawal paradigm to determine temporal requirement for endogenous BMP signaling in placode cell specification.

B) Relative induction of placodal markers (Dlx3, Eya1, and Six1) comparing modified N-SB protocol as described in (A) to N-SB treatment maintained throughout differentiation (SBN condition). Optimal co-expression of Dlx3, Eya1, and Six1 was observed when the cells are treated with noggin for 48 hours. Data represent fold changes of mRNA expression measured by qRT-PCR at day 11. C) Immunocytochemical analyses showing Six1 (placodal marker) and Pax6 (anterior neuroectoderm marker) expression at day 11 of differentiation. Cells treated with the modified N-SB protocol (noggin withdrawal after 2 days of differentiation) show high percentages of Six1+ cells.D) Approximately seventy percent of cells generated using modified N-SB conditions (2 days of noggin) are Six1+ compared to standard (anterior neurectoderm-inducing) 11 days of noggin treatment.

Figure 12A:
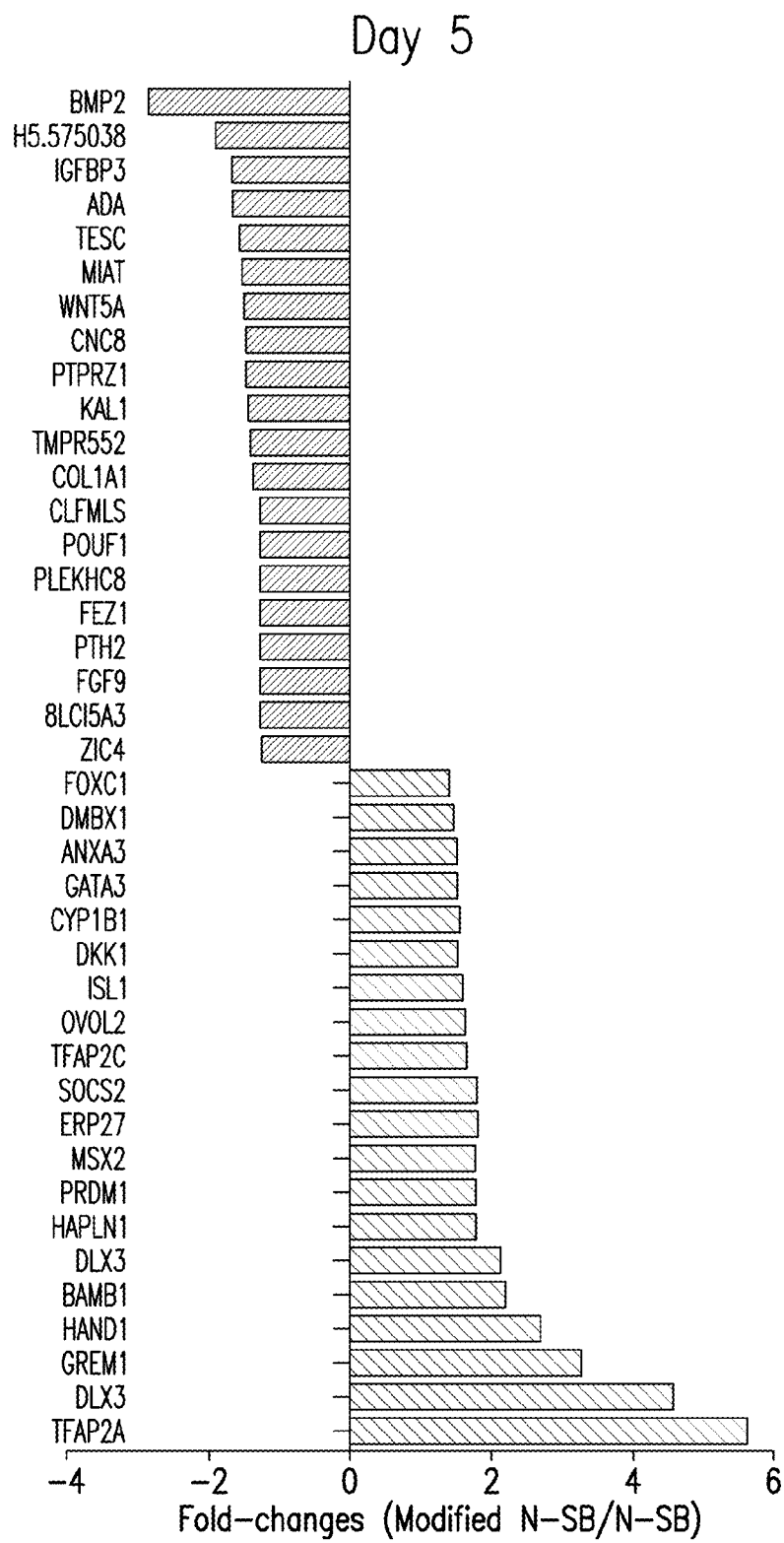
Figure 12B:
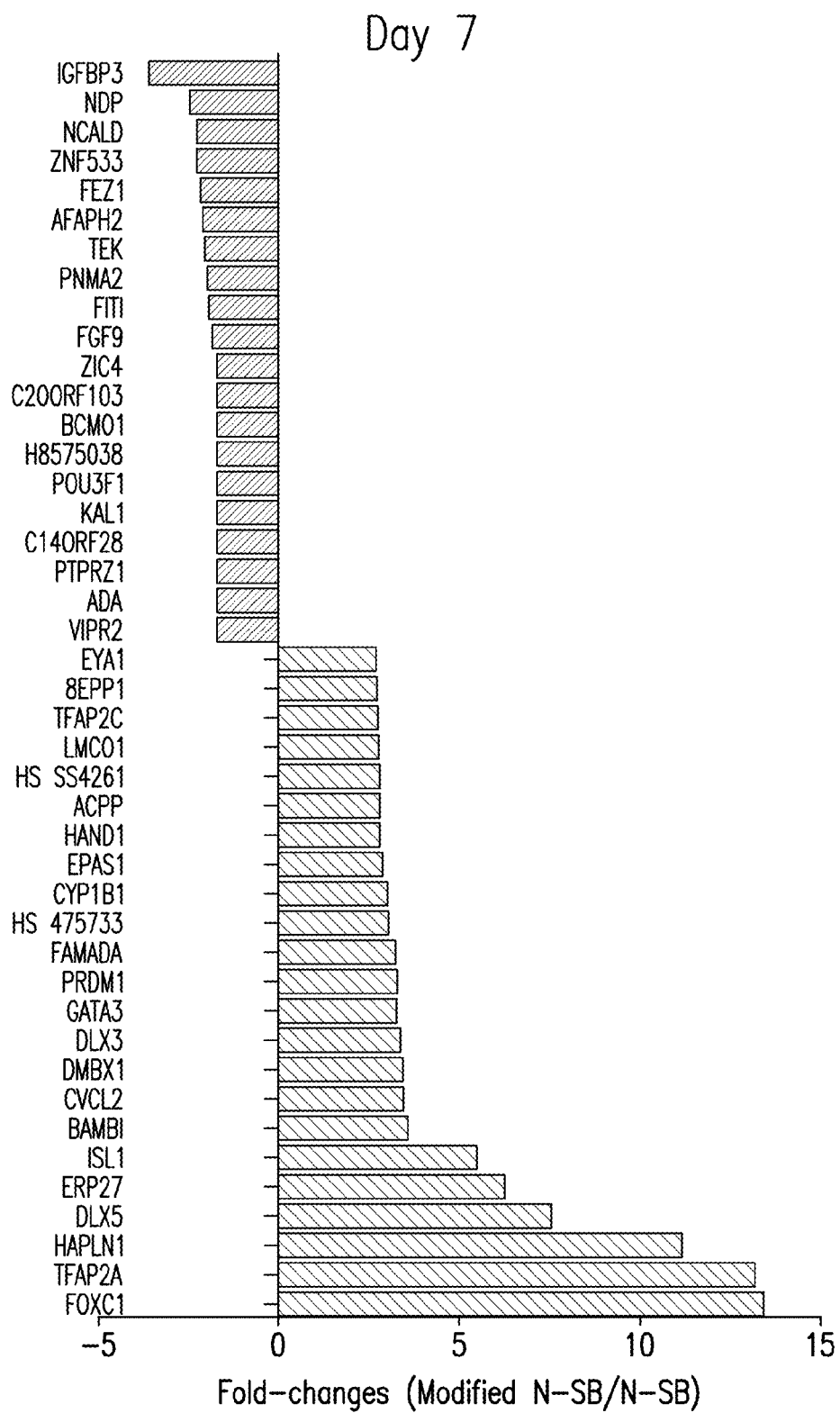
Figure 12C:
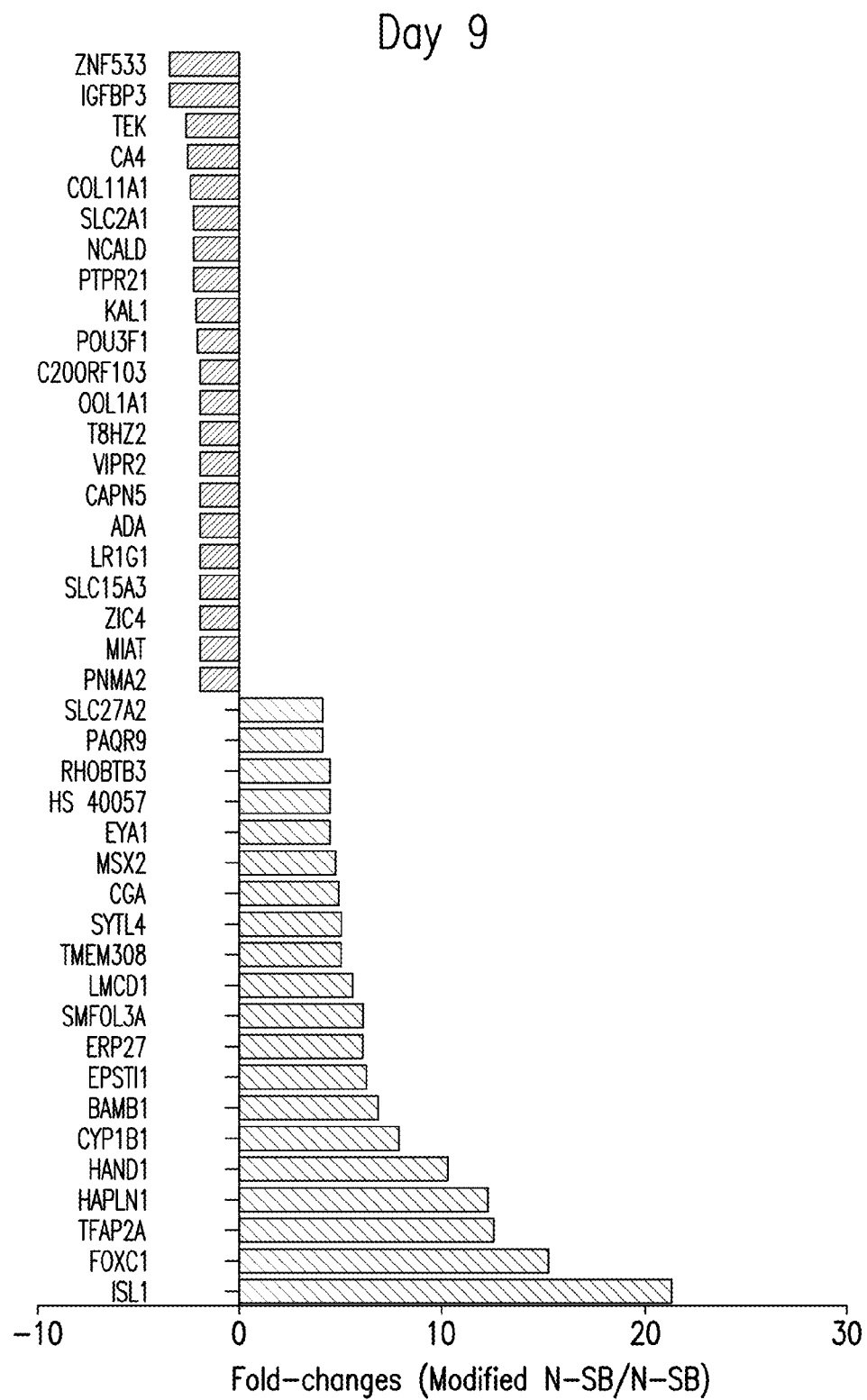
Figure 12D:
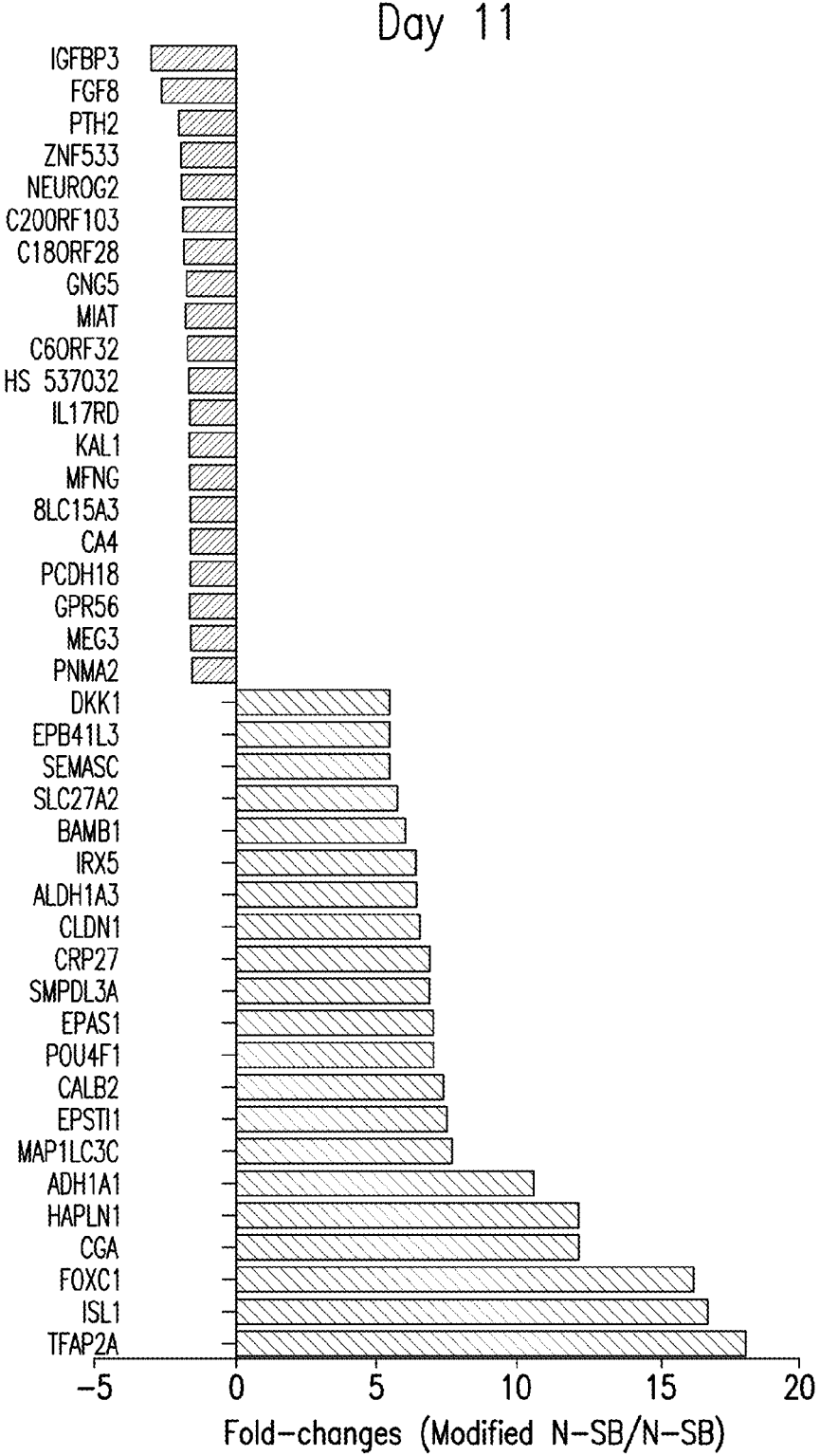
Figure 12E:
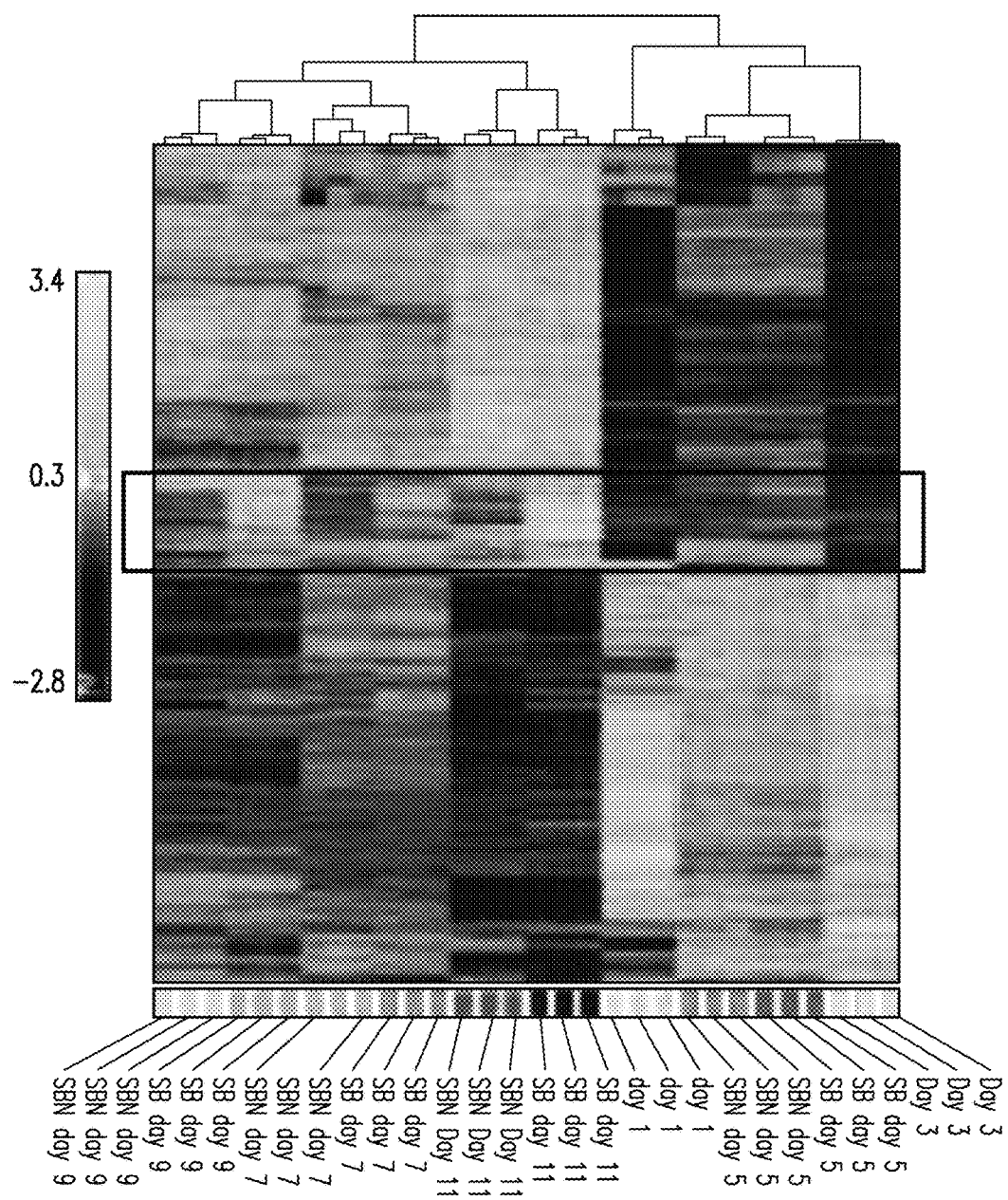
Figure 12F:
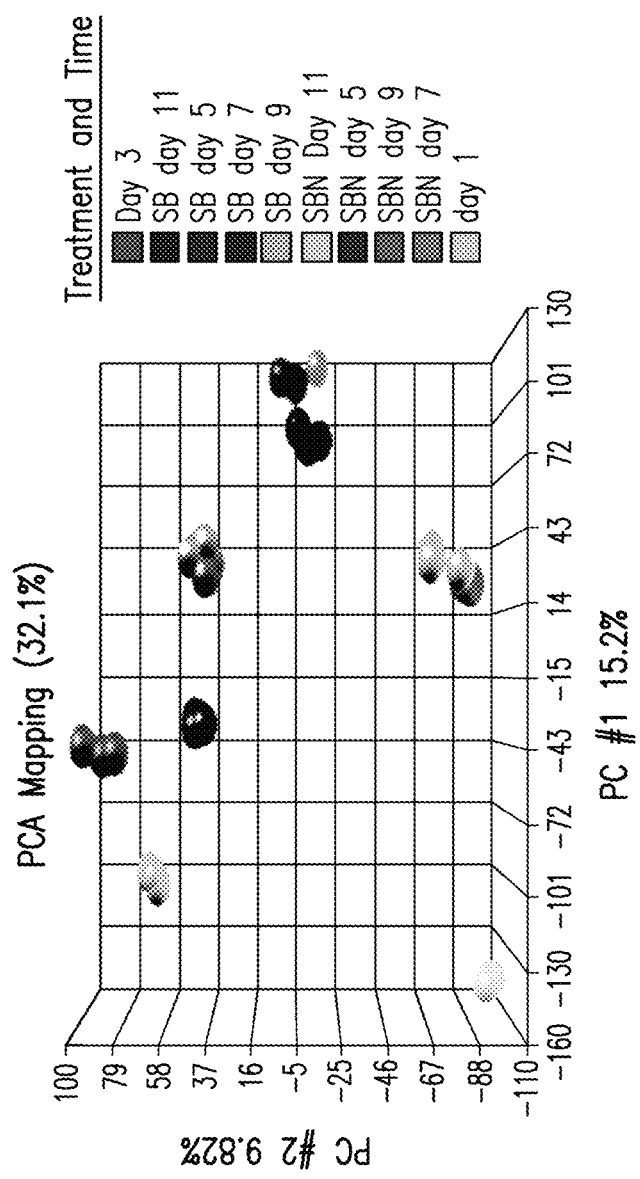
Figure 13:
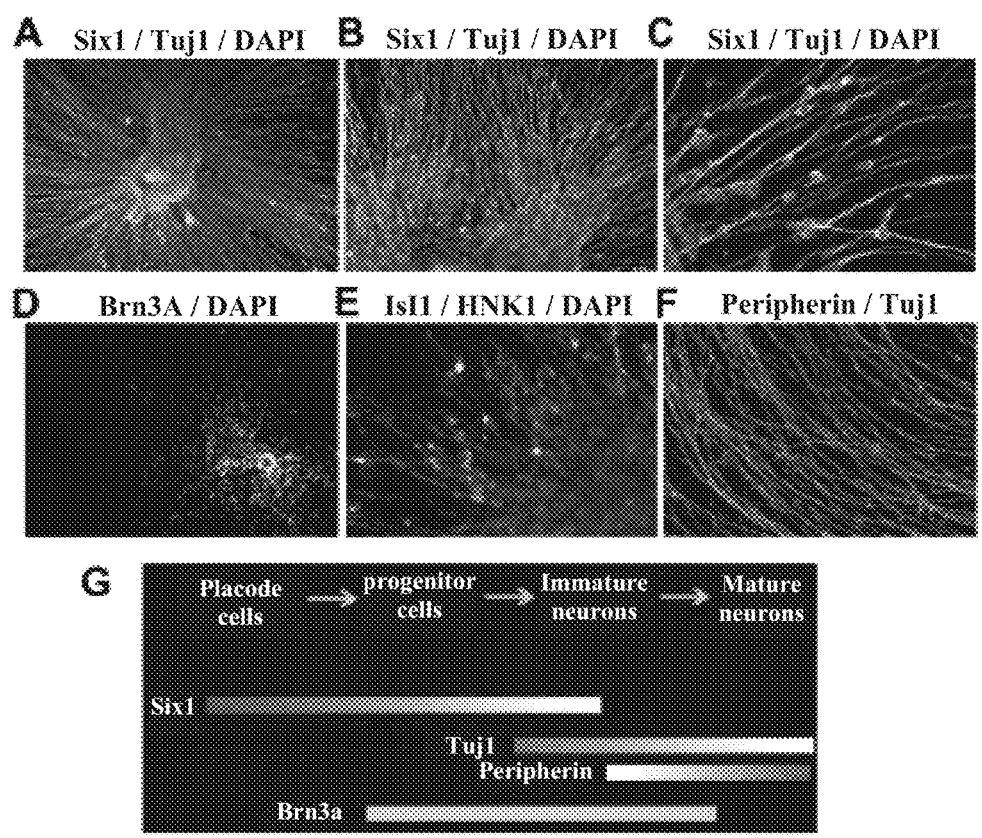

FIG. 12 showing exemplary temporal global gene expression profiles during human ES cell derived placode specification. A-D) Pair-wise comparison at day 5, day 7, day 9 and day 11 of differentiation of most the differentially expressed genes in hESC progeny subjected to the modified (placode-inducing) versus standard (anterior neuroectoderm-inducing) N-SB protocol. E) Unsupervised clustering of microarray data segregates data according to replicates, temporal sampling and treatment conditions. F) Principal component analysis of data confirms close temporal correlation of samples during human ES cell differentiation with increasing separation of modified versus standard N-SB treated cells at later differentiation stages FIG. 13 showing exemplary derivation of hESC placode derived sensory neurons. A-C) Immunocytochemical analysis at day 20 of differentiation demonstrates that placodal precursor cells efficiently yield neurons that initially retain Six1 expression. D, E) Sensory neuron identity is confirmed by expression of Brn3A and Isl1 in the majority of neurons derived from Six1+ clusters.F) At day 40 differentiation neurons show increased expression of peripherin and decreased levels of Tuj1 staining characteristic of a mature peripheral neuron fate. G) Schematic illustration of marker expression during sensory neuron specification from hESC derived placodal cells.

FIG. 14 showing exemplary prospective isolation of hESC derived placodal precursors. A) At day 11 of differentiation hESC derived cells are segregated into mutually exclusive p75+ and a Forse1+ precursor cell domains. B) FACS analysis at day 11 of differentiation for expression of p75 and HNK1.C) qRT-PCR data for Six1 mRNA expression following separation of cells based on the expression of p75 and HNK1. Cells single positive for p75 but negative for HNK1 (prospective placodal precursors) showed a dramatic increase in Six1 mRNA expression compared to other groups. D) An increase in the fraction of cells that are positive for p75 and negative for HNK1 is observed when precursors are derived under modified (placode-inducing) compared to the standard (anterior neuroectoderm-inducing) N-SB induction conditions.

Figure 15:
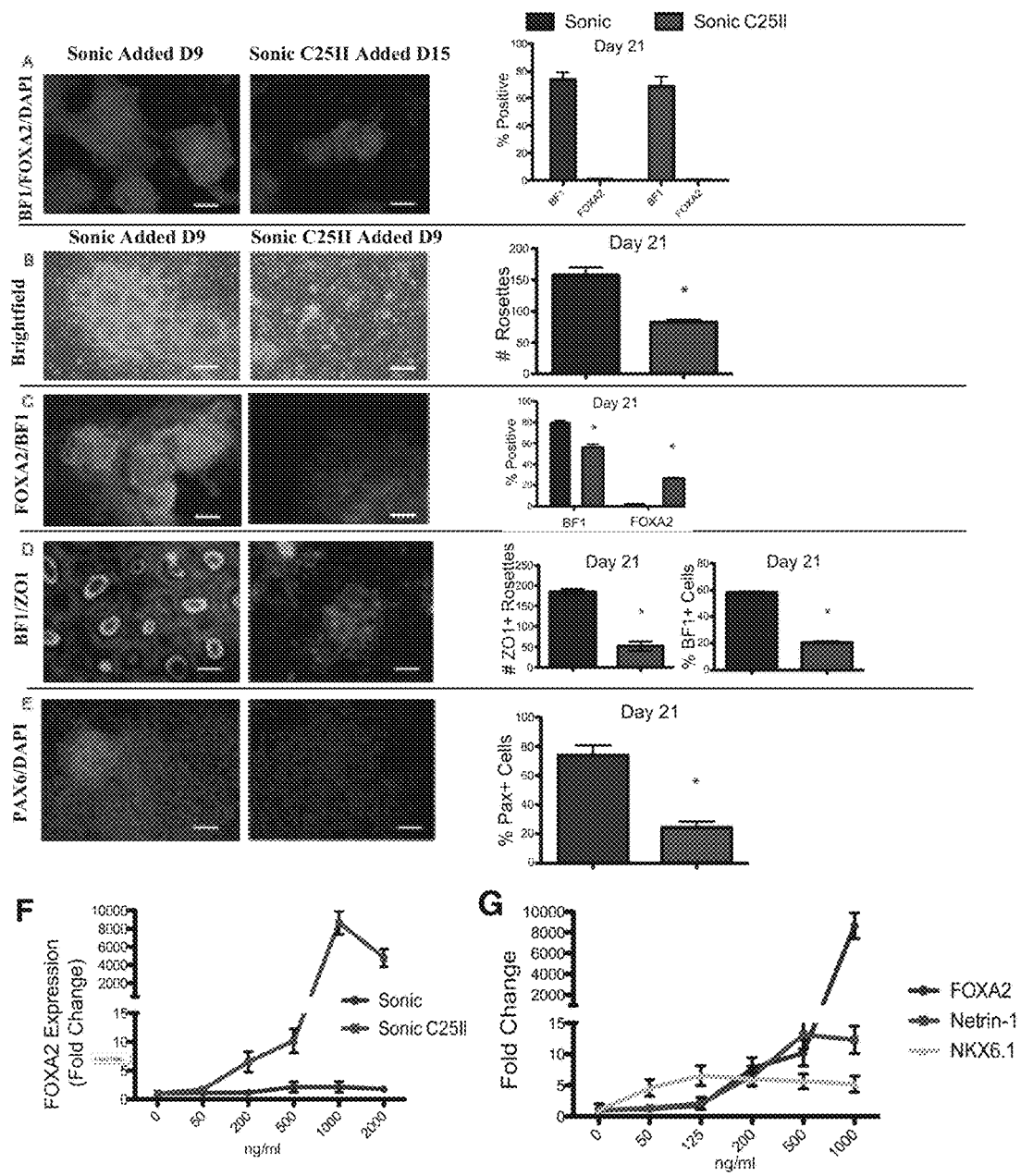

FIG. 15 showing exemplary high SHH levels increase FOXA2 and decrease BF1 expression. (A) Passage 1, Day 21 of neural differentiation shows no effect of SHH treatment when added at Day 15. Results quantified on right, *p<0.01 N=3. Scale bar, 200 µm. (B) Day 21 of neural differentiation shows a reduction of rosette like structures after Sonic C25II treatment Day 9. Loss of rosettes quantified on right, *p<0.01 N=4. Scale bar, 100 µm. (C) Sonic C25II treatment results in a decrease of BF1 and an increase in Foxa2 at Day 21. Quantified on right, *p<0.05 N=4. Scale bar, 200 µm. (D) Day 21 of neural differentiation reveals a decrease in ZO1/BF1+ rosette structures. This decrease is quantified, *p<0.01 N=4. Scale bar, 50 µm. (E) Decrease in PAX6 expression at Day 21 after Sonic C25II treatment. This decrease is quantified, *p<0.01 N=4. Scale bar, 200 µm. (F) Dose response curve comparing Sonic and Sonic C25II efficacy on FOXA2 induction. (G) Dose response curve of Sonic C25II comparing the induction of FP markers (FOXA2 and Netrin-1) to another SHH responsive gene NKX6.1.

Figure 16:
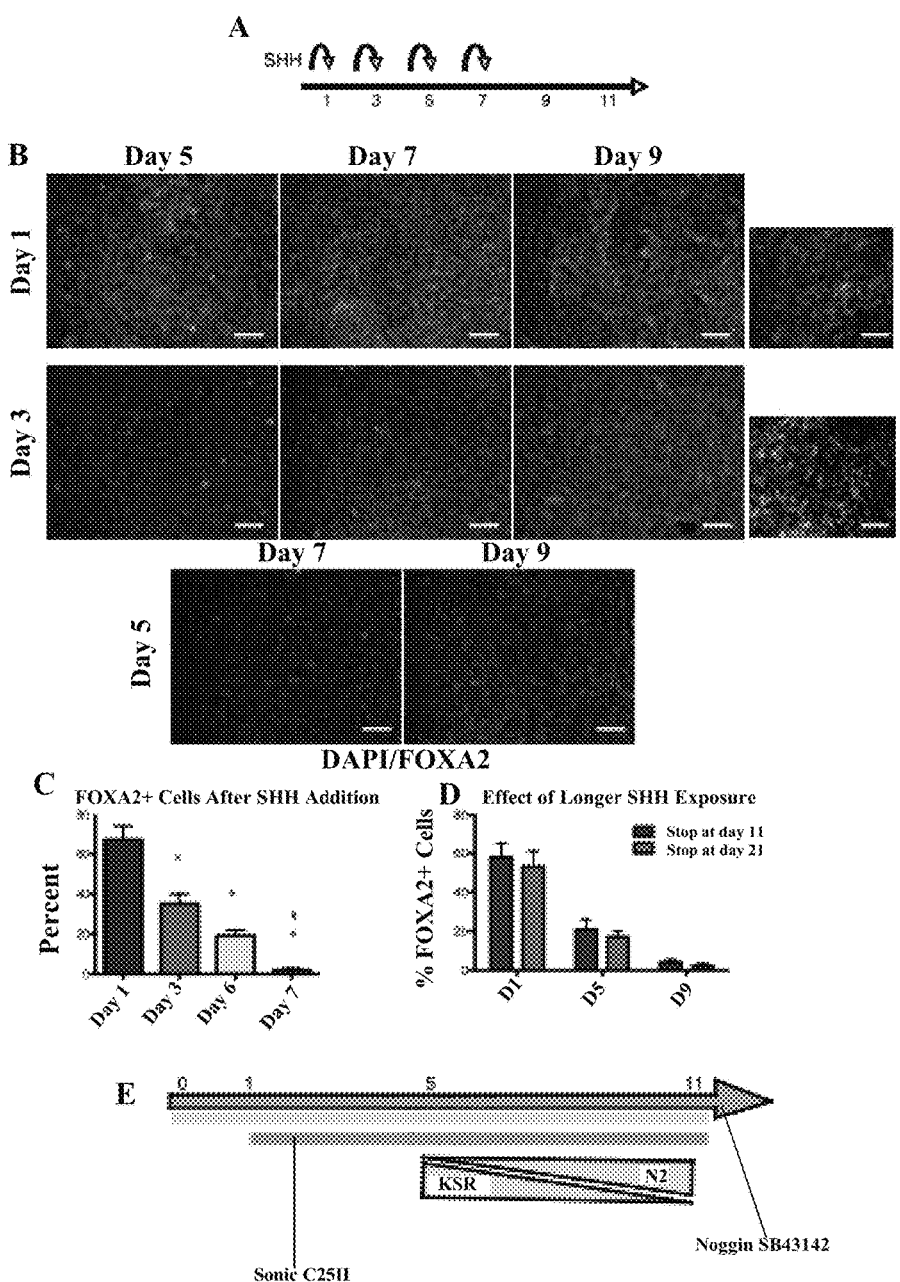

FIG. 16 showing exemplary floor plate induction has an early, short temporal patterning window (A) Schematic showing different time points of Sonic C25II additions during neural induction protocol. (B-C) Heading on the left delineates the day Sonic C25II was added, heading on the top delineates when the assay was stopped. The earlier Sonic C25II is added, and the longer the cells are exposed to it, leads to very high percentages of FOXA2. (C) This result is quantified, *p<0.01 N=3. Scale bars, 200 µm, high magnification, 50 µm. (D) Extended treatment with Sonic C25II (9 days of exposure) does not yield increased FOXA2 induction. (E) Schematic of optimal protocol for FOXA2 induction to be used for the rest of the study.

Figure 17:
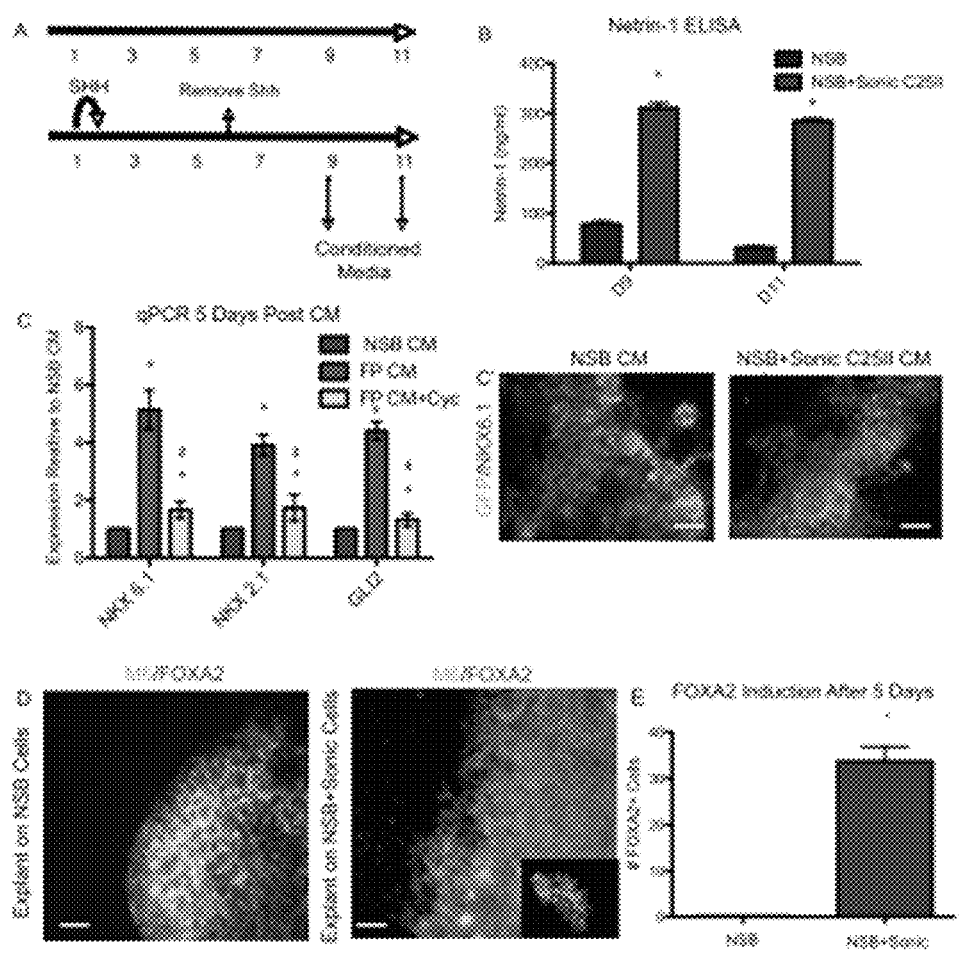

FIG. 17 showing exemplary hESC derived FP is functional (A) Schematic showing when conditioned media was collected. (B) ELISA showing an increase in levels of Netrin-1 secreted into the media at Days 9 and 11 when Sonic C25II is added early to the neural induction, *p<0.01 N=3. (C) Conditioned media from NSB and NSB+Sonic C25II was collected and placed on cultures containing NSB derived neural precursor cells qRT-PCR showing an induction of ventral genes (NKX6.1 and NKX2.1) as well as the SHH responsive gene (GLI2). These inductions are repressed in the presence of the SHH antagonist cyclopamine. (C') The induction of NKX6.1 is shown at the level of the protein using a GFP expressing line. *p<0.01 compared to NSB CM, #p<0.05 compared to FP CM, N=3. Scale bar, 200 µm. (D and E) Neural explants isolated from E8.5 neurectoderm co-cultured with NSB+Sonic C25II tissue show ectopic FOXA2 staining. Inset shows co-localization of M6 (Green) and FOXA2 (Red). (E) This data is quantified, *p<0.001 N=4 explants. Scale bar, 50 µm.

Figures 18A, 18B, 18C, 18D, 18E, 18F:
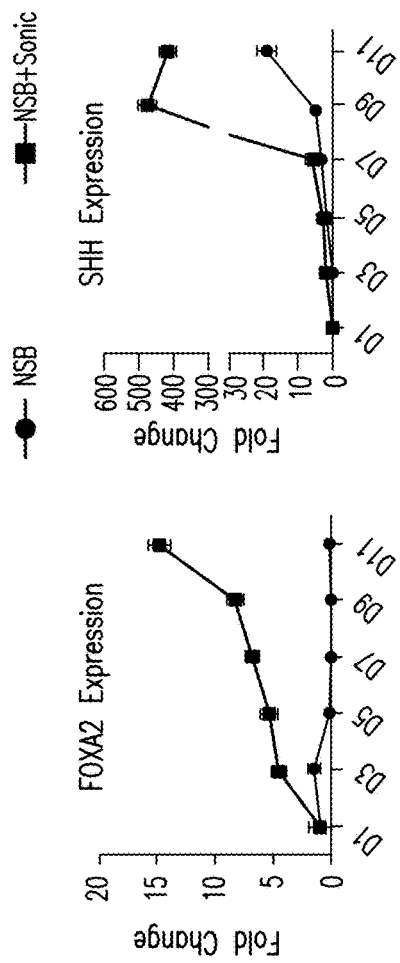
Figure 19H:
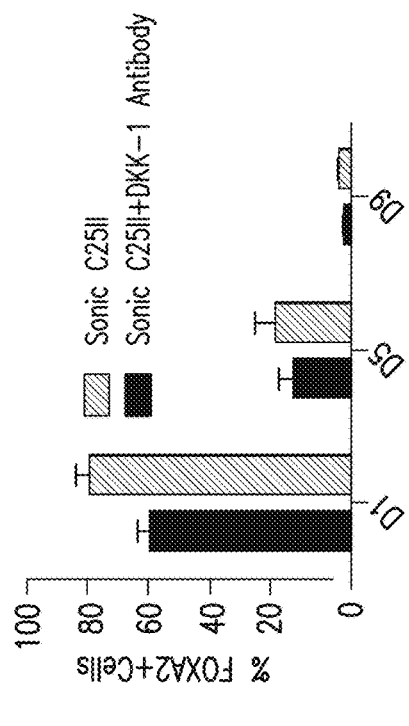
Figure 19I:
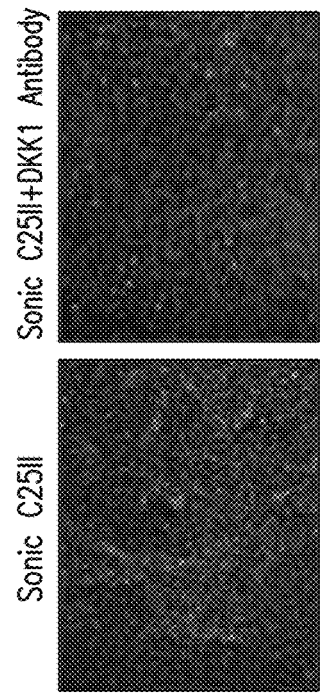
Figure 19G:
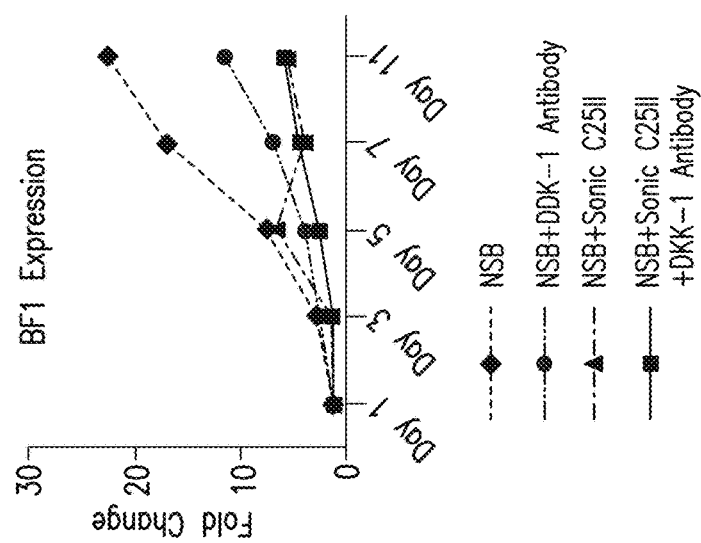
Figure 19J:
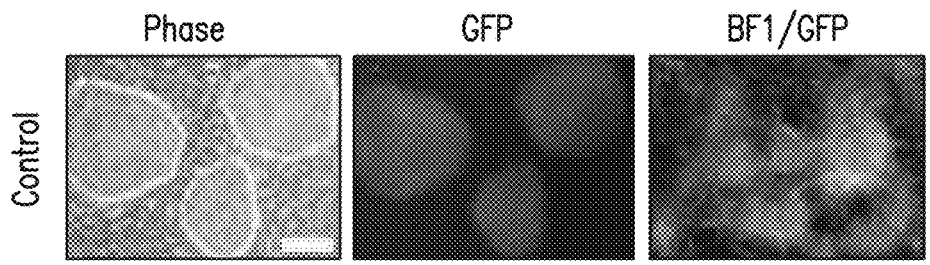
Figure 19K:
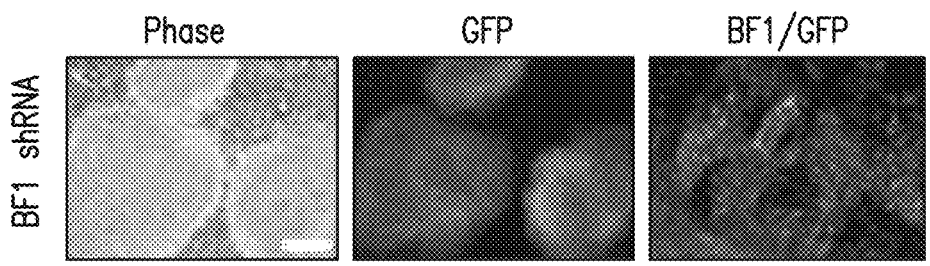
Figure 19L:
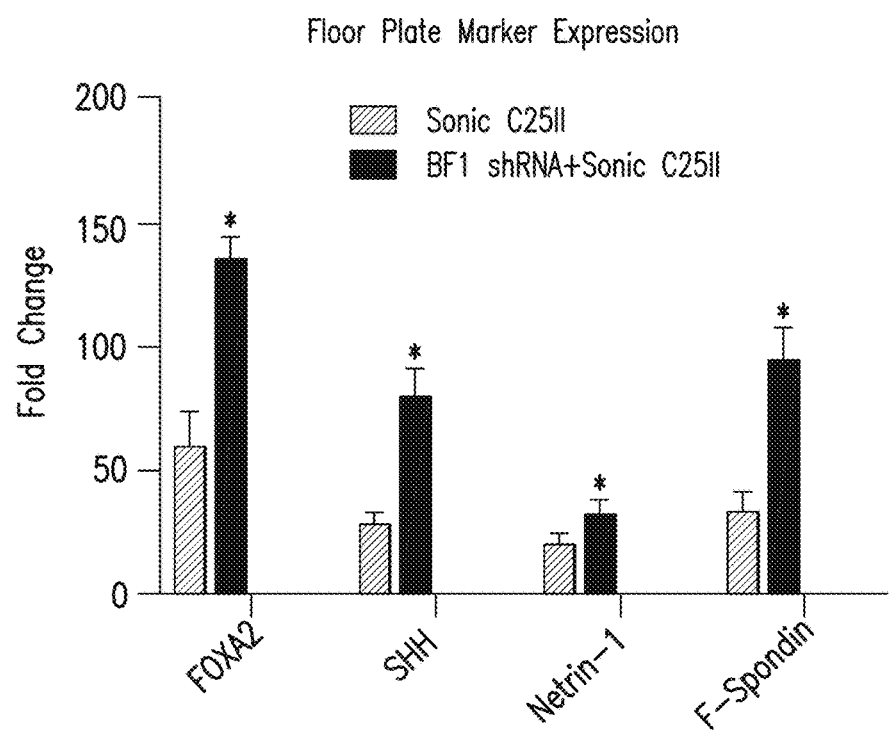
Figure 19M:
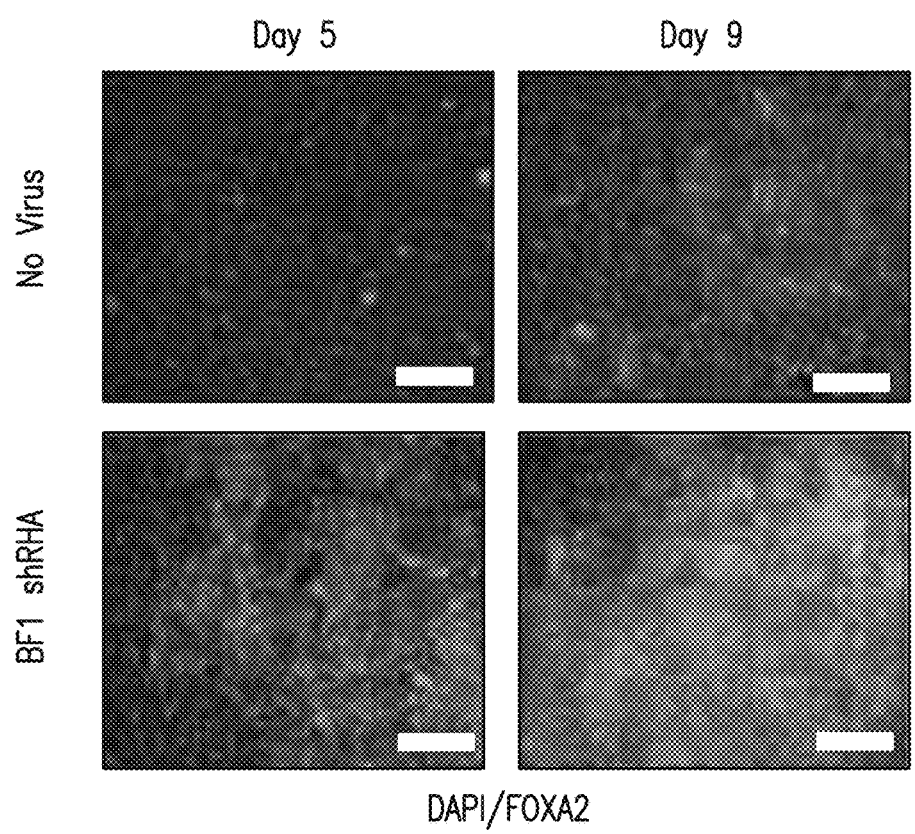

FIG. 18 showing exemplary transcriptional analysis that revealed novel genes involved in FP development. (A-J) qRT-PCR data showing time course of expression over the length of the 11 day protocol. The genes looked at represented different populations including FP markers (A-D), SHH responsive genes (E-G), neural markers (H), AN markers (I and J), and genes involved in mesodermal and endodermal commitment (K and L). (M-R) Detailed time course microarray analysis (M-N) GO terms for Day 7 (M) and Day 11 (N) showing increase or decrease compared to NSB control. FP condition shows enrichment in genes associated with axon guidance and secreted proteins, while showing a decrease in genes associated with anterior neurectoderm development. (O-R) Pair wise comparisons showing genes up and down regulated compared to NSB control condition at Day 3 (O), Day 5 (P), Day 7 (Q), and Day 11 (R).

FIG. 19 showing exemplary DKK-1 inhibition of FP induction. (A) qPCR for DKK-1 expression in control NSB condition over time. (B) ELISA measuring DKK-1 protein levels in the media at Day 5, 7, and 11 showing a decrease in Dkk-1 levels after Sonic C25II treatment, *p<0.05 N=3. (C) qPCR for DKK-1 expression in NSB+Sonic C25II condition over time. (D and E) qPCR for BF1 (D) and FOXA2 (E) showing an increase in BF1 and decrease of FOXA2 after DKK-1 addition, and an increase in FOXA2 when DKK-1 antibody is added. (F) Immunostaining for FOXA2 showing a decrease in FOXA2+ cells when DKK-1 is added. Scale bar, 200 µm. (G) qPCR for BF1 expression showing that DKK-1 antibody treatment leads to a decreased expression at earlier time points (Day 3-Day 5). (H and 1) Early addition of DKK-1 antibody leads to an increase of FOXA2 expression, but has no effect when added at later timepoints. (I) Immunocytochemical data demonstrating that Dkk-1 treatment starting at day 5 of differentiation (or later) does not enhance SHH-mediated FOXA2 expression.

(J-K") hESC transduced with either control or BF1 shRNA (J and K), GFP is a marker of transduction (A' and B'). When differentiated to neural tissue, a reduction of BF1 is seen at the level of the protein compared to control (J" and K"). Scale bars, A and B 100 µm, J" and K" 200 µm. (L) qRT-PCR analysis at Day 11 showed an increase in FP markers (FOXA2, SHH, Netrin-1 and F-Spondin) in the BF1 shRNA line compared to the control, p<0.01 N=3. (M) BF1 shRNA leads to an upregulation of FOXA2 seen at the level of the protein. Scale bar, 200 µm.

Figure 20D:
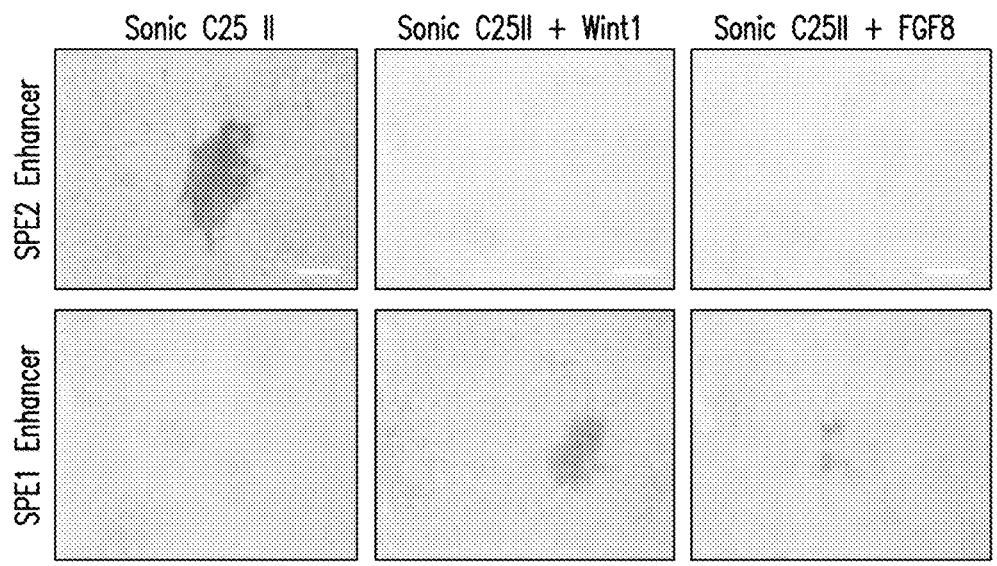
Figure 20E:
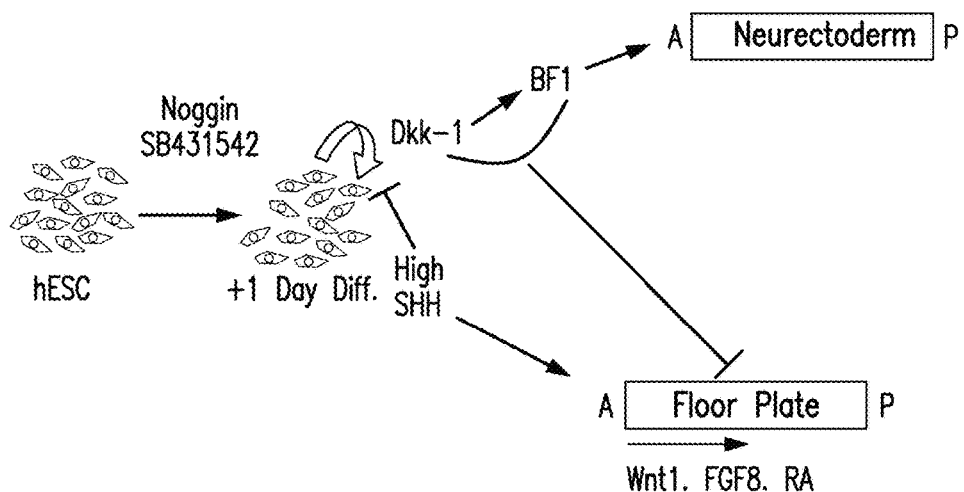

FIG. 20 showing exemplary hESC derived FP was shifted along the A/P axis (A) Immunostaining reveals an increase in FOXA2 in response to FGF8, Writ-1, and Retinoic Acid. Scale bar, 200 µm. (B) qPCR showing caudilizing agents such as FGF8, Wnt-1, and Retinoic Acid (RA) lead to an increase in FOXA2 and a reduction in SIX6 compared to NSB+Sonic C25II. (C) qPCR for a panel of midbrain FP markers (CORIN and NOV) and midbrain DA progenitor markers (LMX1B, NGN2, and EN1). In particular, Wnt-1 treatment causes an upregulation of both midbrain FP markers as well as midbrain DA progenitor markers. (D) FP cells were transfected with Shh enhancer that drives expression to the anterior ventral axis (SBE2) or midbrain ventral axis (SBE1). The default FP exhibits SBE2 activity indicating an anterior location. This is abolished upon Wnt1 and FGF8 addition and SBE1 activity is now seen suggesting a shift from anterior identity to midbrain. Scale bar, 200 µm. (E) Schematic of FP versus AN specification during hESC differentiation. Neural differentiation is initiated upon exposure to Noggin and SB431542. SHH exposure, starting at day 1 of differentiation, induces FP differentiation and via inhibition of DKK-1 and BF1 suppresses AN specification. The regional identity of the resulting FP cells is anterior by default but posterior FP tissue were induced in the presence of caudalizing factors such as Wnt-1, FGFF8 or RA.

Figure 21:
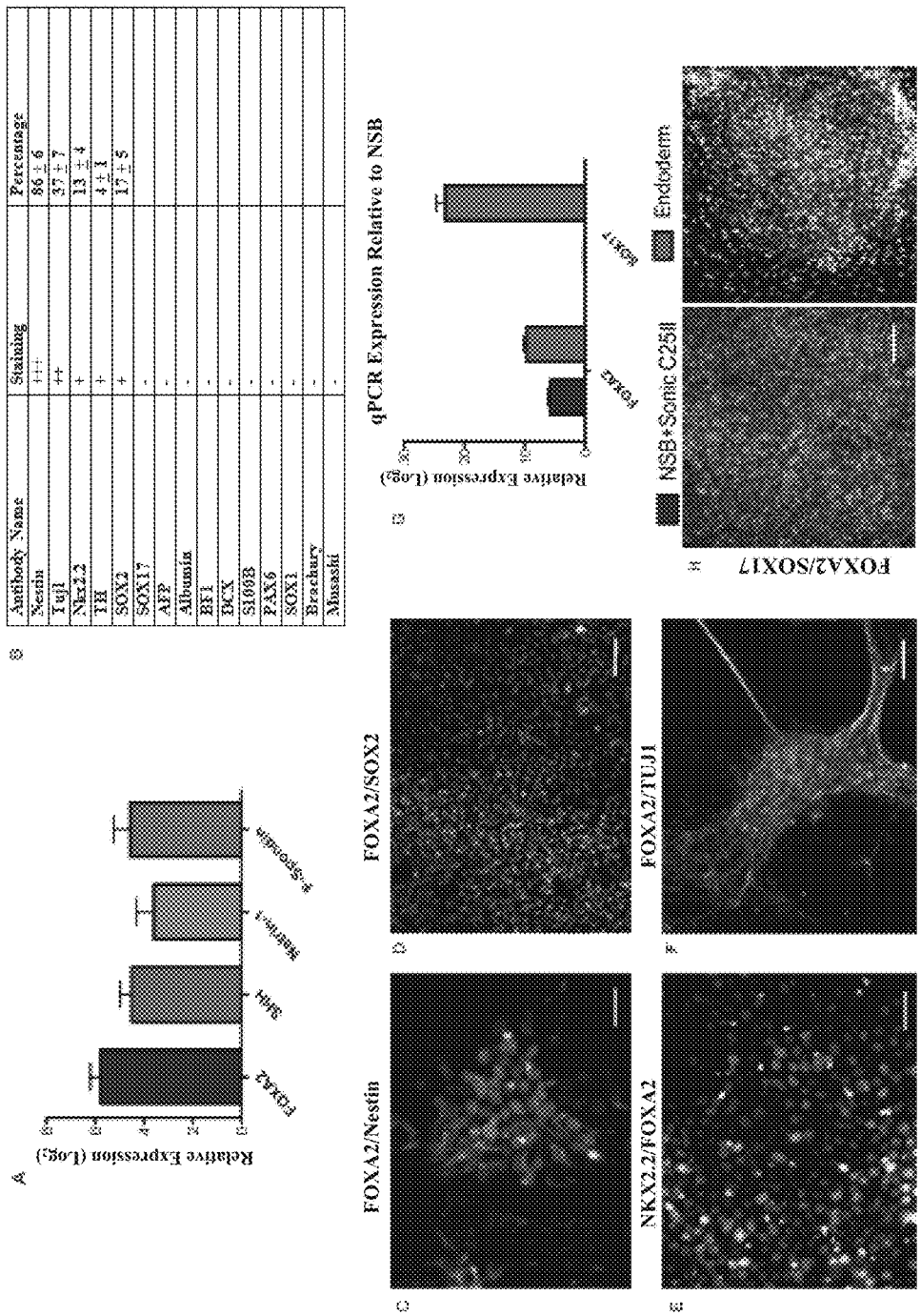

FIG. 21 showing exemplary hESC derived FP expresses the appropriate markers (A) qRT-PCR data at Day 11 showing an increase in floor plate markers FOXA2, SHH, Netrin-1, and F-Spondin relative to control NSB conditions. (13) Table quantifying results of immunostaining experiments. (C-F) Immunostaining of FOXA2+ cells reveals co-labelling with few markers such as (C) Nestin, (D) SOX2, (E) Nkx2.2, and (F) Tuj1. Scale bar, (D and F, 50 µm) (E and G, 100 µm). (G-H) qRT-PCR data at Day 11 showing levels of FOXA2 and SOX17 cells differentiated with NSB+ Sonic C25II treatment and cells differentiated towards an endodermal lineage. SOX17 is not expressed in Sonic C25II conditions but is highly expressed in the endoderm. This is shown at the level of the protein by immunostaining (H). Scale bar, 200 µm.

Figure 22:
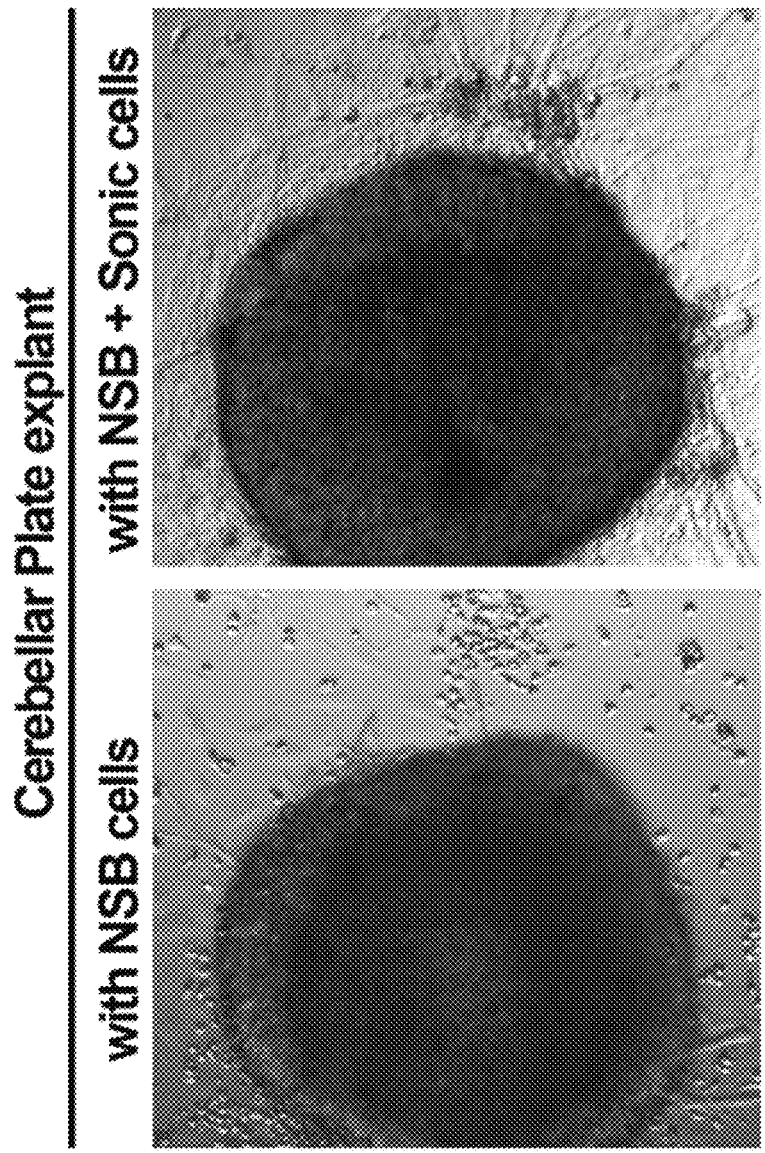

FIG. 22 showing exemplary co-culture of cerebellar plate explants on FP cells induces neurite outgrowth. Cerebellar explants from E8.5 mouse were plated on NSB neural cells or NSB+Sonic (FP) cells. After 3 days considerable neurite outgrowth was observed in the NSB+Sonic (FP) condition compared to control.

Figure 23:
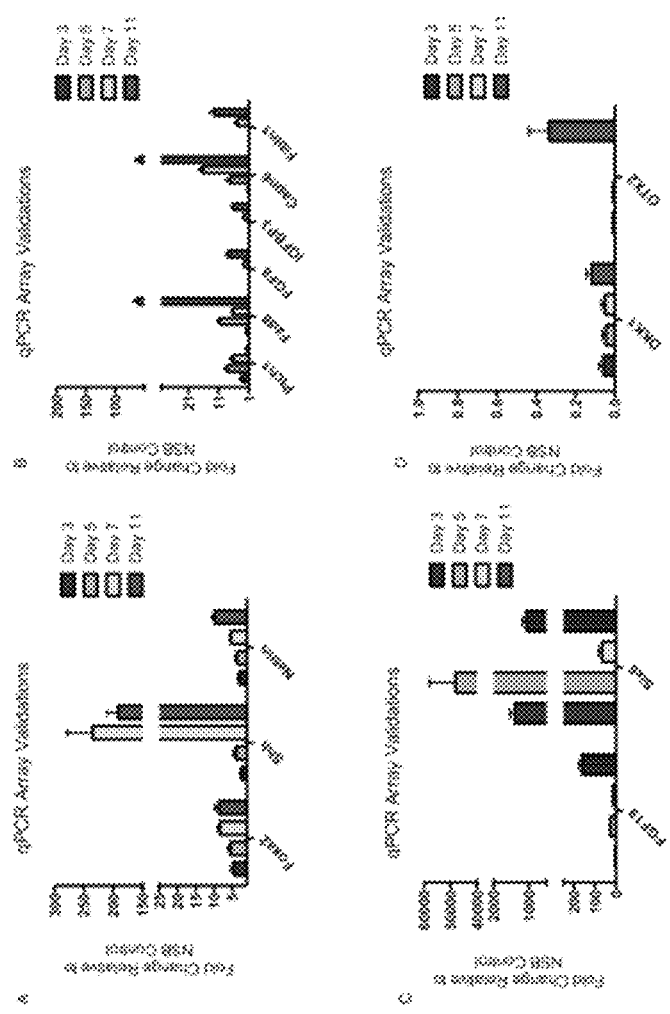

FIG. 23 showing exemplary qPCR validates genes changing in microarray. (A) qPCR for FP genes showing an enrichment in Sonic C25II condition compared to NSB control. (B-D) qPCR validating novel genes that changes in the Sonic C25II condition compared to NSB control condition.

Figure 24:
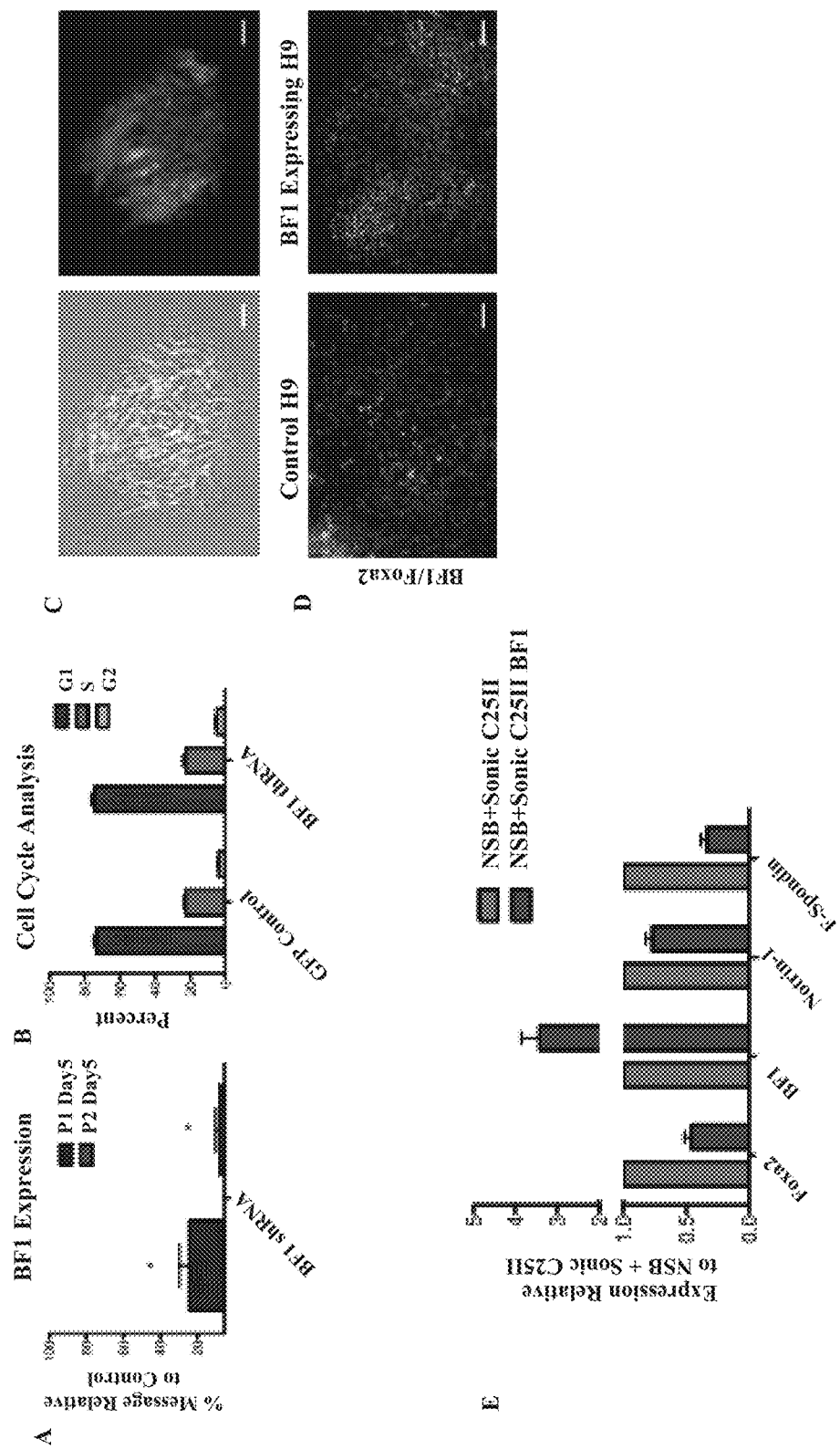

FIG. 24 showing exemplary BF1 expression inhibits FP induction (A) qRT-PCR at two points during neural differentiation showing a decrease in BF1 levels in the BF shRNA hESC line compared to control, *p<0.01 N=3. (B) Cell cycle analysis revealed no differences in the cell cycle kinetics of the two lines. (C) hESC expressing BF1 visualized by GFP. Scale bar, 20 µm. (D) Cells overexpressing BF lack FOXA2+ expression. Scale bar, 200 µm. (E) qRT-PCR data at Day 11 showing a lack of FP induction in BF1 expressing hESC after Sonic C25II treatment.

Figure 25:
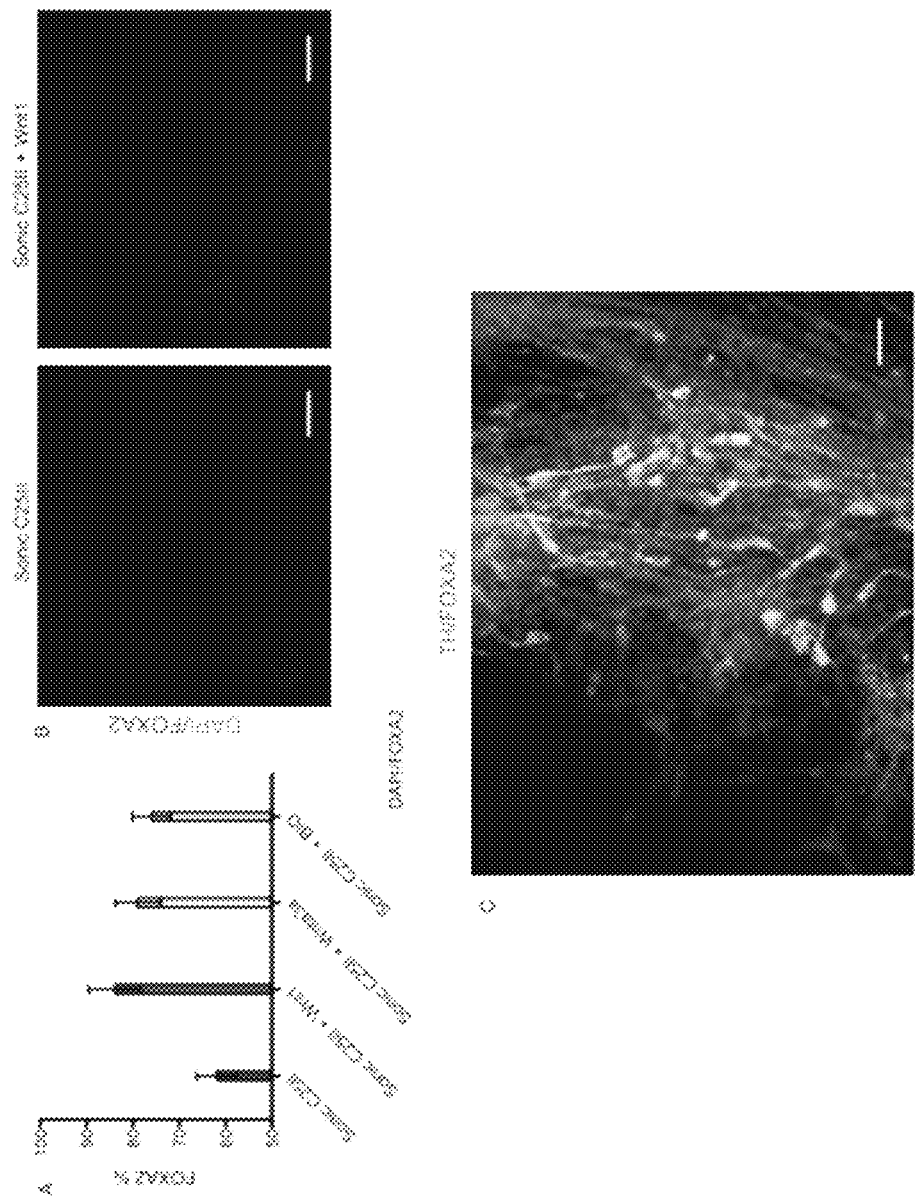

FIG. 25 showing exemplary early WNT1 addition along FP differentiation can cause DA neuron differentiation (A) Adding WNTs or GSK3β-Inhibitor (BIO 100 nM) early can increase FOXA2 expression. (B) Addition of WNT1 to later stage neural rosette cells has no effect on FOXA2 induction, scale bar 200 µm. (C) WNT1 treated FP cultures can give rise to DA Neurons expressing FOXA2, scale bar 50 µm.

Figure 26:
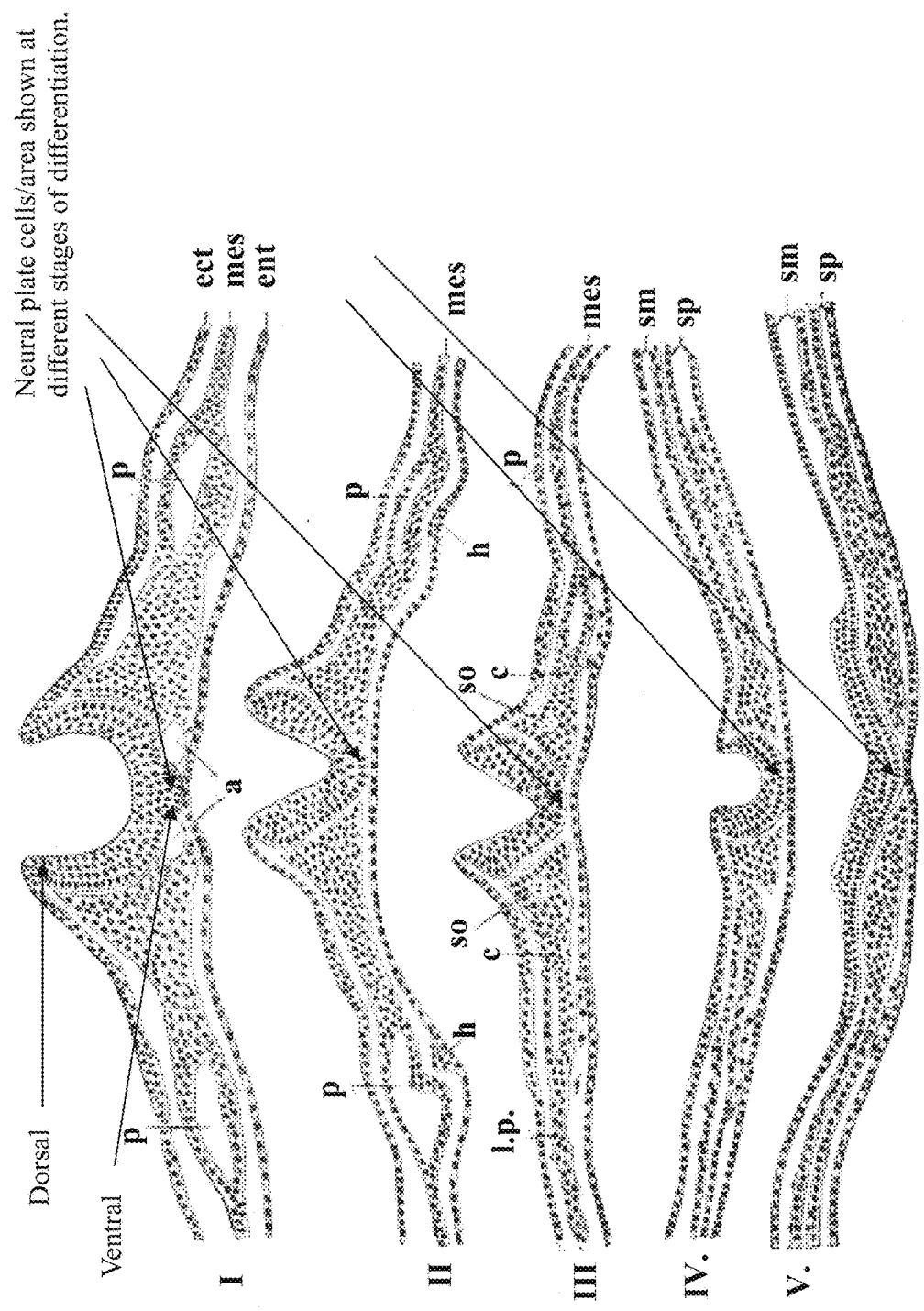

FIG. 26 Gray's Anatomy plate|A: series of transverse sections through an embryo of the dog, anterior to posterior, I-V. Section I is the most anterior. In V the neural plate is spread out nearly flat. Gray's Anatomy by Henry Gray.

DEFINITIONS

As used herein, the term "inhibitor" in reference to inhibiting a signaling target or a signaling target pathway refers to a compound that interferes with (i.e. reduces or eliminates or suppresses) a resulting target molecule or target compound or target process, such as a particular differentiation outcome, (for example, suppresses an active signaling pathway promoting a default cell type differentiation, thereby inducing differentiation into a non-default cell type) when compared to an untreated cell or a cell treated with a compound that does not inhibit a treated cell or tissue.

As used herein, the term "Small Mothers Against Decapentaplegic" or "SMAD" refers to a signaling molecule.

As used herein, the term "neural cell" or "neuronal cell" refers to a cell that in vivo would become part of the nervous system and in culture is obtained by methods of the present inventions, for example, CNS progenitor cells, patternable (i.e. a cell capable of undergoing further differentiation) neuronal populations of motorneurons and dopaminergic neurons, placodal precursor cells, high efficiency motor neuron cells, etc.

As used herein, the term "high efficiency motor neuron cell" refers to a neuronal cell capable of conducting an electric current.

As used herein, the term "fate" in reference to a cell, such as "cell fate determination" in general refers to a cell with a genetically determined lineage whose progeny cells are capable of becoming a variety of cell types or a few specific cell types depending upon in vivo or in vitro culture conditions. In other words, a cell's predetermined fate is determined by it's environment to be destined for a particular differentiation pathway such that a cell becomes one cell type instead of another cell type, for example, a stem cell's progeny cells whose "neural fate" is to become a nerve cell instead of a muscle cell or a skin cell. Typically, a cell's "fate" is irreversible except under highly specific conditions. In another example, a "CNS fate" refers to a cell capable of becoming a cell associated with the central nervous system. Conversely, a cell fated to become a neural cell can be called a "neural progenitor cell."

As used herein, the term "neural progenitor cell" refers to a cell capable of forming a part of the nervous system, such as a nerve cell, a glial cell, etc.

As used herein, the term "neuronal subtype" refers to any cell of the neuronal system, such as a dopamine expression neuron, a peripherin+neuron, a motor neuron cell, etc.

As used herein, the term "cell of a neural lineage" refers to a cell that differentiated along a neural precursor pathway.

As used herein, the term "placode" in reference to a cell refers to a cell capable of becoming a cell associated with the sensory nervous system. In one embodiment, a placode cell is positive for Six1+, positive for p75 while negative for HNK1. In one embodiment, a placode cell obtained using methods of the present inventions is capable of forming a lens cell.

As used herein, the term "adenohypophyseal precursor" in reference to a cell refers to a cell whose in vivo progeny cells would be or become a part of the pituitary gland. An adenohypophyseal precursor cell of the present inventions refers to a cell capable of expressing Lhx3 and CGA.

As used herein, the term "expressing" in relation to a gene or protein refers to making an mRNA or protein which can be observed using assays such as microarray assays, antibody staining assays, and the like.

As used herein, the term "inhibitor" in reference to inhibiting a signaling molecule or a signaling molecule's pathway, such as an inhibitor of SMAD signaling, refers to a compound that interferes with (i.e. reduces or eliminates or suppresses) the signaling function of the molecule or pathway. In one embodiment, an inhibitor of the present inventions induces (changes) or alters differentiation from a default to a non-default cell type, for example, one of the methods of the present inventions comprising two inhibitors of SMAD signaling produces a non-default neural progenitor cell.

As used herein, the term "Small Mothers Against Decapentaplegic" or "SMAD" refers to a signaling molecule.

As used herein, the term "cell differentiation" refers to a pathway by which a less specialized cell (i.e. stem cell) develops or matures to possess a more distinct form and function (i.e. neural plate).

As used herein, the term "differentiation" as used with respect to cells in a differentiating cell system refers to the process by which cells differentiate from one cell type (e.g., a multipotent, totipotent or pluripotent differentiable cell) to another cell type such as a target differentiated cell.

As used herein, the term "cell differentiation" in reference to a pathway refers to a process by which a less specialized cell (i.e. stem cell) develops or matures or differentiates to possess a more distinct form and/or function into a more specialized cell or differentiated cell, (i.e. neural cell, neural plate cell, pituitary cell, adrenal cell, etc.).

As used herein, the term "neural stem cell" or "NSC" refers to a cell that is capable of becoming neurons, astrocytes, oligodendrocytes, glial cells, etc., in vivo, and neuronal cell progeny and glial progeny in culture however their in vitro differentiation potential toward multiple region-specific neuron types is low.

As used herein, the term "default" or "passive" in reference to a cell differentiation pathway refers to a pathway where a less specialized cell becomes a certain differentiated cell type in culture, when not treating with certain compounds i.e. normal cell cultures conditions. In other words, a default cell results when a cell is not contacted by a molecule capable of changing the differentiated cell type (i.e. a morphogen). In contrast, "non-default" in reference to a cell refers to a differentiated cell type that results that is different from a default cell, i.e. a non-default cell is a differentiated cell type resulting from a non-default conditions, such as cell of the present inventions, including a dopamine positive nerve cell, a floor plate cell, posterior FP tissue, etc. A default cell may also be a default cell after a cell has contact with a morphogen to become a non-default cell without a subsequent morphogenic compound, such as a non-default floor plate cell that subsequently becomes a default posterior FP cell of the non-default cell of the present inventions.

As used herein, the term "homodimer" in reference to a SMAD molecule refers to at least two molecules of SMAD linked together, such as by disulfide linkages.

As used herein, the term "Noggin" refers a secreted homodimeric glycoprotein that binds to and inactivates members of the transforming growth factor-beta (TGF-β) superfamily of signaling proteins, such as bone morphogenetic protein-4 (BMP4). Noggin is typically a 65 kDa protein expressed in human cells as a glycosylated, disulfide-linked dimer. (Groppe, et al., (2002). Nature 420, 636-642; Xu, et al., (2005) Nat Methods 2, 185-190; Wang, et al., (2005) Biochem Biophys Res Commun 330, 934-942). One example of a Noggin amino acid sequence is: Accession #U79163 single amino acid mouse Noggin (SEQ ID NO:1):

MERCPSLGVTLYALVVVLGLRAAPAGGQHYLHIRPAPSDNLPLVDFTLIE

HPDPIFDPKEKDLNETLLRSLLGGHYDPGFMATSPPEDRPGGGGPAGGA

-continued
EDLAELFTDQLLRQRPSGAMPSEIKGLEFSEGLAQGKKQRLSKKLRRKLQ

MWLWSQTFCPVLYAWNDFTLGSRFWPRYVKVGSCFSKRSCSVPEGMVCKP

SKSVHLTVLRWRCQRRGGQRCGWIPIQYFTPIISECKCSC.

As used herein, the term "SB431542" refers to a molecule with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

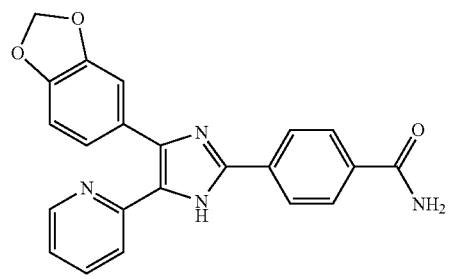 [SMILES: NC(=O)c1ccc(-c2nc(-c3ccc4c(c3)OCO4)c(-c3ccccn3)[nH]2)cc1]

As used herein, the term "Dorsomorphin" refers to a molecule with a number CAS 866405-64-3, a molecular formula $C_{24}H_{25}N_5O$ and a name of 6-[4-[2-(1-Piperidinyl) ethoxy]phenyl]-3-(4-pyridinyl)-pyrazolo[1,5-a]pyrimidine dihydrochloride, for example see structure below.

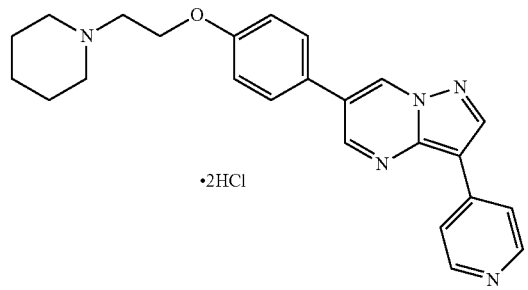 [SMILES: c1cc(-c2cnn3cc(-c4ccc(OCCN5CCCCC5)cc4)cnc23)ccn1]

As used herein, the term "Lefty" refers to a novel member of the transforming growth factor beta superfamily that inhibits TGF-beta, including but not limited to LEFTY1, LEFTY2, LEFTYA, etc., also known as "EBAF" or "endometrial bleeding associated factor" or "left-right determination, factor A" transforming growth factor beta superfamily)). A Lefty protein is required for left-right asymmetry determination of organ systems in mammals.

As used herein, the term "Activin" refers to a member of the transforming growth factor-beta (TGF-β) superfamily, such as Activin A, Activin B, etc.

As used herein, the term "transforming growth factor beta" or "TGF-β" refers to a cytokine that regulates growth and differentiation of diverse types of cells.

As used herein, the term "nodal" refers to a member of the TGF-β family of signaling molecules. Nodal signaling inhibits differentiation of human embryonic stem cells along the neuroectodermal default pathway (Vallier, et al., Dev. Biol. 275, 403-421.

As used herein, the term "ALK" or "anaplastic lymphoma kinase" or "anaplastic lymphoma receptor tyrosine kinase" or "Ki-1" refers to a membrane associated tyrosine kinase receptor.

As used herein, the term "ALK4" in reference to a type I serine/threonine kinase receptor refer as to an anaplastic lymphoma receptor tyrosine kinase 4 receptor that binds to activin to function as an activin receptor.

As used herein, the term "ALK5" in reference to a type I serine/threonine kinase receptor refer as to an anaplastic lymphoma receptor tyrosine kinase 5 receptor that binds to TGF-β1 to function as a TGF-β1 receptor.

As used herein, the term "ALK7" in reference to a type I serine/threonine kinase receptor refer as to an anaplastic lymphoma receptor tyrosine kinase 7 receptor that binds to Nodal and Nodal-related proteins to function as a Nodal and Nodal-related protein receptor.

As used herein, the term "paired box gene 6" or "PAX6" refers to a marker of a nondefault neuroprogenitor cell.

As used herein, the term "kit" refers to any delivery system for delivering materials. In the context of cell differentiation, a kit may refer to a combination of materials for contacting stem cells, such delivery systems include systems that allow for the storage, transport, or delivery of reaction reagents (e.g., compounds, proteins, detection agents (such as PAX6 antibodies), etc. in the appropriate containers (such as tubes, etc.) and/or supporting materials (e.g., buffers, written instructions for performing cell differentiation, etc.) from one location to another. For example, kits include one or more enclosures (e.g., boxes, or bags, and the like) containing the relevant reaction reagents (such as Noggin (or a Noggin substitute) and SB431542 (or a SB431542 replacement), etc.) and/or supporting materials.

As used herein, the term "inducing differentiation" in reference to a cell refers to changing the default cell type (genotype and/or phenotype) to a non-default cell type (genotype and/or phenotype). Thus "inducing differentiation in a stem cell" refers to inducing the cell to divide into progeny cells with characteristics that are different from the stem cell, such as genotype (i.e. change in gene expression as determined by genetic analysis such as a microarray) and/or phenotype (i.e. change in expression of a protein, such as PAX6 or a set of proteins, such as HMB45 positive (+) while negative (−) for SOX10.

As used herein, the term "contacting" cells with a compound of the present inventions refers to placing the compound in a location that will allow it to touch the cell in order to produce "contacted" cells. The contacting may be accomplished using any suitable method. For example, in one embodiment, contacting is by adding the compound to a tube of cells. Contacting may also be accomplished by adding the compound to a culture of the cells.

As used herein, the term "stem cell" refers to a cell that is totipotent or pluripotent or multipotent and are capable of differentiating into one or more different cell types, such as embryonic stems cells, stem cells isolated from organs, for example, skin stem cells.

As used herein, the term "embryonic stem cell" refers to a cell of a stem cell line, such as WA-09, or a cell isolated from an embryo or placenta or umbilical cord.

As used herein, the term "adult stem cell" refers to a stem cell derived from an organism after birth.

As used herein, the term "neural stem cell" or "NSC" refers to a cell that is capable of becoming neurons, astrocytes, oligodendrocytes, and glial cells in vivo, and neuronal cell progeny and glial progeny in culture however their in vitro differentiation potential toward multiple region-specific neuron types is low.

As used herein, the term "mesodermal cell line" refers to a cell line displaying characteristics associated with mesodermal cells.

As used herein, the term "endodermal cell line" refers to a cell line displaying characteristics normally associated with endodermal cells.

As used herein, the term "neural cell line" refers to a cell line displaying characteristics normally associated with a neural cell. Examples of such characteristics include, but are not limited to, expression of FOXA2, SHH, Netrin-1, F-Spondin, and the like.

As used herein, the term "totipotent" refers to an ability of a cell to differentiate into any type of cell in a differentiated organism, as well as a cell of extra embryonic materials, such as placenta, etc.

As used herein, the term "pluripotent" refers to a cell line capable of differentiating into any differentiated cell type.

As used herein, the term "multipotent" refers to a cell line capable of differentiating into at least two differentiated cell types.

As used herein, the term "differentiation" as used with respect to cells in a differentiating cell system refers to the process by which cells differentiate from one cell type (e.g., a multipotent, totipotent or pluripotent differentiable cell) to another cell type such as a target differentiated cell.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "neural plate" or "medullary plate" refers to a thickened band of ectoderm (an unpaired ventral longitudinal zone of the neural tube) in the midbody region of the developing embryo, which develops (differentiates) into the neural tube and neural crest; see, FIG. 12. During embryonic development neural plate cells undergo a series of developmental stages and subsequently develop into cells forming a brain, spinal cord, and other tissues of the central nervous system.

As used herein, the term "floor plate" or "FP" or "ventral plate" or "basal plate" or "neural floor plate" refers to an area of cells that develops at the midline of the neural plate and is located at the ventral midline of the neural tube, see, FIG. 12.

As used herein, the term "neural floor plate cell" or "FP cell" or "floor plate cell" in reference to a cell refers to a cell group also called "specialized neuroepithelial cells" found in a developing embryo in the neural floor plate. FP cell in vitro are cells expressing certain cell markers also found in FP cells in vivo that are not found in other cells.

As used herein, the term "roof plate" or "alar plate" or "dorsal roof plate" refers to a cell group located in at the dorsal region of the fruiting and formed neural tube areas the unpaired dorsal longitudinal zone of the neural tube.

As used herein, the term "neural tube" refers to a hollow cylindrical structure of neuroepithelial cells formed from the neuroectoderm cells of an early embryo by the closure of the neural groove such that neuroectoderm cells can differentiate into brain cells and spinal cord cells.

As used herein, the term "presumptive" or "progenitor" in reference to a cell or an area of cells refers to the type of cell or area of cells that would develop (differentiate into) under the appropriate conditions, i.e. when contacted with a proper growth factor, compound, extracellular signal, intracellular signal, etc. For example, "progenitor neuron" refers to a cell that has the capability to develop into a neuron.

As used herein, the term "dopamine neuron" or "dopaminergic neuron" in general refers to a cell capable of expressing dopamine. "Midbrain dopamine neurons" or "mDA" refer to presumptive dopamine expressing cells in forebrain structures and dopamine expressing cells in forebrain structures.

As used herein, the term "default" in reference to a cell differentiation pathway refers to a pathway where a less specialized cell becomes a certain differentiated cell type when not contacted by a molecule which changes the differentiated cell type.

As used herein, the term "cell differentiation" refers to a pathway by which a less specialized cell (i.e. stem cell) develops or matures to possess a more distinct form and function (i.e. neural plate).

As used herein, the term "neurite outgrowth" refers to observation of elongated, membrane-enclosed protrusions of cytoplasm from cells.

As used herein, the term "attached cell" refers to a cell growing in vitro wherein the cell contacts the bottom or side of the culture dish, an attached cell may contact the dish via extracellular matrix molecules and the like. As opposed to a cell in a suspension culture.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type. For example, FP cells of the present inventions express one or more markers that distinguish a FP cell, i.e. FOXA2 positive and BF1 negative, from a nonFP cell, i.e. FOXA2 negative and BF1 positive.

As used herein, the term "test compound" refers to any chemical entity, pharmaceutical, drug, and the like that were used to provide cells of the present inventions.

As used herein, the term "rosette-stage neural cell" or "R-NSC" refers to a neural stem cell type in vitro with broad differentiation potential capable of forming central nervous system (CNS) and peripheral nervous system (PNS) cells (fates) and capable of in vivo engraftment. In other words, a rosette-stage neural cell is capable of forming a rosette structure and rosette-stage neural cell populations have characteristics of neuronal differentiation.

As used herein, the term "rosette structure" or "rosette" in reference to a cell refers to a halo or spoke-wheel arrangement of cells.

As used herein, the term "increasing" in reference to a characteristic refers to a larger amount of a characteristic when compared to said characteristic in a control, such as when comparing an amount of a marker in human embryonic stems cells cultured with and without a test compound.

As used herein, the term "decreasing" in reference to a characteristic refers to a smaller amount of a characteristic when compared to said characteristic in a control, such as when comparing an amount of a marker in human embryonic stems cells cultured with and without a test compound.

As used herein, the term "reducing protein function" or "loss of function" refers to interfering with or blocking a function in order to lower that function, for example, lowering the function of DKK-1 by blocking antibodies.

As used herein, the term "neuron inducing compound" refers to a substance for causing differentiation along a cellular pathway leading to neuronal cell.

As used herein, the term "agent for blocking phosphorylation of a receptor" refers to a substance for reducing receptor function, i.e. by reducing phosphorylation. As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a cell or tissue. In another sense, it is meant to include a specimen or culture obtained from any source and encompass fluids, solids and tissues. Environmental samples include environmental material such as surface matter, soil, water, and industrial samples. These examples are not to be construed as limiting the sample types applicable to the present invention.

The terms "purified," "to purify," "purification," "isolated," "to isolate," "isolation," and grammatical equivalents thereof as used herein, refer to the reduction in the amount of at least one contaminant from a sample. For example, a cell type is purified by at least a 10%, preferably by at least 30%, more preferably by at least 50%, yet more preferably by at least 75%, and most preferably by at least 90%, reduction in the amount of undesirable cell types, such as isolated differentiated FP cells from nonFP cells, such as cells present in a mixed cell culture. Thus purification of a cell type results in an "enrichment," i.e., an increase in the amount, of the nucleotide sequence in the sample.

The term "naturally occurring" as used herein when applied to an object (such as cell, tissue, etc.) and/or chemical (such as a protein, amino acid sequence, nucleic acid sequence, codon, etc.) means that the object and/or compound are/were found in nature. For example, a naturally occurring cell refers to a cell that is present in an organism that can be isolated from a source in nature, such as an embryonic cell, wherein the cell has not been intentionally modified by man in the laboratory.

As used herein the term, "in vitro" refers to an artificial environment and to processes or reactions that occur within an artificial environment. In vitro environments exemplified, but are not limited to, test tubes and cell cultures.

As used herein the term, "in vivo" refers to the natural environment (e.g., an animal or a cell) and to processes or reactions that occur within a natural environment, such as embryonic development, cell differentiation, neural tube formation, etc.

As used herein, the term "proliferation" refers to an increase in cell number.

As used herein, the term "ligand" refers to a molecule that binds to a second molecule. A particular molecule may be referred to as either, or both, a ligand and second molecule. Examples of second molecules include a receptor of the ligand, and an antibody that binds to the ligand.

The term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vivo, treatment and/or mutagenesis using for example proteins, chemicals, radiation, infection with virus, transfection with DNA sequences, such as with a morphagen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

As used herein, the term "biologically active," refers to a molecule (e.g. peptide, nucleic acid sequence, carbohydrate molecule, organic or inorganic molecule, and the like) having structured, regulatory, and/or biochemical functions.

As used herein, the term "primary cell" is a cell that is directly obtained from a tissue (e.g. blood) or organ of an animal in the absence of culture. Typically, though not necessarily, a primary cell is capable of undergoing ten or fewer passages in vitro before senescence and/or cessation of proliferation. In contrast, a "cultured cell" is a cell that has been maintained and/or propagated in vitro for ten or more passages.

As used herein, the term "cultured cells" refer to cells that are capable of a greater number of passages in vitro before cessation of proliferation and/or senescence when compared to primary cells from the same source. Cultured cells include "cell lines" and "primary cultured cells."

As used herein, the term "cell culture" refers to any in vitro culture of cells. Included within this term are continuous cell lines (e.g. with an immortal phenotype), primary cell cultures, finite cell lines (e.g., non-transformed cells), and any other cell population maintained in vitro, including embryos and embryonic cells.

As used herein, the term "cell line," refers to cells that are cultured in vitro, including primary cell lines, finite cell lines, continuous cell lines, and transformed cell lines, but does not require, that the cells be capable of an infinite number of passages in culture. Cell lines may be generated spontaneously or by transformation.

As used herein, the terms "primary cell culture," and "primary culture," refer to cell cultures that have been directly obtained from cells in vivo, such as from animal tissue. These cultures may be derived from adults as well as fetal tissue.

As used herein, the terms "monolayer," "monolayer culture," and "monolayer cell culture," refers to a cell that has adhered to a substrate and grow as a layer that is one cell in thickness, in other words, an "attached cell." Monolayers may be grown in any format, including but not limited to flasks, tubes, coverslips (e.g., shell vials), roller bottles, et cetera.

As used herein, the terms "feeder cell layer" or "feeder cell population" refers to a monolayer of cells used to provide attachment molecules and/or growth factors for an adjacent cell, for example, used in co-culture to maintain pluripotent stem cells. As used herein, the terms "suspension" and "suspension culture" refer to cells that survive and proliferate without being attached to a substrate. Suspension cultures are typically produced using hematopoietic cells, transformed cell lines, and cells from malignant tumors.

As used herein, the terms "culture media," and "cell culture media," refer to media that are suitable to support the growth of cells in vitro (i.e., cell cultures, cell lines, etc.). It is not intended that the term be limited to any particular culture medium. For example, it is intended that the definition encompass outgrowth as well as maintenance media. Indeed, it is intended that the term encompass any culture medium suitable for the growth of the cell cultures and cells of interest.

The term, "cell biology" or "cellular biology" refers to the study of a live cell, such as anatomy and function of a cell, for example, a cell's physiological properties, structure, organelles, interactions with their environment, their life cycle, division and death.

As used herein, the term "cell" refers to a single cell as well as to a population of (i.e., more than one) cells. The population may be a pure population comprising one cell type, such as a population of neuronal cells or a population of undifferentiated embryonic cells. Alternatively, the population may comprise more than one cell type, for example a mixed cell population. It is not meant to limit the number of cells in a population, for example, a mixed population of cells may comprise at least one differentiated cell. In one embodiment a mixed population may comprise at least one differentiated. In the present inventions, there is no limit on the number of cell types that a cell population may comprise.

As used herein, the term "positive cell" in relation to a stain refers to a cell that expresses a marker and thus "stains" for that marker in a detectable quantitative and/or qualitative amount above a control or comparative cell. A positive cell may also refer to a cell that stains for a molecule such as FOXA2, et cetera.

As used herein, the term "negative cell," refers to a cell absent detectable signal for a marker, such as a cell failing to stain following contacting with a FOXA2 antibody detection method, et cetera.

As used herein, the tem "caudalization" refers to initiation of posterior pathways of neural development in the dorsalized ectoderm during embronic development, for example, dorsalized ectorderm develops various levels of posterior neural tissues, depending on the extent of caudalization.

As used herein, the term "caudalizing agent" or "caudalizing factor" refers to a compound that induces caudalization, such as Wnt-1 and Retinoic Acid (RA)

As used herein, the terms "reporter gene" or "reporter construct" refer to genetic constructs comprising a nucleic acid encoding a protein that is easily detectable or easily assayable, such as a colored protein, fluorescent protein or enzyme such as beta-galactosidase (lacZ gene).

As used herein, the term "gene targeting" refers the integration of exogenous DNA into the genome of a cell at sites where its expression can be suitably controlled. This integration occurs as a result of homologous recombination.

A "knock-in" approach as used herein refers to the procedure of inserting a desired nucleic acid sequence, such as a sequence encoding a reporter gene, into a specific locus in a host cell via homologous recombination.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

DETAILED DESCRIPTION OF THE INVENTION

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. Specifically, methods are provided for obtaining neural plate floor tissue and floor plate cells including induction of neural plate floor development in hESCs for obtaining dopamine (DA) nerve cells. Further, neural plate floor tissue obtained using methods of the present inventions are contemplated for use in co-cultures with other tissues as inducers for shifting differentiation pathways, i.e. patterning.

Transforming growth factor (TGF-beta) and their family members, including bone morphogenetic proteins (BMPs), Nodal, and activins, are involved in the development and maintenance of various organs, in which stem cells play important roles. The ectoderm germ layer of the embryo gives rise to the neuroectoderm (the central and peripheral nervous system, neural crest cells, and derivatives). Several lines of evidence demonstrate a crucial role for Smad signaling during neural induction. Generally, Smad proteins are downstream of TGF-beta superfamily ligands, and when their specific receptors are activated, they stimulate the phosphorylation of the receptor-regulated Smads (R-Smads: Smad1, Smad2, Smad3, Smad5 and Smad 8, with Smads 2 and 3 specifically activated by activin/nodal and TGF-beta type I receptors and Smads 1, 5, and 8 activated by BMP type I receptors). Two distinct pathways converse on Smad 4.

Elegant studies in frog identified BMP inhibitors including chordin (Sasai, et al., *Cell* 79(5):779 (1994)), follistatin (Hemmati-Brivanlou, et al., *Cell* 77 (2): 283 (1994)), and noggin (Smith, et al., *Cell* 70(5):829 (1992)) as the critical neural inducing factors in the Spearman organizer. Mammalian noggin (Valenzuela, et al., *J Neurosci* 15(9):6077 (1995)) has comparable neural inducing properties, and treatment with recombinant Noggin has been used in several hESC neural induction protocols (Lee, et al., *Stem Cells* 25(8):1931 (2007); Elkabetz, et al., *Genes Dev* 22(2):152 (2008)). More recently, the drug SB431542 was shown to enhance neural induction in an embryoid body (EB) based hESC neural induction protocol (Smith, et al., *Dev Biol* 313(1):107 (2008)). SB431542 inhibits the Lefty/Activin/TGFβ pathways by blocking phosphorylation of ALK4, ALK5, ALK7 receptors. While Noggin or SB431542 treatment improve the efficiency of neural induction, neither treatment alone is sufficient to neurally convert hESCs under defined or adherent conditions.

Efforts to culture stem cells under conditions that are robust and highly repeatable, and minimize opportunities of cross contamination. The efforts towards establishing well-defined media and methods will allow for repeatability and accuracy required for use as a therapeutic agent, and there has been a move to establish media and culture conditions that are free of non-human additives and undefined factors.

Modifications of the cell culture system have been the focus of a number of recent patents. U.S. Pat. No. 7,005,252, herein incorporated by reference, discusses the growth of primate embryonic stem cells in the present of Fibroblast Growth Factor and a feeder cell layer, but in the absence of any animal serum. U.S. Pat. No. 7,297,539, herein incorporated by reference, discusses the growth of pluripotent stem cells utilizing a system containing an extracellular matrix in a Fibroblast Growth Factor containing medium, but without a feeder layer. U.S. Pat. No. 7,211,434, herein incorporated by reference, describes a method for culturing mammalian embryonic stem cells in a serum for free and feeder-layer free media containing leukemia inhibitory factor, another cytokine used to maintain pluripotency. Identification of specific and defined compounds as additives to media to control the fate of embryonic stem cells are the focus of a number of used patents, including U.S. Pat. Nos. 7,332,336, 7,294,510 and 7,252,995, each of which are herein incorporated by reference.

Human stem cells offer great promise for cell-replacement therapies, and recent advances in somatic cell reprogramming to induced pluripotent stem cells (hiPSCs) has opened the door to generating patient-specific cells for regenerative medicine and disease modeling (Takahasi et al, 2007; Kim, et al., Cell, 136(3):411-419 (2009)). However to realize the full potential of these approaches, improved differentiation protocols are required that eliminate the use of undefined factors such as neural-inducing stoma (PAX6 or MS5 cells (Kawasaki et al., 2000; Lee et al 2007)), the heterogeneous nature of EB differentiation of the poor yield of protocols based on selective survival of neural progeny. Understanding and selectively triggering the signaling pathways necessary and sufficient for neural indication in hESCs is a critical goal in this effort.

Neural stem cell progenitors and neural subtypes as derived from stem cells have been the focus of numerous scientific publications and patent applications, but threes disclosures lack the most desirable conditions for controlling stem cell fate including the ability to start with a large number of cells, achieve highly homogenous desired cell fates, and use a feeder-free protocol and under adherent conditions. Shang et al., and Reubinoff, et al., *Nature Biotechnology* 19, 1134-1140 (2001) allow for passive development of neural cell types, but cannot control the neural differentiation.

United States Patent Application Publication No. 20090035285, herein incorporated by reference, teaches methods of producing neural cells, relying on EB and rosette formation. U.S. Pat. No. 6,833,269, herein incorporated by reference, provides differentiation of cells rely on the use of feeder cells and EB formation. U.S. Pat. No. 7,011,828, herein incorporated by reference, and Application Publication No. 2005026747, herein incorporated by reference, teaches and 20060078543, herein incorporated by reference, teach the proliferation of an enrich population of hESCs, which are differentiated to neural progenitor cells, neurons, or glial cells. U.S. Pat. No. 6,887,706, herein incorporated by reference, teaches a method of differentiating heESCs intor neural precursor cells using FGF2, whereby in vitro differentiation was induced by withdrawal of FGF2 and plating on omithine and laminin substrate. U.S. Pat. No. 7,368,115 teaches differentiation of neural stem cells or neural stem cell progeny with pituitary adenylate cyclase-activating polypeptide.

In a review by Erceg et al., Stein Cells. Jan. 27(1): 78-87 (2009), herein incorporated by reference, the author noted that the most important concern of the recently published protocols of stem cell differentiation towards neural lineages is (i) the risk of non-neural cell contamination; (ii) that the use of stem cell lines, Matrigel or conditioned media, including procedures relying on EB formation bears the risk of pathogen cross-transfer. None of the foregoing patents or patent applications teaches the derivatization of homogenous population of neural cell lineage from stem cells under the conditions present in this invention.

The present invention further relates to methods of obtaining populations of neural progenitor cells derived from human embryonic stem cells (hESCs), in particular for obtaining neural plate floor tissue. Specifically, methods of the present inventions induce neural plate floor development in hESCs for obtaining dopamine (DA) nerve cells. Further, neural plate floor tissue obtained using methods of the present inventions are contemplated for use in co-cultures with other tissues as inducers for shifting differentiation pathways, i.e. patterning.

Current neural induction protocols in human ES cells (hESs) rely embryoid body formation, stromal feeder co-culture, or selective survival conditions; each strategy displaying significant drawbacks such as poorly defined culture conditions, protracted differentiation and low yield.

Synergistic action of two inhibitors of SMAD signaling was discovered by the inventors and reported herein. Noggin and SB431542 were discovered to be sufficient for inducing rapid and completed neural conversion of hESCs under adherent culture conditions (dual SMAD inhibition protocol). Temporal fate analysis reveals a transient FGF5+ epiblast-like stage followed by PAX6+ neural cells competent of rosette formation. Initial cell density determines the ratio of CNS versus neural crest progeny. Directed differentiation of huPSCs into midbrain dopamine and spinal motor neurons confirm robustness and general applicability of the novel induction protocol. Noggin/SB4315242 based neural induction should greatly facilitate the use of hESC and hiPSCs in regenerative medicine and disease modeling and obviate the need for stromal feeder or EB-based protocols. Further, this method were adapted to culture systems which may enhance the ease, yield efficiency, speed at which neural cells are derived. This should not be considered limiting and culture with additional molecules or growth factors, or incorporating other methods in the art were considered.

Several lines of evidence demonstrate a crucial role for SMAD signaling during neural induction. While Noggin or SB431542 treatment improve the efficiency of neural induction, neither treatment alone is sufficient to neurally convert hESCs under defined or adherent conditions. Here The inventors set out to test whether combined blockade of SMAD signaling using Noggin and SB431542 is sufficient to achieve full neural conversion and to obviate the need for EB- or stromal-feeder based protocols.

Figure 1:
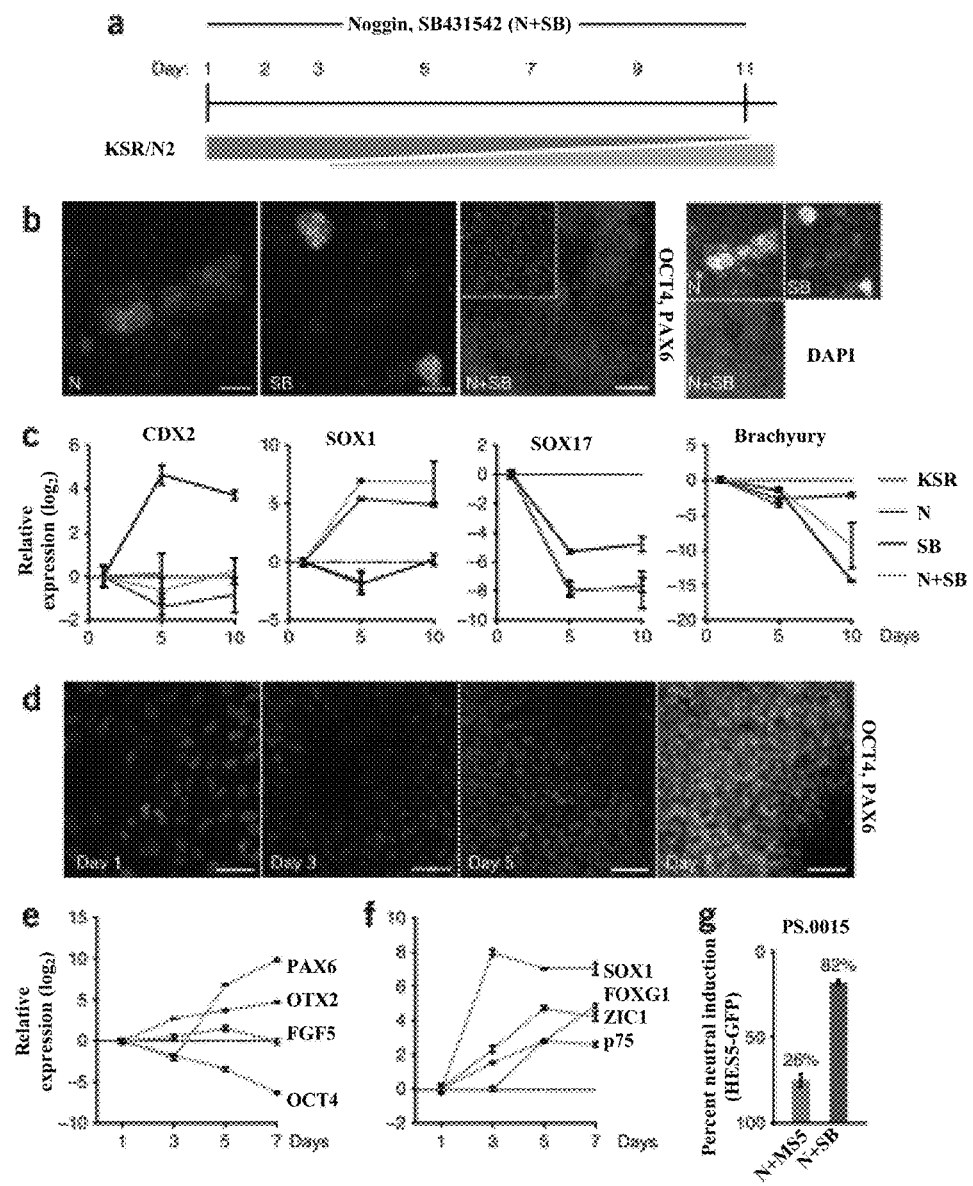
FIG. 1 showing exemplary dual SMAD inhibition that allowed for a highly efficient feeder-free neural induction in adherent cultures within seven days. (a) Differentiation scheme used for achieving neural induction were achieved with the combination of SB431542, an ALK inhibitor, and Noggin, a BMP inhibitor. (b) The dual SMAD inhibition greatly improves neural differentiation (PAX6 expression, green) to greater than 80%. Infrequent neural differentiation (<10% PAX6+ cells) were observed when the single factors are used. (c) Real-Time PCR for early germ layer markers CDX2, SOX1, SOX17 and Brachyury. (d) Immunoflouresence for OCT4 (red) and PAX6 (green) expression indicates rapid neutralization occurs by day 7. (e) Real-Time PCR for PAX6, OTX2, FGF5, OCT4 during dual SMAD inhibition reveals an epistem cell intermediate at day 5. (f) Real-Time PCR for neural and neuronal markers during dual SMAD inhibition differentiation towards neuroectoderm. (g) A BAC reporter line (HES5-GFP) was used to quantify the percentage of neural induction for the method using MS5 stromal cells (with Noggin) or dual SMAD inhibition (SB431542 and Noggin). Error bars represent S.E.M. and the p-value was determined using Student's T-test. Abbreviations: N, Noggin; SB, SB431542; KSR, knock-out serum replacement medium; N2, N2 medium. Scale bars: (b)—200 µm; (d)—50 µm.
Figure 2:
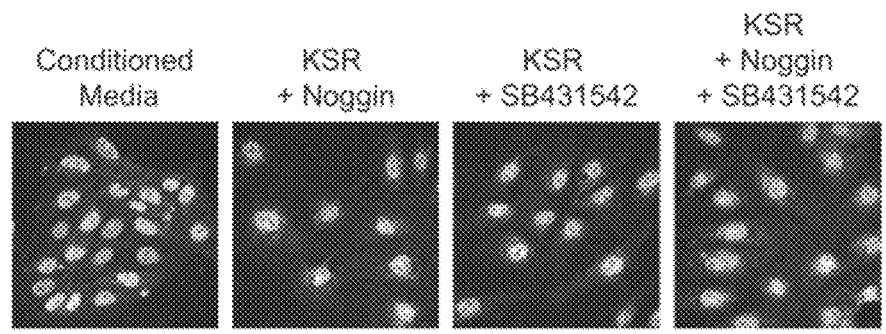
FIG. 2 showing exemplary nuclear localization of SMAD4 diminishes when hESC cells are treated with Noggin and SB43152 for 24 hours. A proportion of SMAD4 redistributes to a perinuclear localization resulting in a less defined cytoplasmic-to-nuclear border.

The inventors contemplated that establishing an even cell distribution is critical for inducing homogenous neural differentiation of hESCs. To this end, undifferentiated hESC were dissociated into single cells and re-plated onto Matrigel coated dishes in conditioned medium supplement with ROCK inhibitor, Y-27632 (Wananabe et al., 2007). After 72 hours cells were switched from hESC conditions to knockout serum replacement medium (KSR) containing either Noggin, SB4315242, or both factors and allowed to differentiate for a total of 11 days (FIG. 1.*a*.). The reduction in nuclear localization of the oblige co-Smad, Smad 4, was observed after 24 hours when both Noggin and SB431542 were present (FIG. 2).Neural induction was monitored by expression of PAX6, an early marker of neuroectodermal differentiation (Callaerts, et al., *Annu Rev Neurosci* 20:483 (1997).

Combined treatment with Noggin and SB431542 dramatically increased the efficiency of neural induction to greater than 80% of total cells, compared with less than 10% PAX6$^+$ cells when Noggin or SB431542 were used alone (FIG. 1*b*). The synergistic action is unexpected, and there are several potential mechanisms that could contribute to the synergistic action of noggin and SB431542. These include destabilizing the activin- and Nanog-mediated pluripotency network (Xu, et al., *Cell Stem Cell* 3(2):196 (2008)), suppression of BMP induced differentiation towards trophoblast lineage (Xu, et al., *Nat Biotechnol* 20(12):1261 (2002)), suppression of mes-/endodermal fates by inhibiting endogenous activin and BMP signals (D'Amou, et al., *Nat Biotechnol* 23(12):1534 (2005)) and promoting neuralization of primitive ectoderm by BMP inhibition (Laflamme, et al., *Nat Biotechnol* 25(9): 1015 (2007)).

Temporal analysis of gene expression revealed that treatment with SB431542 induced a rapid loss of Nanog expression (FIG. 4) and a dramatic increase in the expression of CDX2 (FIG. 1*c*). These data suggested SB431542 mediated loss of pluripotency is associated with differentiation towards trophoblast lineage. Suppression of CDX2 in the presence of Noggin or Noggin/SB431542 demonstrates that one key role of Noggin is the repression of endogenous BMP signals that drive trophoblast fates upon differentiation. The pronounced induction of SOX1 in Noggin/SB431542 treated cultures confirmed a strong bias towards neurectodermal lineage in the dual SMAD inhibition protocol. There is also evidence for suppression of alternative embryonic germ layers such as Noggin-mediated suppression of SOX17 (endodermal lineage) and SB431542 mediated suppression of Brachyury (mesodermal lineage) (FIG. 1c). Taken together, these results indicate that SB431542 and Noggin work synergistically at multiple stages of differentiation to achieve efficient neural conversion of hESCs.

Next lineage progression of hESC progeny after the addition of the two inhibitors was characterized. Immunocytochemical analysis showed loss of OCT4 expression by day 5 and strong expression of PAX 6 by day 7 (FIG. 1d). These data pointed to the presence of an intermediate cell type at day 5 of differentiation that was negative for both OCT4 and PAX6. Gene expression analysis revealed peak expression of the epiblast marker FGF5 at day 5 of differentiation concomitant with high expression of Otx2, another epiblast marker whose expression is maintained during neural fate commitment (FIG. 1e). Interestingly, the earliest neural marker expressed in our culture system was SOX1 (FIG. 1f), preceding induction of other neurepithelial markers such as ZIC1 or PAX6, and preceding expression of anterior CNS (FOXG1) and neural crest (p75) markers. Early induction of SOX1 is distinct from previous studies that had suggested PAX6 expression preceding SOX1 induction (Munoz-Sanjuan, et al., *Nat Rev Neurosci* 3(4):271 (2002)). One interesting possibility to explain this discrepancy could be direct modulation of SOX1 transcription by SMAD signaling in our culture system. Recently methods for were described for establishing stable mouse (Munoz-Sanjuan, et al., *Nat Rev Neurosci* 3(4):271 (2002)) and hESC (Placantonakis, et al., *Stem Cells* 27(3):521-532 (2009)) transgenic reporter lines carrying bacterial artificial chromosomes (BACs) engineered to express GFP under control of cell type specific promoters. Here The inventors used the HES5::eGFP BAC transgenic hESC reporter line, marking neural stem and precursor cell progeny (Tesar, *Nature* 448: 196-199 (2007); (Placantonakis, et al., *Stem Cells* 27(3): 521-532 (2009)), to measure the efficiency of neural induction. The dual SMAD inhibition protocol was compared to the standard MS5 protocol in the presence of Noggin (Perrier, et al., *Proc Natl Acad Sci USA* 101(34):12543 (2004)). To this end HES5::eGFP cells were plated in media supplemented with Noggin either in the presence of MS5 feeder cells or SB431542 and allowed to differentiate for 13 days, a stage when the GFP$^+$ cells were readily observed under both conditions (FIG. 4). GFP expression was quantified by flow cytometry. Non-modified H9 cells were used as negative controls. MS5 cells were excluded from the analysis based on negative selection for the cell surface molecule CD105 (FIG. 5). Dual SMAD inhibition yielded 82% GFP$^+$ cells at day 13, a more than 3 fold increase compared with the MS5/Noggin protocol (FIG. 1f).

In contrast to the MS5 protocol which requires plating of hESC colonies at low density (Li, et al., *Nat Biotechnol* 23(2):215 (2005)), the Noggin/SB431542 condition allowed for high plating densities. Therefore, in addition to higher percentages, the dual SMAD inhibition protocol also resulted in larger absolute numbers of Hes5::eGFP$^+$ cells per each culture plate.

(Isolation of rosette neural stem cells was reported (Elkabetz, et al., *Genes Dev.* 22, 152-165 (2008)) (R-NSCs) in addition to development of neural crest stem cells (Lee, et al., *Stem Cells* 25 (8), 1931 (2007)) (NCSCs) from hESCs. The inventors next sought to determine the lineage relationship of the early PAX6$^+$ neuroectodermal cells observed in the dual SMAD inhibition protocol to the R-NSCs and NCSCs populations described previously. Immunocytochemical analysis showed that, similar to R-NSCs, PAX6$^+$ neuroectodennal cells express general NSC markers such as Nestin and R-NSC markers including PLZF (FIGS. 2a and b; day 11 of differentiation). However, cytoarchitecture and ZO1 expression indicated that neuroepithelial cells under these conditions were non-polarized exhibiting an ESC-like cytoarchitecture. These non-polarized areas were interspersed with R-NSC like areas composed of polarized columnar epithelial cells (FIG. 7c). The developmental hierarchy of these two cell populations was further explored upon subsequent passage. Under these conditions early neuroepithelial cells spontaneously converted into rosette structures with apical ZO1 expression and evidence of interkinetic nuclear migration (FIG. 2d). These data suggested that the Noggin/SB431542 protocol yields an early PAX6$^+$ neuroepithelial population capable of rosette formation. The early PAX6$^+$ cells may therefore represent the most primitive hESC derived neural precursor stage isolated to date. R-NSCs have been shown to acquire anterior CNS marker by default (Elkabetz, et al., *Genes Dev.* 22:152-165 (2008)). PAX6$^+$ neuroepithelial cells generated via the dual SMAD inhibition protocol exhibited an anterior CNS character as evidenced by expression of Otx2 and FoxG1B (FIG. 2e, f) similar to R-NSCs (Elkabetz, et al., *Genes Dev.* 22:152-165 (2008)). Interestingly, PAX6 negative cells under these conditions co-expressed markers of neural crest including AP2, HNK1, PAX7, and p75 (NGFR) (FIG. 2g-j). Manipulations of the initial hESC plating density skewed the ratio of PAX6$^+$ CNS versus PAX6$^-$ neural crest-like cells. High plating densities resulted in near exclusive differentiation towards PAX6$^+$ cells while low densities promoted neural crest-like differentiation (FIG. 6). The presence of large numbers of neural crest-like cells prior to rosette formation suggested that dual SMAD inhibition yields an early neural crest population distinct from R-NSC derived NCSCs (Lee, et al., *Stem Cells* 25(8):1931 (2007)). Supporting the notion of an early neural crest population with distinct lineage potential cells could be readily enriched for pigmented cells co-expresssing the melanosome marker, HMB45 (FIGS. 2k and l, see Examples for details). In contrast, R-NSC derived NCSCs typically do not yield pigmented cells under comparable conditions (Lee, et al., *Stem Cells* 25(8):1931 (2007)). However, some HMB45$^+$ cells did not coexpress the neural crest marker SOX10 suggesting the presence of other pigmented cell populations including PAX6$^+$ retinal pigment epithelial cells.

Anterior-posterior (AP) and dorso-ventral (DV) identity and neuronal subtype potential is dependent on early exposure to morphogenic factors such as retinoic acid, FGF8, and SHH. The inventors next explored the patterning potential of cells generated via the dual SMAD inhibition protocol. The inventors postulated that day 5 of differentiation may present an appropriate developmental window for neural patterning since Oct4 expression is silenced between day 3 and 5 and the neural marker PAX6 is activated in the majority of cells between day 5 and 7 (FIG. 1d, e). Derivation of cells expressing markers of dopamine neurons was observed following exposure to SHH and FGF8 (Tomishima, et al., *Stem Cells* 25 (1), 39 (2007)) starting at day 5 and day 9 of differentiation respectively (FIG. 2m). One week after SHH exposure, both FGF8 and SHH were withdrawn and further differentiated in medium containing BDNF, ascorbic acid, GDNF, TGF-β, and cyclic-AMP (BAGTC (Tomishima, et al., *Stem Cells* 25 (1), 39 (2007)), see FIG. 2m). At day 19 of differentiation neurons a large proportion of Tuj1+ neurons co-expressed tyrosine hydroxylase (TH) (FIG. 2n, o), the rate-limiting enzyme in the synthesis of dopamine. TH+ neurons emerged under these conditions spontaneously even in the absence of cell passaging. However, derivation of more mature TH+ cells with long neural processes was promoted following mechanical isolation and en bloc passage at day 12 of differentiation.

Nuclear expression of the motor neuron markers ISL1 and HB9 was observed two weeks upon exposure to BDNF, ascorbic acid, SHH, and retinoic acid (BASR; day 19 of differentiation) confirming the derivation of somatic type motor neurons (FIG. 2q,r). Motor neuron derivation was limited to cultures passaged at about day 11 of differentiation suggesting reduced patterning response at very high cell densities as observed for hESC derived R-NSCs (Elkabetz, et al., Genes Dev 22 (2), 152 (2008)). These data demonstrate robust patterning response in Noggin/SB431542 treated neural progeny and derivation of relevant neuron subtypes after short differentiation periods (approximately 19 days) compared to 30-50 days when using stromal feeder mediated induction protocols (Lee, et al., Stem Cells 25 (8), 1931 (2007); Tomishima, et al., Stem Cells 25 (1), 39 (2007)).

As an alternative to the specific Smad inhibitors used here, it is possible to block both distinct Smad pathways using alternative inhibitors or mechanisms. Dorsomorphin is a small molecule alternative to Noggin, targeting the same pathway. Concentrations ranged from 10 µM to 30 nM, each individual amount added to 10 µM of SB431542. The efficiency was not as high as used with Noggin/SB431542 based on the percentage of PAX6+ cells, but the ratios a combination of Noggin and dorsomorphin with SB431542 allowed for a 15 fold reduction in the concentration of Noggin necessary to obtain equivalent efficiency and cell viability. The small molecule was more cost efficient than Noggin, and the reduction of price is desirable. It is possible to utilize other molecules as well, although there is currently no known alternative small molecule to SB431542 that blocks the entire range of targets, but this example demonstrates that total Smad cloaked (the two know pathways) can result in robust and synergistic effects that yield a highly homogenous population of neural cells. These alternative methods could also include Smad blockade through mechanism including interfering DNA (to include antisense, siRNA, shRNBA, and standard methods known to the art), or overexpression of a protein that can block, compete or otherwise present Smad 4 function (such as overexpression of Smad 7).

Specific cell fates were tested for their ability to survive, migrate, and function as desired in mammals. The inventors can transplant neurogenic tissue from hiPSCs that are differentiated using Noggin and SB431542 protocol followed by a dopamine neuron induction protocol are transplanted into the brains of recipient mice (specifically, Nod/SCID) and assessment of the engraftment potential of the cells is assessed.

Further, it is possible to observe pigmented cells when the cells are further differentiated from the Noggin and SB431542 protocol towards more mature neurons (both motor neurons and dopamine neurons). This data suggests that both melanocytes and retinal-pigmented epithelium are being produced. Additionally, PAX6+ central nervous system progenitor cells and a PAX6-HNK1+ peripheral nervous system progenitor cell were observed. Recent publications have reported the reprogramming of human somatic cells into induced pluripotency stem cells (hiPSCs) (Takahashi, et al., Cell 131 (5), 861 (2007); Suter, et al., Stem Cells 27, 49-58 (2008)). Next it was determined if dual SMAD inhibition could be used to reliably generate a broad repertoire of hiPSC derived neural cell types. Given the expected intrinsic variability among hiPSC clones, reproducible differentiation results would confirm the robustness of our novel differentiation protocol. Two hiPS clones (IPS$^{C14}$, IPS$^{C17}$; FIGS. 3a-i and a-ii) were generated using lentiviral transduction of human fetal lung fibroblasts with cMYC, KLF4, OCT4, and SOX2. Both clones express the pluripotency markers including Nanog, Tra-1-60, and SSEA-3 at the undifferentiated state and are capable of differentiating into derivatives of the three germ layers. Upon neural induction via the noggin/SB431542 protocol, both clones yielded nearly homogenous populations of PAX6+ cells by day 11 of differentiation (FIG. 3b-i, b-ii). Using the strategies described above manipulating, cell density, passage, and patterning factors both hiPSC clones could be readily biased towards generating HNK1+ putative neural crest progeny (FIG. c-i,c-ii), hiPSC derived R-NSCs (FIG. 3d-i, d-ii), and specific hiPSC derived neuron subtypes including somatic motor neurons (FIG. 3e-i,e-ii) and dopamine neurons (FIG. 3f-i,f-ii). These data demonstrate robustness and modularity of the dual SMAD inhibition strategy beyond hESC differentiation. The novel protocol offers an efficient, defined, and robust platform for the rapid generation of hiPSC derived neural cell types.

Thus a novel method of neural differentiation was discovered by combining at least two signaling inhibitors, i.e. SB431542 and Noggin. While for most of the studies presented herein used a 11-day treatment period, subsequent studies showed that comparable levels of neural induction were achieved when the treatment is shortened to the first 5 days of differentiation (FIG. 10). This reduced time of treatment should further reduce complexity and cost, particularly in the case of recombinant Noggin. In some embodiments, an inhibitor of SMAD signaling is replaced by an inhibitor of a Bone morphogenetic protein (BMP signaling) pathway. Small molecule inhibitors of the BMP pathway are also available that could potentially substitute for noggin function and further reduce costs. Thus, in some embodiments, noggin is replaced by Dorshomophin. In other embodiments, noggin is replaced by LDN-193189, for an exemplary structure see

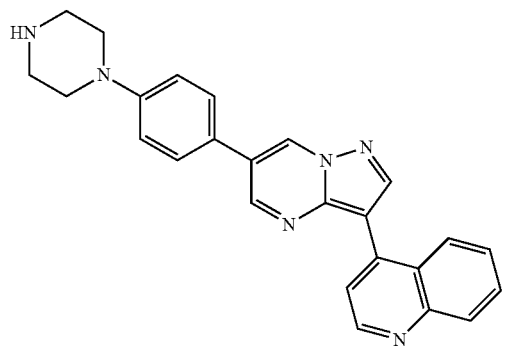 [SMILES: c1ccc2c(-c3cnn4cc(-c5ccc(N6CCNCC6)cc5)cnc34)ccnc2c1]

(another example, 'Stemolecule™ BMP Inhibitor LDN-193189' StemGent, Cambridge, Mass.).

Cranial placodes are transient developmental structures critical for the formation of the lens, nasal epithelium, otic structures, cells of the adenohypophysis, and multiple cranial nerves including the trigeminal ganglion. Little is known about human placode biology due to the inaccessibility of the tissue during development and the lack of validated markers. Most of our knowledge is extrapolated from other species such as xenopus, zebrafish, chick, and to lesser extent mouse development. Here, The inventors report the derivation of cranial placodes and placode derived sensory neurons from human embryonic stem cells (hESCs). Six1+ hESC derived placode precursors are obtained at high yield (71% of total cells) within 11 days of differentiation using a modified dual SMAD inhibitor protocol. Six1+ cells co-express other putative placode markers such as eyes absent homolog 1 (Drosophila) (Eya1), Dachshund homolog 1 (Dach1), eyes absent homolog 4 (Drosophila) (Eya4), and SIX homeobox 3 (Six3; sine oculis homeobox homolog 3 (Drosophila)) and temporal transcriptome analysis identifies additional placode and sub-placode specific markers. Prospective pan-placode precursor cells were isolated based on the expression of p75 in the absence of HNK1 expression. Specific enhancer GFP constructs enable marking placodal cells with putative specificity to a subset of placodal regions. Human ESC derived placodal cells were highly efficiently converted into pure populations of sensory neurons expressing insulin gene enhancer protein ISL-1 (Isl1), brain-specific homeobox/POU domain protein 3A (Brn3a), β-III-tubulin (Tuj1) and peripherin. The isolation of hESC-derived placodal represents a novel model system to study human placode development and enable the derivation of unlimited numbers of previously inaccessible sensory neuron population for the study of sensory function and pain.

Cranial placodes are transient developmental structures that give rise to the peripheral olfactory system, the lens, the anterior pituitary, otic structures, and sensory ganglia including trigeminal neurons. Defects in placode development are involved in a range of human congenital malformations, including blindness, deafness and loss of the sense of smell (Baker, et al., Dev Biol, 232(1):1-61 (2001); Bailey, et al., Curr Top Dev Biol, 72:167-204 (2001), herein incorporated by reference). Cranial placode development has been well characterized in various model organisms including Xenopus, chick and zebrafish (Baker, et at, Dev Biol, 232(1):1-61 (2001); Bailey, et al., Curr Top Dev Biol, 72:167-204 (2006); Bhattacharyya, et al., Curr Opin Genet Dev. 14(5): 520-6 (2004); and Baker, et al., Development, 2000. 127 (14): p. 3045-56, all of which are herein incorporated by reference). Despite the importance of placode biology in development and disease, however, human placode development has remained unexplored. This is largely due to inaccessibility of early human placode tissue and the associated lack of appropriate markers and techniques.

Embryonic stem cells have the unique ability to self-renew in a nearly unlimited fashion while retaining the ability to differentiate into all the various cell types that make up an adult organism. During human development, pluripotent cells of the inner cell mass (ICM) and epiblast from which human ES cells are derived gives rise to the three germ layers and all subsequent derivatives, including placode cells. One key question is whether the in vivo differentiation potential of the human ICM were harnessed using human ES cell-based culture systems in vitro.

Over the last few years a number of protocols have been developed by our lab and others for the directed differentiation of human ES cells into various tissue specific cell types, such as midbrain dopamine neurons, Perrier, et al., Proc Natl Acad Sci USA, 101(34):12543-8 (2004), herein incorporated by reference, spinal motoneurons Li, et al., Nat Biotechnol, 23(2): 215-21 (2005), herein incorporated by reference, multipotent mesenchymal precursors, Barberi, et al., PLoS Med, 2(6):e161 (2005); Barberi, et al., Nat Med, 2007. 13(5):642-8, herein incorporated by reference, cardiac cells, Laflamme, et al., Nat Biotechnol, 25(9):1015-24 (2007), herein incorporated by reference, and hepatocyte-like cells Agarwal, et al., Stem Cells, 26(5):1117-27 (2008), herein incorporated by reference. Directed differentiation into cells of peripheral neuron identity has been achieved via a neural crest precursor intermediate. The initial protocols on generating human ES cell-derived neural crest cells, Lee, et al., Nat Biotechnol, 25(12):1468-75 (2007), herein incorporated by reference were based on a MS5 co-culture system promoting neural induction, Perrier, et al., Proc Natl Acad Sci USA, 101(34):12543-8 (2004); Barberi, et al., Nat Biotechnol, 21(10):1200-7 (2003), herein incorporated by reference. The MS5 culture system was used successfully for deriving and isolating various neural crest fates from human ES cells and human IPS cells, and for modeling a familial dysautonomia (FD), a rare human genetic disorder affecting neural crest-derived neurons, Lee, et al., Nature, 461(7262):402-6 (Epub 2009 Aug. 19) herein incorporated by reference.

Recently, our lab developed a novel and defined neural induction strategy that is based on the concomitant inhibition of the BMP and TGFb/Activin/Nodal signaling pathways, Chambers, et al., Nat Biotechnol, 27(3):275-80 (2009), herein incorporated by reference. Exposure to Noggin (N) and SB431542 (SB) leads to a synchronized and rapid differentiation of human ES cells or IPS cells towards neural fates under adherent culture conditions and therefore obviates the need for both co-culture and embryoid body formation during the induction process. The more rapid and synchronized differentiation response using the N-SB protocol enables testing of the precise relationship of specific morphogens in biasing developmental fate in vitro.

Here The inventors describe a modified N-SB protocol that allows the efficient derivation of highly enriched populations of placodal precursors. Placodal fate is induced at the expense of neuroectodermal cells upon withdrawal of noggin treatment 48 hours after N-SB induction. These data illustrated the use of the N-SB induction system to optimize the generation of non-CNS derivatives, demonstrate the importance of endogenous BMP signaling during hESC differentiation and enable the derivation of unlimited numbers of placode derivates such as cranial sensory neurons for the study of sensory function and pain.

The inventors made several observations from the studies described herein which are presented as follows for use in methods of the present inventions.

BMP Dependent Specification of Placodal Fates During HESC Differentiation. BMPs exert wide-ranging effects on early embryonic fate specification in vivo and are involved in the specification of various extra-embryonic structures, determination of definitive mesodermal cells, specification of non-neural ectoderm, placode and neural crest tissues. The use of the N-SB culture system enables a highly synchronized and efficient differentiation of human ES cells. In our current study the N-SB system reveals an exquisite control of BMP dose and timing of application in the specification of placodal fates. Important questions remain whether the system were used similarly to optimize differentiation towards non-neural ectoderm fates and the generation of primitive skin precursor cells. Data indicated that a subset of Six1 negative cells under the modified N-SB culture conditions express p63, a known marker of early epidermal precursors during development.

The Emergence of Putative Pan-Placodal Fates During Human Embryonic Stem (ES) Cell Differentiation. Highly efficient differentiation towards Six1+ fates and the rapid emergence of insulin gene enhancer protein ISL-1, also known as ISL LIM homeobox 1, (Isl1)+ cells during human ES cell differentiation suggest that hESC derived cells may initially adopt a pre-placodal precursor fate. The emergence of a preplacodal region has been described during xenopus and zebrafish development marking a horseshoe shaped area in the most anterior region of the embryo surrounding the anterior neuroectodermal cells. The current study focused primarily on the generation of sensory neuron precursors from the Six1+ placodal regions. However, future studies should address the plasticity of these placodal cells upon exposure to alternative differentiation regimens. Of particular interest may be the derivation of adenohypophyseal cells to study specification of various hormone producing cell types. Such cells are of interest for developmental studies and for studies aimed at defining pharmacological control of hormone release. Approximately, 15% of the cells at the Six1+ stage express Lhx3, a marker of adenohypophyseal precursor cells. Expression of CGA, the precursor protein in the production of adenohypophyseal hormones, was observed during human ES cell differentiation in the modified N-SB protocol at day 11 of differentiation (FIG. 12D). The presence of Lhx3+ putative adenohypophyseal precursor cells and the expression of CGA showed that cells of adenohypophyseal lineage were readily induced using the modified N-SB protocol.

Sensory Neuron Specification from Six1+ Placodal Precursors. Our findings strongly indicate a placodal origin of the sensory neuron populations generated in the modified N-SB protocol. This is based on the expression of Six1 in the precursor clusters isolated for subsequent sensory neuron generation and the co-expression of Six-1 in early stage sensory neurons. Placode derived sensory neurons share various markers with sensory neurons derived from neural crest lineages such as Brn3A, Isl1 and Peripherin. However, the modified N-SB protocol shows highly efficient induction of FoxG1B and other anterior markers expressed in placodal precursor and not expressed in early neural crest lineages. It will be interesting to explore how initial cell density (Chambers et al., Nature Biotechnology 27(3) 275-280, 2009, Corrigendum: in Nature Biotechnology 27(4):1) and modulation of Wnt signaling (reference) may enable specification of placodal versus neural crest derived sensory neuron populations. Access to highly purified populations of cranial sensory neurons represent a novel tool for the future development high throughput drug discovery assays. For example compounds modulating placode derived trigeminal neurons may be of particular interest given the well known clinical syndromes associated with trigeminal nerve dysfunction.

I. Specification of Functional Floor Plate Tissue from Human Embryonic Stem Cells Occurs at the Expense of Anterior Neurectoderm.

The floor plate (FP) is a critical signaling center during neural development located along the ventral midline of the embryo. Little is known about FP development in humans, due the lack of tissue accessibility. This disclosure describes the derivation of human embryonic stem cells (hESC-) and subsequently derived FP tissue capable of secreting Netrin-1 and SHH and influencing patterning of primary and hESC derived tissues. Induction of FP in hESCs is dependent on early SHH exposure and occurs at the expense of anterior neurectoderm (AN). Global gene expression and functional studies identify SHH-mediated inhibition of DKK-1 as key factor in AN repression. hESC derived FP tissue is shown to be of anterior SIX6+ character but responsive to caudalizing factors suppressing SIX6 expression and inducing a shift in expression of region-specific SHH enhancers. These data established hESC derived FP as an experimental model system and define early signaling events that modulate FP versus AN specification.

Neural development is dictated in time and space by a complex set of signals that instruct neural precursor identity. While significant progress has been made in animal models, human neural development remains much less understood. Human embryonic stem cells (hESCs) offer an accessible and manipulatable cell platform to model the early stages of human development.

Previous studies have reported the directed differentiation of mouse (Wichterle et al., 2002; Barberi et al., 2003; Watanabe et al., 2005) and human (Perrier et al., 2004; Li et al., 2008; Eiraku et al., 2008) ESCs into specific neuron types in response to patterning factors defining anterior/posterior (A/P) and dorso-/ventral (D/V) CNS identity These studies demonstrate evolutionary conservation of signaling systems that specify the major CNS regions. In mammals, sonic hedgehog (SHH) is the key ventralizing factor acting in a dose-dependent manner to specify the various ventral cell types including cells expressing floor plate (FP) in primary neural explants (Briscoe and Ericson, 1999) and in mouse ES cells (Mizuseki et al., 2003). While application of SHH to hESC-derived neural cells has been shown to induce various ventral neuron types, the derivation of floor plate (FP) tissue itself has not yet been reported. As FP is one of the most important signaling centers, the ability to produce FP from human ES cells will be a major step forward in furthering our studies of early human neural development.

The FP runs along the most medial aspect of the ventral neural tube extending most causally from the spinal cord, through the midbrain, up to the diencephalon with its anterior limit being just below the zona limitans intrathalamica (Jessell et al., 1989). Interestingly, at the most anterior aspect the FP stops where the anterior neurectoderm (AN) begins, and studies have shown that AN commitment renders cells incapable of responding to FP inductive signals (Placzek et al., 2003). Classic studies have shown FP cells to exhibit a unique, flat morphology, and to express FP specific markers including SHH, FOXA2, F-Spondin, and Netrin-1 (Placzek, 1995). Studies in mouse and chick embryos have identified two major organizer functions for the FP: the secretion of the morphogen SHH patterning the ventral neural tube (Placzek and Briscoe, 2005), and the expression of Netrin-1 guiding commissural axons across the midline (Charron et al., 2003). The FP is generally considered a non-neurogenic region. However, genetic lineage mapping studies in the mouse have recently reported that the midbrain FP selectively exhibits neurogenic potential and is the source of ventral midbrain dopamine neurons (Kittappa et al, 2007; Ono et al., 2007; Joksimovic et al., 2009).

To date, little is known about FP development in humans, due to lack of accessibility to tissue. In animals, the FP is a major site of SHH production and several human developmental disorders are related to alterations in midline SHH signaling (Mullor et al., 2002) including certain forms of holoprosencephaly and microphthalmia, skeletal disorders including various cleft plate syndromes, and tumor conditions such as Gorlin's syndrome; a rare genetic disorder caused by a mutation in the SHH receptor Patched 1. Thus, understanding how human FP is generated will be critical for comparative developmental studies of human neural patterning and axonal pathfinding and the resulting cells could potentially serve as a source of specific neuron types that have a FP origin.

The Examples provided herein demonstrate exemplary directed differentiation of hESCs into FP tissue, as the first example of generating a human developmental organizer structure in vitro. The inventors showed that human FP specification is dependent on early high-dose SHH signaling that represses DKK1-mediated specification of AN. Functionality of the FP is demonstrated by secretion of Netrin-1 and SHH and the ability to induce ectopic FP tissue and neurite outgrowth in primary mouse and rat explants.

Human ESC derived FP adopts anterior identity by default but were specified to posterior fates in response to caudalizing cues providing access to region-specific FP tissue. The experimental system presented here, and in combination with compositions and methods described for highly efficient neural conversion of human ES and iPS cells by dual inhibition of SMAD signaling, Nat. Biotechnol. 26, 275-280 (2009); published online 1 Mar. 2009; corrected after print 16 Mar. 2009, Corrigendum: Chambers, et al., should facilitate studies on FP-mediated signaling events critical during early human neural development.

II. Stem Cell Lines

The present invention is not limited to the use of any particular type of human stem cells. Indeed, the use of a variety of types of human stem cells is contemplated. Methods for obtaining totipotent or pluripotent cells from humans, monkeys, mice, rats, pigs, cattle and sheep have been previously described. See, e.g., U.S. Pat. Nos. 5,453,357; 5,523,226; 5,589,376; 5,340,740; and 5,166,065 (all of which are specifically incorporated herein by reference); as well as, Evans, et al., Theriogenology 33(1):125-128, 1990; Evans, et al., Theriogenology 33(1):125-128, 1990; Notarianni, et al., J. Reprod. Feral. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994; Evans & Kaufman, Nature 292: 154-156, 1981; Martin, Proc Natl Acad Sci USA 78:7634-7638, 1981; Doetschman et al. Dev Biol 127:224-227, 1988); Giles et al. Mol Reprod Dev 36:130-138, 1993; Graves & Moreadith, Mol Reprod Dev 36:424-433, 1993 and Bradley, et al., Nature 309:255-256, 1984.

In preferred embodiments, undifferentiated human embryonic cells lines are contemplated for use, for examples, cell line WA09, and the like.

III. Discussion

An important finding of the studies described herein, is the "default" nature and anterior bias of the embryonic cell derived FP tissue. The lack of any obvious mesodermal intermediates in both NSB (Chambers et al., 2009; FIG. 4) and the FP (FIG. 4) induction protocol presented here, suggests that the in vitro derivation of neuroectoderm and FP tissue is not dependent on any additional mesoderm derived signals. Interestingly, FP induction occurs readily even in the presence of SB431542, an inhibitor of TGFb/Activin/Nodal signaling in contrast to data in zebrafish where nodal is thought to be essential for FP induction (reviewed Placzek and Briscoe, 2005). The anterior default of the FP tissue reported here is reminiscent of the anterior default observed in hESC derived neuroectodermal cells. Studies in chick development have proposed two distinct origins of anterior versus posterior FP namely progenitors in the epiblast and axial mesoderm (Placzek et al., 2003). This data indicated that human FP precursor cells, similar to neuroectodermal cells, are capable of being respecified towards posterior FP identity in response to caudalizing factors including FGF8 and Wnt-1.

To date, it has not been clearly shown whether expression of AN markers inhibits the ability of cells to yield certain lineages. In hESC derived neural rosette cells, expression of BF1 does not preclude patterning towards posterior CNS fates including HB9+ somatic motoneurons.

However, the efficiency of generating caudal neuron fates is significantly reduced as compared to BF1-negative rosettes (Elkabetz, et al., 2008). Previous studies in primary mouse explants showed that AN cells are not competent to differentiate into FP cells in response to SHH alone (Placzek, et al., 1993). The methods and results described herein during the development of the present inventions showed an AN commitment that was not capable of FP specification.

An additional key finding described herein is a dramatic (strong) induction of DKK-1 during NSB-mediated neural differentiation. During neural differentiation of mouse ESCs exposed to extrinsic DKK-1 enhanced AN induction under serum-free embryoid body (SFEB) conditions (Watanabe et al., 2005). Thus the inventors contemplate that early induction of endogenous DKK-1 during neural differentiation is least in part responsible for the AN default phenotype observed in hESCs. Functional studies demonstrated herein that inhibition of DKK-1 using blocking antibodies significantly improved FP yield. Further, addition of DKK-1 antibodies along with SHH at day 5 or later time-points was not sufficient to extend the temporal window of FP competency (FIGS. 5H and 5I). Similarly, the addition of WNTs (Wnt-1, Wnt3A or GSK inhibitor (BIO)) to neural rosette stage cells was not sufficient to induced FP competency (FIG. 11). These data demonstrated that very early DKK1 mediated AN bias suppresses FP potential of hESC derived precursors.

Additional data in BF1 knockdown hESC lines showed enhanced FP yield with improved yield of posterior CNS cell types such as HB9+ motoneurons. Thus a model system presented herein is contemplated to be suitable to assess the contribution of other molecules with WNT inhibitory function such as Cerberus (Bouwmeester, et al., 1996) to AN specification and repression of FP fate. Finally, the system and methods described herein are contemplated to allow the identification of potential upstream regulators of DKK-1 expression regulating AN default in hESCs.

Suppression of DKK-1 and subsequently AN fates via early exposure to high levels of extrinsic SHH results was a surprising result, as SHH is a classic ventralizing factor and not known to exert effects on AP specification during neural development. Our studies did not address whether regulation of DKK-1 by SHH is direct or caused by inducing an alternative precursor population devoid of DKK-1 expression. While DKK-1 inhibited FP induction, exposure to WNT1 enhanced the derivation of FP tissue from hESCs. These data raised the question whether RA that induce a similar increase in FP yield would affect WNT signaling or whether induction of posterior fates enhances FP yield independently of Wnt signaling.

The availability of unlimited number of FP cells of defined regional identity provides a valuable tool for studying human neural development. Recent studies in the mouse suggest that some regions of the FP, beyond key roles in neural patterning and axonal path finding, may serve as a source of specific neuron types including midbrain dopamine neurons. The inventors demonstrated re-specification of regional identity of hESC derived FP towards midbrain character based on the expression of midbrain specific markers and the activation of midbrain specific SHH enhancer elements. The inventors found evidence that hESC derived FP tissue is capable of yielding TH+/FOXA2+ putative midbrain DA neurons (FIG. 11). The results shown herein provided insights into the induction and regional specification of human FP versus AN fates and established hESCs as a powerful model system to create a functional organizer tissue suitable for modeling more complex interactions during human development.

In conclusion, exemplary data shown herein showed that neural differentiation hESCs default towards an fate by upregulating DKK-1 and subsequently BF1, while AN commitment actively repressed FP competency in hESC progeny. However, an early high level of SHH reduced DKK-1 levels enabling FP induction at the expense of AN while loss-of-function of DKK-1 or BF1 increased FP production. Thus, human ESC derived FP isanterior by default but was posteriorized in respons to caudalizing factors. This is summarized in FIG. 20E.

Thus, numerous embodiments of the present inventions are summarized in the following Tables.

TABLE A

Exemplary ranges of amounts of compounds for obtaining neural cells of the present inventions.

|  | Concentration range of Noggin | Concentration range of Dorsomorphin | Concentration range of SB431542 | Concentration range of Sonic S25II (SHH) |
|---|---|---|---|---|
| Noggin with SB431542 | 125-500 ng/mL | NA | 0.001 to 1000 microM | NA |
| Noggin with SB431542 and SHH | 500 ng/mL | NA | 0.001 to 1000 microM | 200-2000 ng/mL |
| Dorsomorphin with SB431542 | NA | 100-5000 nM, best results 600 nM | 0.001 to 1000 microM | NA |
| Noggin with Dorsomorphin with SB431542 | 25-500 ng/mL, high efficiency to 30 ng/mL | 100-5000 nM, best results 600 nM | 0.001 to 1000 microM | NA |

TABLE B

Exemplary time of addition of compounds of the present inventions for producing neural cell types of the present inventions.

| Start Cell Type and conditions | Stem cells including iPS and hESC. Low density of cells; KSR medium or conditioned medium | Stem cells including iPS and hESC. High density of cells: KSR medium or conditioned medium | Stem cells including iPS and hESC. Low or High density of cells: KSR medium or conditioned medium | Modified N-SB treated hESC or iPS: KSR medium or conditioned medium | N-SB treated hESC or iPS in non-adherent embryoid bodies |
|---|---|---|---|---|---|
| N-SB: Noggin and/or Dorsomorphin with SB431542 | Add both day 0 of culture and continue adding fresh aliquots when feeding cells | Add both day 0 of culture and continue adding fresh aliquots when feeding cells | Add both day 0 of culture and continue adding fresh aliquots when feeding cells | NA | Add both day 0 of culture and continue adding fresh aliquots when feeding cells; SB withdraw at or around Day 7 |
| Modified N-SB Noggin/Dorsomorphin withdrawal 2 days (1-3) after N-SB induction | NA | NA | NA | Add both day 0 of culture and replace with cell media without Noggin and/or Dorsomorphin day 1 (ranging from 6 hours to 4 days after day 0) | NA |
| SHH or C25Il | NA | NA | Add day 1 after N-SB additions (ranging 0-5 days) Gradually replacing KSR media with N2 media between Day 5 and 11. | NA | NA |

TABLE B-continued

Exemplary time of addition of compounds of the present inventions for producing neural cell types of the present inventions.

| Start Cell Type and conditions | Stem cells including iPS and hESC. Low density of cells; KSR medium or conditioned medium | Stem cells including iPS and hESC. High density of cells: KSR medium or conditioned medium | Stem cells including iPS and hESC. Low or High density of cells: KSR medium or conditioned medium | Modified N-SB treated hESC or iPS: KSR medium or conditioned medium | N-SB treated hESC or iPS in non-adherent embryoid bodies |
|---|---|---|---|---|---|
| Resulting cells | CNS progenitor cells (PAX6+) and PNS progenitor cells (p75+, HNK-1+) | CNS progenitor cells (PAX6+) (R-NS cells and patternable neuronal populations of motoneurons and dopaminergic neurons within 19 d of initiating differentiation) | FOXA2+ (BF1 reduced) SOX17- neural cells i.e. FP differentiation with FP anterior cells as a default type but posterior FP tissue can be induced in the presence of caudalizing factors such as Wnt-1, FGFF8 or RA. | Six1+ placodal precursors leading to Brn3a+ progenitor cells, leading to immature neuronal cells, Tuj1+, peripherin+ and mature neurons. | High efficiency motor neuron cells |

REFERENCES

The following references are herein incorporated in their entirety. Barberi, et al., (2003). Nat Biotechnol. 10:1200-1207; Bouwmeester, et al., (1996). Nature 382:595-601; Briscoe, J., and Ericson, J. (1999). Semin Cell Dev Biol. 3:353-62; Chambers, et al., (2009). Nat Biotechnol 27, 275-280; Charrier, et al., (2002). Development 129:4785-4796; Charron, et al., (2003). Cell 113:11-23; D'Amour, et al., (2005). Nat Biotechnol 23, 1534-1541; Dennis, et al., (2003). DAVID: Database for Annotation, Visualization, and Integrated Discovery. Genome Biol 4, P3; Eiraku, et al., (2008). Cell Stem Cell 3, 519-53; Elkabetz, et al., (2008). Genes Dev 22:152-165; Ericson, et al., (1996). Cell 87, 661-673. ; Fasano, et al., (2007). Cell Stem Cell 1, 87-99; Fasano, et al., (2009). Genes Dev 23, 561-574; Glinka, et al., (1998). Nature 391, 357-362; Haung, et al., (2009). Nat Protoc 4, 44-57; Hunter, et al., (1991). Proc Natl Acad Sci USA 88, 3666-3670; Ivanova, et al., (2006). Nature 442, 533-538; Jeong, et al., (2003). Development 130, 3891-3902; Jeong, et al., (2005). Development. 133, 7761-7772; Jeong, et al., (2008) Nat Genet 40, 1348-1353; Jessell, (2000). Nat Rev Genet 1, 20-29; Jessell, et al., (1989). Ciba Found Symp 144, 255-276; discussion 276-280, 290-255; Joksimovic, et al., (2009). Nat Neurosci 12, 125-131; Kimura-Yoshida, et al., (2006). PNAS 104, 5919-59249; Kittappa, et al., (2007). PLoS Biol 5, e325; Li, et al., (2008). Stem Cells 4, 886-89399; Lois, et al., (2002). Science 295, 868-872; Lyuksyutova, et al., (2003). Science 302, 1903-1904; Matise, et al., (1998). Development 125, 2759-2770; Mizuseki, et al., (2003). Proc Natl Acad Sci USA 100, 5828-5833; Mukhopadhyay, et al., (2001). Dev Cell 3, 423-434; Mullor, et al., (2002). Trends Cell Biol 12, 562-569; Ono, et al., (2007). Development 134, 3213-3225; Perrier, et al., (2004). Proc Natl Acad Sci USA 101, 12543-12548; Placzek, et al., (1993). Development 117, 205-218; Placzek, M. (1995). Curr Opin Genet Dev 5, 499-506; Placzek, et al., (2003). Development 130, 4809-4821; Placzek, et al., (2005). Nat Rev Neurosci 6, 230-240; Roelink, et al., (1994). Cell 76, 761-775; Shen, et al., (2006). Nat Neurosci 9, 743-751; Shirasaki, et al., (1995). Neuron 14, 961-972; Suter, et al., Stem Cells, 27(1):49-58 (2009); Venezia, et al., (2003). PLoS Biol 10, e301; Watanabe, et al., (2005). Nat Neuro 3, 288-296; Weinstein, et al., (1999). Annu Rev Cell Dev Biol 15, 411-433; Wichterle, et al., (2002). Cell 110, 385-397; Zhang, et al., Nature Biotechnology 19, 1129-1133 (2001); and Zoltewicz, et al., (1999). Development 126, 5085-5095.

EXPERIMENTAL

The following examples serve to illustrate certain embodiments and aspects of the present invention and are not to be construed as limiting the scope thereof. In the experimental disclosures which follow, the following abbreviations apply: N (normal); M (molar); mM (millimolar); μM (micromolar); mol (moles); mmol (millimoles); mol (micromoles); nmol (nanomoles); pmol (picomoles); g (grams); mg (milligrams); μg (micrograms); ng (nanograms); pg (picograms); L and (liters); ml (milliliters); μl (microliters); cm (centimeters); mm (millimeters); μm (micrometers); nm (nanometers); U (units); min (minute); s and sec (second); deg (degree); and ° C. (degrees Centigrade/Celsius).

The following are general cell culture formulations.
hESC Medium for Maintenance (1 Liter):
800 mL DMEM/F12, 200 mL of Knockout Serum Replacement, 5 mL of 200 mM L-Glutamine, 5 mL of Pen/Strep, 10 mL of 10 mM MEM minimum non-essential amino acids solution, 1000 μL of β-mercaptoethanol, bFGF (final concentration is 4 ng/mL)
KSR Medium for hESC Differentiation (1 Liter):
820 mL of Knock out DMEM, 150 mL of Knock out Serum Replacement, 10 mL of 200 mM L-Glutamine, 10 mL of Pen/Strep, 10 mL of 10 mM MEM, 1 mL of β-mercaptoethanol
N2 Medium for hESC Differentiation (1 Liter):
985 ml dist. $H_2O$ with DMEM/F12 powder, 1.55 g Glucose, 2.00 g $NaHCO_3$, 25 mg insulin, 0.1 g apotransferrin, 30 nM sodium selenite, 100 μM putrescine, 20 nM progesterone
DMEM with 10% FBS for Preparing PMEF (1 Liter):
885 mL of DMEM, 100 mL of FBS, 10 mL of Pen/Strep, 5 mL of L-Glutamine Alpha MEM with 10% FBS for preparing MS-5 feeder (1 liter):
890 mL of Alpha MEM, 100 mL of FBS, 10 mL of Pen/Strep
Gelatin Solution (500 ml):
Dissolve 0.5 g of gelatin in 500 ml of warm (50-60° C.) Milli-Q water. Cool to room temperature.
Noggin was purchased from R&D system as Catalog Number: 719-NG,
Recombinant Mouse Noggin Fc Chimera.

Example I

Bone Morphogenetic Protein (BMP) Levels Determine Placode Fate Identity.

Sensory placodes are developmental structures formed at the interface of early neuroectodermal and non-neural ectoderm tissue. To address whether the N-SB culture system is suitable for the derivation of placodal cells, The inventors first established a set of markers to identify placode identity in human embryonic stem cells (hESCs)-derived cultures. From studies in other model organisms, The inventors postulated a number of candidate markers to identify human placodal precursor during hESC differentiation including member of the Six, Eya, and Dlx family of transcription factors. Six1 marks the pre-placodal region and placodal cells in model organisms but is also expressed in skeletal muscle precursors. Immunocytochemical analyses revealed 6%±4% Six1+ cells at day 11 of N-SB differentiation. The absence of the expression of skeletal muscle markers in Six1+ cells suggested placodal precursor cell identity.

A large number of developmental studies have demonstrated a critical role for BMP signaling during early ectodermal patterning in vivo. One model suggests that a gradient of Bmp activity within the ectoderm allocates different cell fates, with high levels of signaling promoting epidermis, moderate levels inducing placodes, intermediate levels specifying neural crest and complete absence of Bmp activity being required for neural plate formation in vivo Streit, et al., Dev Biol, 2004. 276(1): p. 1-15, herein incorporated by reference. To test whether addition of exogenous BMPs enhances the derivation of Six1+ cells, The inventors exposed SB431542 (1 µM) treated hESCs to various concentration of BMP4. However, early addition of BMP4 caused a dramatic morphological chance of the cells and induction of cdx2 suggesting differentiation towards trophoectodermal fates. In agreement with our findings previous studies in the absence of SB431542 have demonstrated that early exposure to BMPs can drive trophoectodermal fates during hESC differentiation Chambers, et al., Nat Biotechnol, 2009. 27(3): p. 275-80; Xu, et al., Nat Biotechnol, 2002. 20(12): p. 1261-4, herein incorporated by reference.

We next explored whether simple withdrawal of the BMP inhibitor noggin during N-SB differentiation may enhance the emergence of placodal fates by de-repressing endogenous BMP signaling. To this end The inventors performed a time course study-removing noggin at different time points of the NSB protocol (FIG. 11A) while monitoring the induction of placodal marker (FIG. 11B) trophoectodermal, neurectodermal by qRT-PCR analysis at day 11 of differentiation. The inventors observed that withdrawal of noggin at day 2 or 3 of differentiation yielded efficient induction of Six1 while noggin withdrawal at day 1 of differentiation lead to the induction of Eya1 in the absence of Six1 expression. The induction of morphological changes and expression of Cdx2 in cultures subjected to day 1 noggin withdrawal indicated differentiation towards trophoectodermal fates and suggested that Eya1 is expressed in trophoectodermal precursors in addition to placodal cells. Immunocytochemical analysis demonstrated that that noggin withdrawal at day 3 of differentiation induced a switch from primarily Pax6+ neurectodermal cells obtained under standard N-SB conditions to populations composed of 71% Six1+ putative placode precursor cells (FIG. 11C, D). Co-labeling studies demonstrated co-expression of other placodal markers in Six1+ cells such as Eya1 in the absence of markers of skeletal muscle fates.

Microarray analysis reveals novel human placode progenitor gene expression: To obtain an unbiased measure of placode induction of placode precursor cell identity The inventors performed a time course analysis of global gene expression using the Illumina bead array platform. RNA was collected at five time points during differentiation (Day 1, 3, 5, 7, and 11) in control N-SB cultures (yielding anterior neural plate cells; noggin/SB431542 treatment for day 1-11) and under conditions promoting placodal fates (anterior placode cells; SB431542 treatment for 11 days; Noggin treatment from day 1-3). Prior the microarray analysis the quality of each sample was verified for expression of a panel of placode markers (Six1, Dlx3, Eya1) and the absence of other lineages such as Foxa2 (endoderm), Sox17 (endoderm), MyoD (skeletal muscle), cdx2 (trophoblast), and T (Brachyury)(mesoderm). Global gene expression studies were carried out in three independent samples for each time point and culture condition. Data were converted into log 2 ratios comparing levels of gene expression in placode versus N-SB protocol during differentiation (FIG. 12A-D).

The time course data were subjected to gene ontology (GO) enrichment analysis using DAVID Dennis, et al., Genome Biology 2003 4:P3, 2003. 4(5): p. P3, herein incorporated by reference) as unbiased assessment of placode transcription profile. Among the transcripts highly enriched in placode conditions versus NSB control cultures at day 5 and day 7 of differentiation were genes associated with the sensory organ development, BMP and Wnt pathways, inner ear development and neural patterning.Enrichment for sensory organ development and neural patterning factors further confirm anterior placode identity of cultures derived using the modified N-SB protocol. Neural plate markers and neuronal markers were also down-regulated in the modified N-SB (noggin withdrawal after 2 days of differentiation) versus NSB (i.e. treatment of cells with at least 2 SMAD or BMP signaling compounds) protocol.

To gain insight into specific genes differentially expressed during placode specification, The inventors performed pairwise comparisons at for each differentiation stage. While the majority of genes significantly regulated at day 5 and day 7 of differentiation (as compared to day 1) were shared in NSB and modified N-SB protocol, a subset of transcripts was differentially regulated. In particular, The inventors noticed an increase in Islet-1, a very well known marker for sensory neuron development, in the modified N-SB protocol. Isl1 is also expressed in other lineages such as motoneuron, heart progenitors and pancreatic islet cells. The early expression onset of expression during hESC differentiation suggests that Islet-1 marks early placode precursor cells similar to its expression during zebrafish development where it marks the horseshoe shaped at the anterior pre-placodal region. thus the inventors discovered during the course of the present inventions that Islet-1 is one of the first placode markers during differentiation of human pluripotent stem cells. The modified N-SB protocol induced highly enriched expression for Islet-1 at day 5, day 7, day 9 and day 11 when compared to NSB conditions. In microarray data obtained by the inventors during the development of the present inventions, placode genes, GATA3, Dlx5, TFAP2a, and TFAP2c are enriched. The inventors also observed significant changes in Wnt pathway and BMP pathway components. As early as Day 5, there was a significant increase of the Wnt pathway inhibitor DKK-1 and this increase was sustained over the course of the protocol. The inventors also observed significant down-regulation of several Wnt receptors in response to removal of Noggin. Induction of BMP antagonists such as gremlin-1 and BAMBI that are activated in response to BMP signaling confirm that noggin withdrawal causes changes in endogenous BMP signaling during hESC differentiation with a corresponding increase of downstream genes.

Furthermore, The inventors identified a number of additional genes that were differentially expressed during anterior placode specification including Shisa2, Ovol2 and Foxc1. Differential expression for these and additional genes was verified by qRT-PCR. Ovol2 is a known marker of surface ectoderm and placodal fates in various model organisms. In mice, the Ovol2 knockout is lethal and Ovol2−/− mouse embryos do not develop placode-derived tissues such as optic cup, and otic vesicle.

A gene cluster analysis showed when genes were expressed the highest; time of maximum (TOM) and the lowest; time of minimum expression (TIM). GO ontology terms were mapped into this analysis and were able to identify precise developmental windows during placode precursor cell specification. These data additionally confirmed the identity of hESC derived placodal tissue and revealed markers and pathways involved in placode versus anterior neural plate (AN) specification.

Clustering of differentially expressed transcripts (FIG. 12E) revealed correct matching of all replicate samples. These data also revealed a close temporal matching of samples independent of treatment while pinpointing to a subset of genes that distinguish neuroectodermal from placodal precursors (boxed area in FIG. 12E). Principle component analysis confirmed high temporal correlation of samples with increasing divergence between neuroectodermal and placodal precursor cells at later differentiation stages (FIG. 12F).

Placode progenitors give rise to sensory neurons Isolation of Six1+ placodal precursors followed by culture under serum free conditions revealed efficient differentiation into neurons that retain Six1 expression (FIG. 13A-C). The sensory neuron identity of these cells was confirmed by the expression of Brn3A, Isl-1 measured at day 20 of differentiation (FIG. 13D, E).

Longer-term differentiation studies (day 40) resulted in cells with strong expression of the peripheral neuron marker Peripherin (FIG. 13F) and reduced expression of Tuj1 compatible with in vitro maturation of sensory neuron progeny. In vitro developmental progression from placode precursor identity to mature sensory neuron fates is illustrated schematically in FIG. 13G.

Figure 14A:
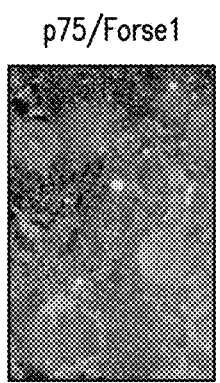
Figure 14B:
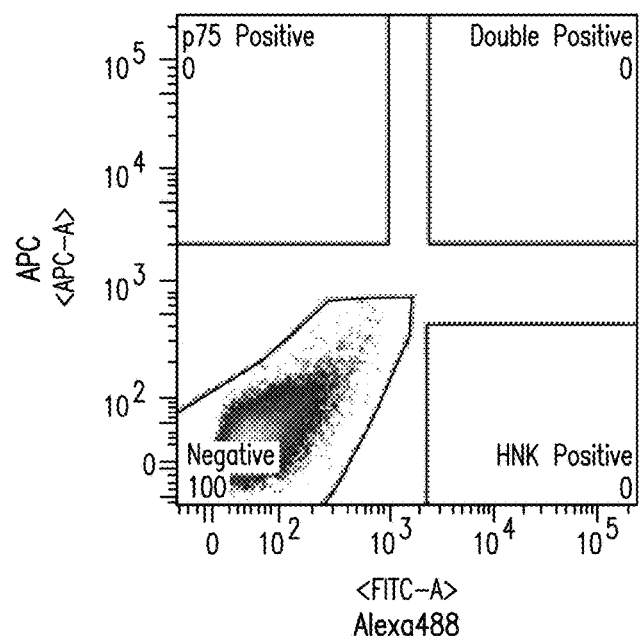
Figure 14B:
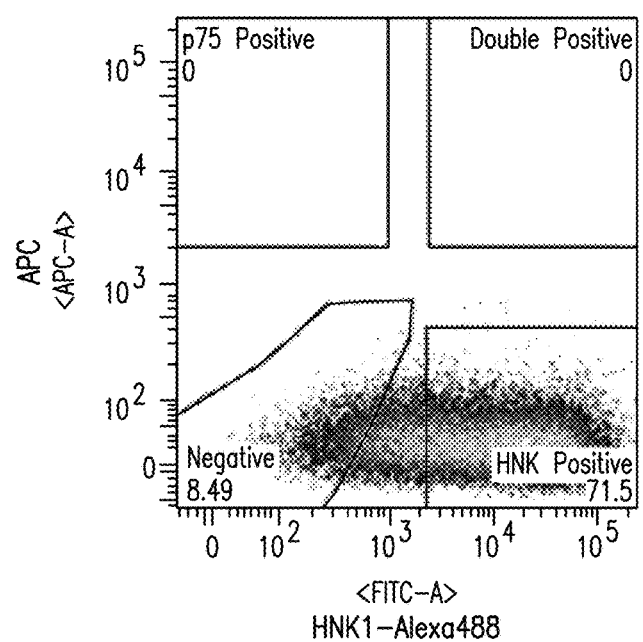
Figure 14B:
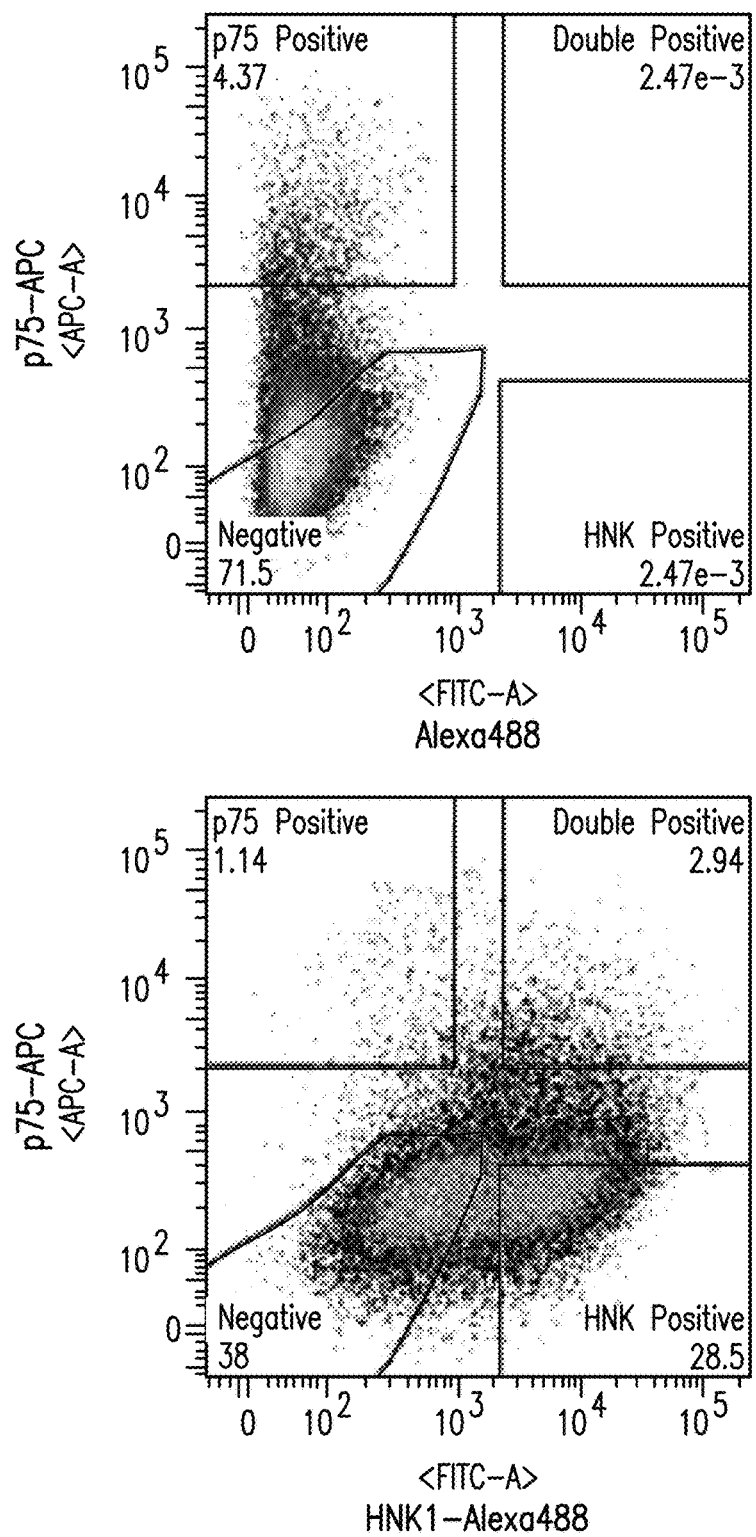
Figure 14C:
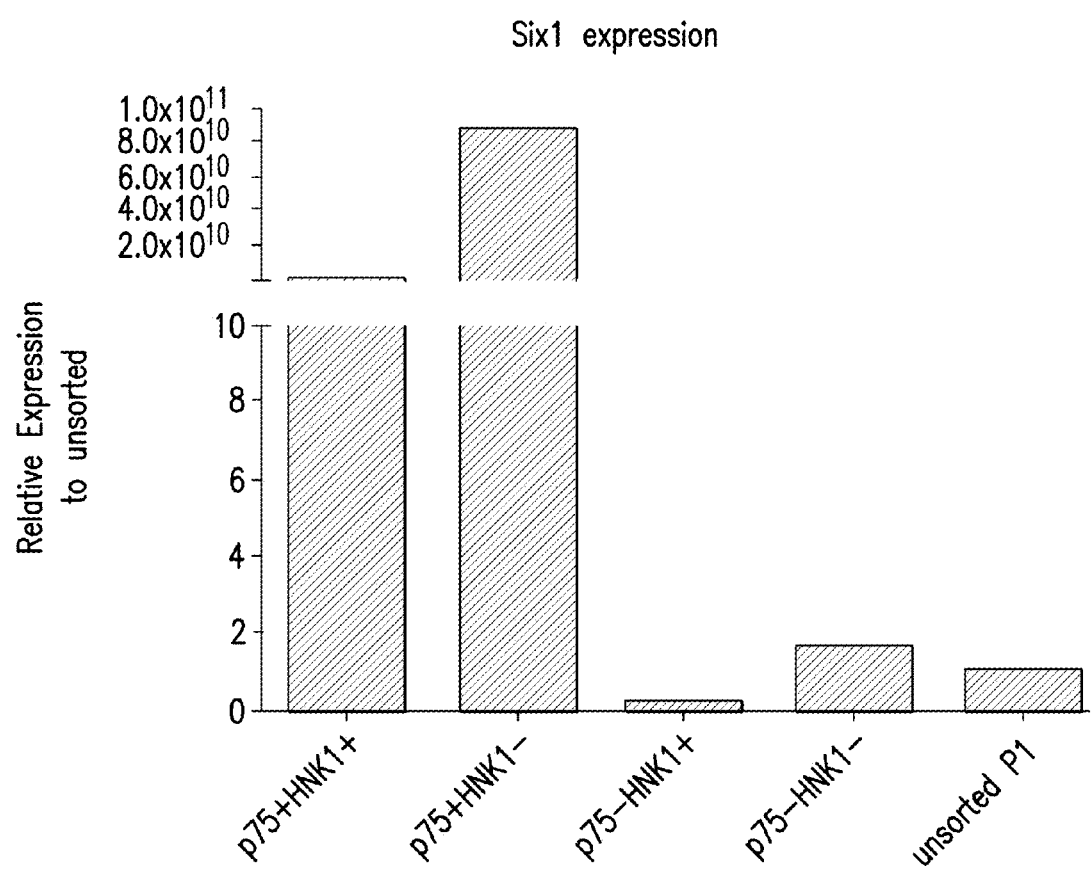
Figure 14D:
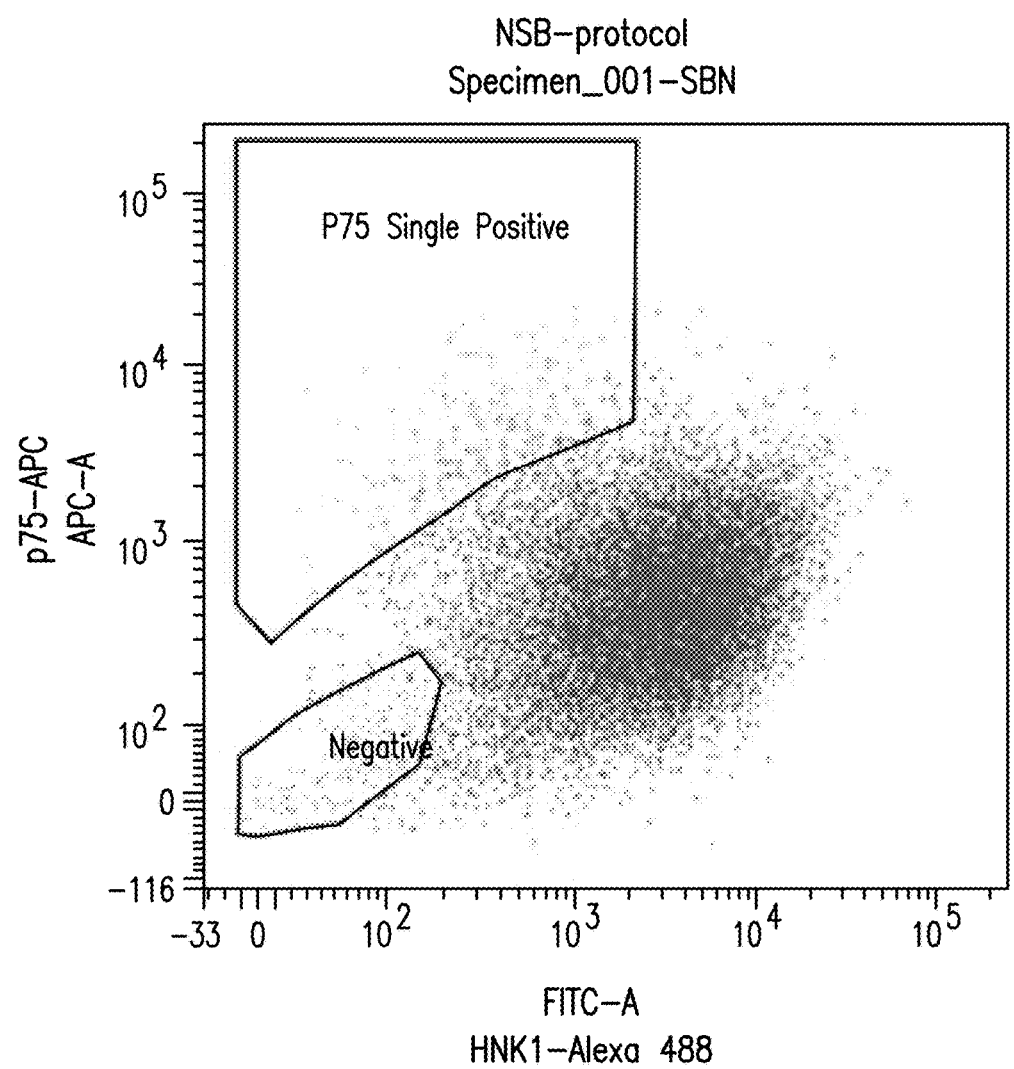
Figure 14D:
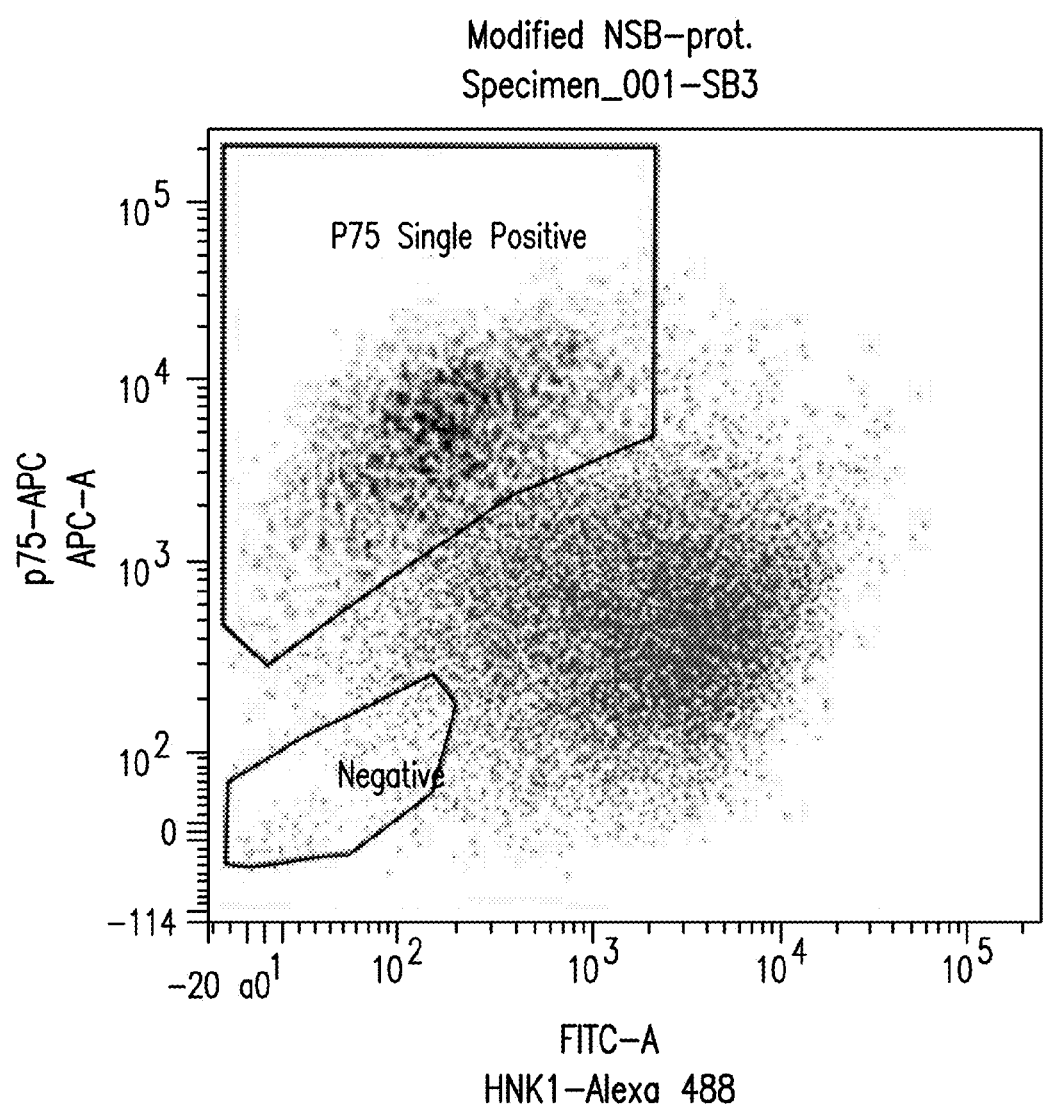

Results showed that simple modifications in the N-SB protocol induce a switch in differentiation from neuroectoderm to placodal precursors. Using timed-noggin withdrawal The inventors obtained a yield of 71% of total cells expressing Six1. The isolation of pure placodal precursors requires markers that prospectively identify placode fate. The identification of prospective markers is also critical to reliably distinguish placodal cells from other alternative lineages such as CNS precursor, neural crest lineages and non-neural ectoderm. Of particular interest is the separation of placode derived from neural crest derived precursors to reliably separate neural crest from placode derived neuronal populations. The inventors have previously demonstrated that isolation of p75+/HNK1+ cells during neural early neural differentiation marks a population of cells fated towards neural crest identity (Lee et al., Nature Biotechnology, 25(12):1468-75 (2007), herein incorporated by reference). Here The inventors tested the relationship of those markers within the placodal lineages. Interestingly, The inventors observed that NGFR efficiently marks placodal cultures in our modified N-SB protocol (FIG. 14A) separated by populations of precursors expressing Forse1, a marker previously associated with anterior neuroectodermal fates (Elkabetz, G&D, 2008, herein incorporated by reference). Double sorting for p75 and human natural killer-1 (HNK1) epitope (also known as CD57) expression revealed that p75-single positive cells, negative for HNK1, are dramatically enriched in Six1 expression based on qRT-PCR analysis (FIG. 14B, C). The placodal identity of the cells is further supported by the increase in the number of p75+/HNK1− cells in the placode-inducing modified N-SB protocol as compared to the neuroectoderm-inducing classic N-SB protocol (FIG. 14D).

Example II

IPS Cell Generation.

The cDNAs encoding hOct4, hSox2, hKlf4 and c-myc (purchased from Open Biosystems) were subcloned into self-inactivating lentiviral vectors driven by the human phosphoglycerate kinase (PGK) promoter. Lentiviral vector supernatants were produced by triple co-transfection of the plasmid DNA encoding the vector, pCMVΔR8.91 and pUC-MD.G into 293T cells. Human fetal lung fibroblasts (MRC-5) purchased from ATCC (CCL-171) were seeded at $1.5 \times 10^4$ cells/cm$^2$ in Eagle's Minimum Essential Medium supplemented with 10% fetal bovine serum (FBS). The following day the fibroblasts were transduced with equal amounts of supernatants of the four lentiviral vectors in the presence of 4 ug/ml polybrene for ~16 hours. Six days after transduction, fibroblasts were harvested by trypsinization and plated at $2 \times 10^4$ cells per 60 mm dish on a feeder layer of mytomycin C-treated mouse embryonic fibroblasts (CF-1). The next day, the medium was switched to hESC medium. The hiPS lines were confirmed positive for Tra-1-81, Tra-1-60, SSEA-4 and Nanog by immunoflouresence and flow cytometry. In both hips clones the 4 vector-encoded transgenes were found to be silenced.

Materials and Methods:

Cells and Culture Conditions (dual SMAD and floor plate). hESCs (WA-09; passages 35-45) were cultured on mouse embryonic fibroblasts plated at 12-15,000 cells/cm2 (MEFs, Global Stem). A medium of DMEM/F12, 20% knockout serum replacement (GIBCO), 0.1 mM b-mercaptoethanol, 6 ng/mL FGF-2 was changed daily. Cells were passaged using 6 U/mL of dispase in hESCs media, washed and re-plated at a dilution of 1:5 to 1:10.

Neural Induction (Dual SMAD).

hESC cultures were disaggregated using accutase for 20 minutes, washed using hESC media and pre-plated on gelatin for 1 hour at 37° C. in the presence of ROCK inhibitor to remove MEFs. The nonadherent hESC were washed and plated on matrigel at a density of 10,000-25,000 cells/cm on matrigel (BD) coated dishes in MEF conditioned hESC media (CM) spiked with 10 ng/mL of FGF-2 and ROCK-inhibitor. Ideal cell density was found to be 18,000 cells/cm$^2$. The ROCK inhibitor was withdrawn, and hESC were allowed to expand in CM for 3 days or until they were nearly confluent. The initial differentiation media conditions included knock out serum replacement (KSR) media with 10 nM TGF-beta inhibitor (SB431542, Tocris) and 500 ng/mL of Noggin (R&D). Upon day 5 of differentiation, the TGF-b inhibitor was withdrawn and increasing amounts of N2 media (25%, 50%, 75%) was added to the KSR media every two days while maintaining 500 ng/mL of Noggin. For MS5 induction, established methods previously reported were used.[18]

Quantitative Real-Time (Dual SMAD).

Total RNA was extracted using an RNeasy kit (Qiagen). For each sample, 1 ug of total RNA was treated for DNA contamination and reverse transcribed using the Quantitect RT kit (Qiagen). Amplified material was detected using Quantitect SYBR green probes and PCR kit (Qiagen) on a Mastercycler RealPlex2 (Eppendorf). Results were normalized to a HPRT control and are from 4-6 technical replicates of 2-3 independent biological samples at each data point.

Neuronal Patterning and Differentiation (Dual SMAD).

Dopaminergic patterning was initiated using BDNF, ascorbic acid, sonic hedgehog, and FGF8 in N2 media as previously reported,[18] and maturation was performed in the presence of BDNF, ascorbic acid, GDNF, TGFb-1, and cyclic-AMP. Motor neuron patterning was performed using BDNF, ascorbic acid, sonic hedgehog, and retinoic acid in N2 media as previously reported.[16]

Microscopy, Antibodies, and Flow Cytometry (Dual SMAD).

Tissue was fixed using 4% paraformaldehyde for 20 minutes, washed with PBS, permeablized using 0.5% Triton X in PBS, and blocked using 1% BSA in PBS. Primary antibodies used for microscopy included PAX6 (Covance), Oct4 (Biovision), AP2 (Novus Biologicals), GBX2 (Sigma), HNK1 (Sigma), HOXB4 (Developmental Studies Hybridoma Bank (DSHB)), Nestin (R&D), NKX6.1 (DSHB), OTX2 (gift), p75 (Advanced Target Systems.), PAX7 (DSHB), PLZF (Calbiochem), TUJ1 (Covance), ZO1 (Zymed), BF1 (FOXG1, gift Esseng Lai), TH (Sigma), HB9 (DSHB), ISL1 (DSHB). CD105-PE (eBioscience) was used for excluding MS5 stromal cells for flow cytometery on a FACScan (BD).

Floor Plate: Neural Induction.

For MS5 induction, established methods previously reported were used (Perrier et al., 2004). Feeder free neural induction was carried out as previously described (Chambers et al., 2009). Briefly, hESCs cultures were disaggregated using accutase for 20 minutes, washed using hESCs media and pre-plated on gelatin for 1 hour at 37° C. in the presence of ROCK inhibitor to remove MEFs. The nonadherent hESCs were washed and plated on matrigel at a density of 20,000 cells/cm2 on matrigel (BD) coated dishes in MEF conditioned hESCs media (CM) spiked with 10 ng/mL of FGF-2 and ROCK-inhibitor. The ROCK inhibitor was withdrawn, and hESCs were allowed to expand in CM for 3 days or until they were nearly confluent. The initial differentiation media conditions included knock out serum replacement (KSR) media with 10 nM TGF-b inhibitor (SB431542, Tocris) and 500 ng/mL of Noggin (R&D). Upon day 5 of differentiation, increasing amounts of N2 media (25%, 50%, 75%) was added to the KSR media every two days while maintaining 500 ng/mL of Noggin and TGF-b inhibitor. For FP induction, Sonic C25II was added at 200 ng/ml. In some experiments, DKK-1 (R&D 100 ng/ml) FGF8 (R&D 50 ng/ml), Wnt-1 (Peprotech 50 ng/ml) and Retinoic Acid (R&D 1 μm) were added.

Quantitative Real-Time PCR.

Total RNA was extracted using an RNeasy kit (Qiagen). For each sample, 1 ug of total RNA was treated for DNA contamination and reverse transcribed using the Superscript III (Invitrogen). Amplified material was detected using Taqman probes and PCR mix (ABI) on a Mastercycler RealPlex2 (Eppendorf). All results were normalized to a HPRT control and are from 3 technical replicates of 3 independent biological samples at each data point.

Microarray Analysis.

Total RNA was isolated at Days 2, 3, 5, 7, and 11 of differentiation from both control (NSB) and FP (NSB+Shh C25II) using Trizol (Invitrogen). Three biological replicates per time point were used. All samples were processed by the MSKCC Genomics Core Facility and hybridized on Illumina human 6 oligonucleotide arrays. Normalization and model-based expression measurements were performed with using the Illumina analysis package (LUMI) available through open-source Bioconductor project within the statistical programming language R. A pairwise comparison between NSB and NSB+Sonic was performed using the Linear Models for Microarray Data package (LIMMA) available through Bioconductor. Genes found to have an adjusted p-value <0.05 and a fold change greater than 2 were considered significant. Expression differences are reported as the log 2 of the fold change. Gene Ontology enrichment was determined by entering gene lists into the Database for Annotation, Visualization, and Integrated Discovery (Huang et al., 2009 and Dennis et al., 2003). Timing of maximal and minimal expression was calculated as previously reported (Venezia et al., 2004).

Briefly, a regression line was fit to both the NSB+Sonic C25II and NSB conditions. From these trend lines, genes were categorized based on at which time point its maximal and minimal expression occurred.

Microscopy, Antibodies, and Flow Cytometery.

Tissue was fixed using 4% paraformaldehyde and Picric acid for 15 minutes, washed with PBS, permeablized using 0.3% Triton X in PBS, and blocked using 10% Donkey Serum. Primary antibodies used for microscopy included PAX6 (Covance), TUJ1 (Covance), ZO1 (Zymed), BF1 (FOXG1, gift E.Lai), TH (Pelfreez), NKX6.1 (DSHB) and FOXA2 (SantaCruz).

Vector Design and Lentiviral Production.

A third generation lentiviral vector (Lois et al., 2002) was modified to express a BF1 ORF from the Ub-C promoter (Fasano et al., 2009) and a BF1 shRNA from the H1 promoter as described (Fasano et al., 2007; Ivanova et al., 2006). Foxg1 shRNA constructs were used as previously described (Shen et al., 2006). The shRNA expressing lentiviral plasmid was co-transfected with plasmids pVSV-G and pCMVd8.9 into 293FT cells. Viral containing media were collected, filtered, and concentrated by ultracentrifugation. Viral titers were measured by serial dilution on NIH 3T3 cells followed by flow cytometric analysis after 72 hours.

Generation of BF1 shRNA and Over-Expressing Human ES Lines.

hESCs (WA-09; passages 35) were dissociated and plated on Matrigel with the ROCK inhibitor as singles cells. 24 hrs post plating the ES cells were transduced with either control (empty vector), BF1 shRNA, or BF-1 ORF containing vectors. 1 week later, GFP expressing colonies were manually picked and plated on MEFs. Cells were then expanded, tested for mycoplasma, and a normal karyotype.

Dissection of Primary Explants.

E8.5, TP Taconic Swiss Webster females were dissected and embryos were removed. Neurectodermal tissues were dissected and left as chunks plated on top of FP cells. For neurite growth assay E12.5 Sprague-Dawley rat cerebellar plate tissue was dissected and plated on top of hESC derived FP cells or control neuroectodermal cells (NSB protocol). Outgrowth from rat explants tissue was analyzed at day 3 of co-culture.

Conditioned Media and ELISA.

hESCs were differentiated to neural or FP cells, Shh was removed a day 6, and the media was harvested at both day 9 and day 11 of cultures. Using a human Netrin-1 ELISA kit (Axxora) according to the manufactures protocol, Netrin-1 protein levels were detected. For co-culture experiments, the media was filtered and added to cultures straight or a 1:2 dilution in fresh media.

Statistical Analysis.

Results shown are mean+s.e.m. Asterisks and pound signs identify experimental groups that were significantly different from control groups by a t-test, one way ANOVA, or two way ANOVA with a Bonferroni correction for multiple comparisons (p-value, 0.05), where applicable.

Example III

Early High-Dose SHH Exposure Induces FOXA2 and Represses BF1.

hESC derived neural cells at the rosette stage were differentiated into both CNS and PNS progeny and patterned towards multiple cells fates along the A/P and D/V axis (Elkabetz et al., 2008). These results demonstrated that rosette stage cells were highly plastic and responsive to patterning cues including SHH. Specification of progenitor cells into FP tissue and cells during mouse development was thought to depend on SHH signaling within early neural lineages. The inventors tested whether rosette-stage neural cells were competent to undergo FP specification in response to SHH. High concentrations of SHH were needed to induce FP during mouse development (Roelink et al., 1994; Ericson et al., 1996). Recombinant N-terminal SHH has a limited activity range due to the lack of posttranslational modifications required for full SHH action. Recently, a modified version of recombinant SHH became available where SHH was tethered to two Isoleucines (Sonic C25II, R&D Systems), mimicking more closely the potency of mammalian SHH protein. In most functional assays C25II was ~10 times more potent than non-modified N-terminal SHH.

However, dose-response studies done during the development of the present inventions with both conventional SHH and SHH-C25II on established rosette-stage neural cells did not yield cells expressing FP markers such as FOXA2 (FP marker) under any of the conditions tested. The majority of cells retained rosette cytoarchitecture and staining for the AN marker BF1 as described previously (FIG. 1A) (Elkabetz et al., 2008). These results were a surprise, i.e. exposure to high SHH was not sufficient to convert established rosette-stage cells into FP.

Based on the hypothesis that FP specification in the mouse occurs at early developmental stages, at the time of or prior to neural induction, the inventors repeated SHE induction studies at Day 9, the time of rosette specification, using classic stromal-feeder mediated neural induction protocols (Elkabetz et al., 2008). Under this paradigm the inventors noticed a drastic change in cell morphology restricted to the cells treated with SHH-C25II (FIG. 1B). Cells exhibited a flat morphology devoid of rosette structures. Furthermore, the inventors' observed a robust upregulation of FOXA2+ and a concomitant decrease in BF1+ cells (FIG. 1C) and the decrease in the total number of ZO1+ rosettes (FIG. 1D). In addition to decreased expression of BF1 the inventors also observed decreased expression of PAX6, another maker expressed in the AN (FIG. 1E). Dose-response studies demonstrated that induction of FOXA2+ cells and the concomitant decrease in BF1 and PAX6 expression were achieved at concentrations of 125-500 ng/ml of SHH C25II (FIG. 1F and not shown). No efficient induction of FOXA2+ cells was observed with any of the concentrations tested using non-modified N-terminal SHH. The inventors performed dose response studies to understand how FP marker induction compared to that of NKX6.1 expression; a gene known to respond to lower concentrations of SHH. At low concentrations of Sonic C25II there is no expression of FP markers FOXA2 and Netrin-1 but a robust increase in NKX6.1 expression. At higher concentrations FP markers rapidly rise, while NKX6.1 expression tapers off (FIG. 1G). These data demonstrated that early exposure to high levels of SHH decreases anterior AN markers and induces the FP marker FOXA2.

Example IV

The Competency for FP Induction is Restricted to a Narrow Window of differentiation.

While a robust (strong observed signal, such as staining) upregulation of FOXA2 was induced with the initial procedures, merely around 30% of the cells were positive after about 21 days of culture using classic stromal-feeder mediated neural induction. Therefore the inventors tested several types of culture compositions and methods for increasing the total number of cultured cells expressing FOXA2.

Recently the inventors developed and described a rapid and defined neural induction paradigm yielding significantly higher numbers of neural cells based on inhibiting SMAD signaling via exposure to noggin and SB431542 (NSB protocol; (Chambers et al., 2009)). Using this protocol, in combination with compositions and methods of the present inventions, the inventors aimed to optimize FP differentiation by adding Sonic C25II at different time points during neural induction and assaying for FOXA2 expression. Differentiation was initiated upon NSB exposure, and Sonic C25II was added at Day 1, Day 3, Day 5, or Day 7 (FIG. 2A). The most efficient FOXA2 induction was observed in cultures treated with SHH starting at day 1 of differentiation with FOXA2+ cells representing about 65% of total cells (FIGS. 2B and 2C). Extended SHH treatment beyond Day 11 of differentiation did not increase FOXA2 yield (FIG. 2D). These data demonstrated that an early high SHH signal is needed to establish FP identity and suggest a critical window of competency for FP specification. Furthermore, the differentiation conditions establish a robust platform for inducing human FOXA2+ cells in vitro.

FOXA2 is a key marker of FP development. However, FOXA2 is also highly expressed in the endoderm. To further characterize the hESC derived putative FP tissue, the inventors performed qRT-PCR analyses for candidate markers at Day 11. Using the NSB protocol as a control, the inventors confirmed a dramatic increase in the expression of FOXA2 and other FP markers including SHE, F-Spondin, and Netrin-1 (FIG. 7). The inventors further characterized the nature of FOXA2+ putative FP cells using a panel of neural precursor, glial, neuronal and non-neural markers (FIG. 7). FOXA2+ cells co-labelled with only a limited subset of these markers including Nestin (86%) and SOX2 (17%). To distinguish FOXA2 expression in hESC derived FP versus endoderm tissue, the inventors differentiated hESCs to endoderm (D'Amour et al., 2005). As expected, under both FP and endoderm differentiation conditions, the inventors observed an increase in FOXA2 expression compared with NSB treated control cells. However, induction of the endoderm marker SOX17 was limited to the endoderm condition and no SOX17 was present in hESC derived FP cells (FIG. 7). The inventors also did not observe expression of other endodermal markers such as AFP and Albumin expression in hESC derived FP cells. These data demonstrated that hESC derived FOXA2+ cells in the NSB+SHH protocol express FP and early neural precursor markers and lack expression of endodermal markers.

Example V hESCs Derived FP Cells are Functional.

The FP has important functional roles during development in neural patterning and axonal path finding (Jessell, 2000). To assess the functional properties of hESCs derived FP conditioned media was isolated at days 9 and 11 and tested for expression of Netrin-1 in the medium using ELISA (FIG. 3A). Under normal NSB conditions, Netrin-1 is detectable at Day 9 and decreases at Day 11 while in the NSB+SHH condition, there is a 3.5 fold increase in Netrin-1 levels, increasing at Day 11 (FIG. 3B). SHH is a critical patterning factor secreted by FP cells and specifying ventral cell types in a dose-dependent manner. To test if hESCs derived FP secretes factors that can specify ventral precursor domains, conditioned media (CM) was isolated at Days 9 and 11 of the differentiation. At Day 6, exogenous SHH was removed and cultures were washed to eliminate any exogenously added SHH from the medium. Naïve neural progenitor cells were isolated at Day 11 of the control (NSB) protocol and cultured with either NSB CM or FP CM. After Day 5 of culture in the presence of CM, the inventors probed for the expression of ventral precursor markers and expression of the SHH responsive gene GLI2. The inventors found that compared with CM obtained from NSB control cultures, CM from hESC derived FP tissue efficiently induced expression of ventral genes including NKX2.1 and NKX6.1 (FIG. 3C). Increase in the expression of ventral markers was confirmed at the level of protein (FIG. 3C').

To see if this result was SHH-mediated, the inventors demonstrated increased expression of GLI2 upon exposure to CM from hESC derived FP. When this experiment was repeated in the presence of the SHH antagonist cyclopamine, all three genes, NKX2.1, NKX6.1, and GLI2 were significantly reduced (FIG. 3C) demonstrating dependence of patterning response on SHH signaling.

Classical studies demonstrated that FP explants can induce an ectopic FP in early neuroectodermal tissue (Placzek et al., 1993). To test if the hESCs derived FP is capable of inducing FP markers in primary mouse explants, neuroectodermal tissue was isolated from an E8.5 mouse embryo and placed it in direct contact with hESC derived FP cells. After 3 days of co-culture explants were identified based on expression of the mouse specific M6 marker, rinsed and mounted on slides to be stained for FOXA2. As a control condition, mouse explants were co-cultured with hESC derived neural tissue using the NSB protocol. While co-culture with control hESC derived neural tissue did not yield FOXA2+ cells, explants co-cultured with hESC derived FP cells showed robust induction of FOXA2+ cells, particularly at the periphery of the explant (FIGS. 4D and 4E). Neurite growth promoting effects of hESC derived FP cells was observed in primary rat E12.5 rat cerebellar plate explants (FIG. 8), an assay used previously to demonstrate axonal growth promoting effects of primary rodent FP tissue (Shirasaki et al., 1995). These experiments demonstrated that hESCs derived FP can mimic the functional properties of primary FP tissue as an organizer by secreting Netrin-1 and SHH capable of ventralizing naïve hESC derived and primary mouse neural precursor cells.

Example VI

Temporal Transcriptome Analysis Reveals that FP Specification Occurs at the Expense of AN.

To gain further insight into the factors critical for human FP specification, high resolution temporal gene expression profiles of candidate markers were performed at 6 time points during the 11 day protocol. FOXA2 expression was observed as steady increase in transcript levels starting at day 3 of differentiation (compared to NSB) consistent with immunostaining data (FIG. 4A). Interestingly, other FP markers; SHH, Netrin-1, and F-Spondin followed a different expression pattern (FIG. 4B-4D). All three markers showed a more delayed induction with a dramatic increase in expression (compared to NSB condition) at day 7 of differentiation. PTCH1 expression is used commonly as a transcriptional readout of SHH activity. Dramatic increase in PTCH1 expression was observed as early as day 3 of differentiation with levels further increasing by a factor of 3 over the next 2 days (FIG. 4E). It has been shown previously that the SHH downstream effector GLI2 is essential for FP induction but decreases at later stages of FP development (Matise et al., 1998) and that GLI2 can directly activate FOXA2 expression (Jeong and Epstein, 2003). An early increase in both GLI2 and FOXA2 expression (FIGS. 4A and 4F) was observed followed by a decrease in GLI2 at Day 11 consistent with a role of GLI2 specifically during FP induction. A similar trend albeit at much lower induction levels is observed for Gill (FIG. 4G).

SOX1 is an early neural marker and is not expressed in the medial FP (Charrier et al., 2002). Consistent with a rapid neural induction, SOX1 was rapidly up regulated in NSB conditions and continued to increase with time. Upon addition of SHH a much smaller increase in SOX1 levels is observed at day 3 compared with control NSB conditions (FIG. 4H). NSB conditions yield neural cells with a AN bias expressing BF1 at high levels (Chambers et al., 2009). However, when SHH is added to the culture, there is a drastic reduction in PAX6 and BF1 at day 7 (FIGS. 4I and 4J). Induction of the endoderm marker SOX17 and mesoderm marker Brachury was not observed (FIGS. 4K and 4L) suggesting that FP induction, similar to AN induction using the NSB protocol, occurs without contribution of an obvious mesodermal or endodermal intermediate. These data demonstrated appropriate marker expression in hESC derived FP, initiated by GLI2 and FOXA2 expression and followed by expression of functional FP markers such as Netrin-1, SHH, and F-Spondin. The drop in PAX6 and BF1 expression at the time of FP specification suggests that induction of FP occurs at the expense of AN.

Example VII

Global Transcriptome Analysis During hESC Derived FP Specification.

Temporal profiles of global gene expression at 5 time points during differentiation was established during the development of the present inventions (Day 1, 3, 5, 7 and 11) in control NSB cultures (yielding AN) and in Sonic C25II treated cultures (yielding FP; see FIG. 2E). Prior to microarray analysis the quality of each sample was verified for expression of a panel of FP markers (FIG. 9). Global gene expression studies were carried out in three independent samples for each time point and culture condition. Data were converted into log 2 ratios comparing levels of gene expression in FP versus NSB protocol during differentiation (FIGS. 4I-4Q). Raw data are available in GEO database.

The time course data were subjected to gene ontology (GO) enrichment analysis using DAVID Dennis et al., 2003) as unbiased assessment of the FP transcriptional profile. Among the transcripts highly enriched in SHH treated versus NSB control cultures at day 7 and 11 of differentiation were genes associated with the Wnt and hedgehog pathways, axon guidance, and secreted proteins (FIGS. 4L and 4M). Enrichment for patterning and axonal guidance factors further confirm FP identity of SHH treated cultures. Further, SHH-mediated suppression of AN was demonstrated when transcripts that included genes involved in forebrain development showed a larger amount of down-regulation in the FP culture methods for producing floor plate cells than when compared to cells cultured with the NSB protocol (FIG. 4L, M).

Pairwise comparisons at for each differentiation stage was done to gain insight into specific genes differentially expressed during FP specification. While the majority of genes significantly regulated at day 3 and day 5 of differentiation (as compared to day 1) were shared in NSB and FP protocol, a subset of transcripts was differentially regulated (FIGS. 4N-4Q). In particular, an increase in Patched-1 (PTCH1), a component and known transcriptional downstream target of the SHH signaling was noticed. In this protocol, PTCH1 is highly enriched at all time points, except D11 where it starts to decrease (FIG. 4N-4Q).

The inventors observed significant changes in the Wnt pathway components. As early as Day 5 there was a significant decrease of the Wnt pathway inhibitor DKK-1 and this decrease was sustained over the course of the protocol (FIG. 4N-4Q and FIG. 7). Significant upregulation of several Frizzled genes that have been previously shown to be involved in midline axon guidance during mouse development (Lyuksyutova et al., 2003) in the midline (FIGS. 4P and 4Q) was also observed. Additionally, a number of additional genes were identified that were differentially expressed during FP specification including SIX6, CAPN6, IGFBP3 and FIBLN1 (FIGS. 4N-4Q). Differential expression for these and additional genes was verified by qRT-PCR (FIG. 9). While systematic in situ hybridization screens in mouse and human embryonic tissue will be required to validate putative human FP markers, based on the literature and MGI (Mouse gene expression database), many of the genes identified have compatible expression patterns in the anterior midline and floor plate tissue such as HESX1 (Zoltewicz et al., 1999) or RBP1 (CRBP1—Hunter et al., 1991) respectively.

Example VIII

A gene cluster analysis was also done that showed when genes are expressed the highest; time of maximum (TOM) and the lowest; time of minimum (TIM) expression. GO ontology terms were mapped during this analysis and were able to identify precise developmental windows during the FP specification process. These data further confirmed the identity of hESC derived FP tissue and provides insight into genes differentially expressed during FP versus neuroectodermal fate specification.

Example IX

Suppression of DKK-1 Blocks AN Commitment and Enhances FP Generation.

The inventors observation that FP commitment occurs at the expense of AN was strengthened by the global gene expression profiles obtained herein that revealed a rapid down regulation of the Wnt signaling inhibitor DKK-1. DKK-1 was initially identified as a factor expressed in the xenopus head organizer that was necessary and sufficient to induce head development (Glinka et al., 1998). DKK-1-mediated inhibition of Wnt signaling during mouse development is essential for anterior brain development (Mukhopadhyay et al., 2001), and FOXA2 knockout embryos show increased expression of DKK-1 in the ectoderm at E7.5 (Kimura-Yoshida et al., 2006). During NSB induction it was observed that DKK-1 transcript levels rise sharply at day 5 from 200 to 5000 fold and then drop back down consistent with the role of DKK-1 as an AN inducer. ELISA assays were done to measure DKK-1 protein levels in the medium and found levels as high as 12 ng/ml (FIGS. 5A, B). A drastic reduction of DKK-1 at both mRNA and protein levels was observed as early as 2 days post Sonic C25II treatment (FIG. 5B,C). The decrease in DKK-1 expression was sustained and accompanied by decreases in AN markers including PAX6, BF1, OTX1, OTX2, and EMX1 (FIG. 4).

To test whether DKK-1 is functionally involved during hESC differentiation in FP specification, the inventors added recombinant DKK-1 in combination with Sonic C25II and assessed FP marker expression. While treatment with Sonic C25II alone resulted in a decrease of the AN marker BF1 and an upregulation of FOXA2 (FIG. 5D-F), the addition of DKK-1 caused a decrease in FOXA2 message and protein and a more rapid rise in BF1 transcript (FIG. 5D-F). Conversely, addition of DKK-1 antibody to cells in the NSB protocol caused a significant delay and decrease in the levels of BF1 expression. These data indicated that endogenous DKK-1 levels are critical for AN specification. Next, hESCs were differentiated in the presence of both Sonic C25II and DKK-1 neutralizing antibody. Under these conditions, early transient induction of BF1 transcript at day 5 is suppressed and accompanied by an increase in FOXA2 levels (FIGS. 5E and 5G).

The data obtained during the development of the present inventions revealed a critical window for FP specification during neural induction. With the observation that DKK-1 expression can inhibit FOXA2 expression, the following test was designed to demonstrate whether the addition of DKK-1 blocking antibody extends the window of competency for SHH mediated FP induction. DKKK-1 antibody was added at Day 1, Day 5, and Day 9 of differentiation. Exposure to SHH was initiated at the same time points and the expression of FOXA2 was assayed following 9 days of SHH exposure. When Dkk-1 was added along with SHH at Day 1 an increase in FOXA2+ cells was observed. However, when added at Day 5 or Day 9, DKKK-1 antibody FOXA2+ cells were not observed (FIGS. 5H and 5I). These data indicate that high, early endogenous levels of DKK-1 in the NSB protocol initiated AN commitment and suppressed FP competency. Early treatment with SHH repressed DKK-1 mediated AN specification and enabled differentiation towards FP lineage. However, inhibition of DKK-1 at day 5 of later stages did not extend the temporal window for FP induction.

Example X

Bf1 Expression Represses Fp Commitment.

The inventors discovered that SHH addition to stem cell cultures caused FP differentiation at the expense of AN, mediated at least in part, through inhibition of DKK-1. DKK-1 was shown to specify BF1+ neurectoderm BF1 (Mukhopadhyay et al., 2001), and BF1 is expressed in most neural cells upon NSB induction (FIGS. 4 and 5). To test whether expression of the forkhead factor BF1 directly represses FP competency during neural induction, hESCs were transduced with a BF1 shRNA construct (Fasano et al., 2009; Shen et al., 2006) and clonal lines were derived. BF1 is not highly expressed in hESCs and there was no difference in cell morphology or colony size (FIG. 10)).

However, upon neural differentiation of hESCs there was a decrease in BF1 protein expression (FIGS. 5J" and 5K") and an 80% decrease in BF1 transcript (FIG. 10). While BF1 loss of function has been associated with deficits in proliferation and cell cycle progression at the neural precursor stage, BF1 knockdown lines at the hESC stage showed cell cycle kinetics comparable to control vector transduced lines (FIG. 10). BF1 knock-down and control hESCs were then differentiated to FP and subjected to qRT-PCR analysis for a panel of FP markers. After 11 days of differentiation, there was as significant increase in expression of all FP markers in the BF1 shRNA condition (FIG. 5L). Furthermore, immunocytochemical analyses revealed a significant increase in the number of FOXA2+ cells, representing greater than 90% of total cells in the BF1 knockdown hESC line (FIG. 5M).

hESC lines were generated by overexpression of BF1 using a previous described vector (Fasano et al., 2009). These transgenic cells were then cultured under conditions that induced differentiation towards FP lineage. At Day 11, compared to a control GFP expressing clones, there was a reduction of FOXA2+ cells and a decrease in FP marker expression (FIG. 10). These data demonstrated that BF1 expression inhibited the derivation of hESC derived FP.

Example XI

The A/P Axis of the FP were Altered by Caudalizing Agents.

While certain characteristics are shared among all FP cells, such as FOXA2 and Netrin-1 expression, differences have been reported between different regions of the floor plate along the A/P axis (Placzek and Briscoe, 2005). In particular, recent studies have shown that the midbrain FP expresses markers such as CORN (Ono et al., 2007) and NOV (Placzek and Briscoe, 2005).

Additionally, the midbrain FP was shown to be neurogenic giving rise to midbrain DA neurons and expressing markers of DA progenitors such as LMX1B and NGN2 (Joksimovic et al., 2009). In contrast both the hindbrain and spinal cord FP appear to be non-neurogenic. To better understand the A/P identity of the FP cells generated from hESCs qRT-PCR analysis for the midbrain FP markers CORN and NOV was done, as well as analysis of DA progenitor markers LMX1B and EN1. However expression of these markers was not detected. Next gene expression data sets were used to identify differentially regulated transcripts markers that could shed light onto the positional identity of the FP cells.

Elegant studies in the mouse showed that specific enhancer elements direct Shh expression in different regions along the A/P axis of the FP (Jeong et al., 2005). SIX6 were dramatically increased during FP induction compared with NSB control conditions (About 50,000-fold increase in mRNA levels at Day 5 of differentiation; FIG. 9). SIX6 has been shown to bind to the SHH gene at an enhancer region known as SBE2 that directs SHH expression to the most anterior aspect of the ventral brain (Jeong et al., 2008). The inventors contemplated the use of SIX6 as a putative marker of anterior FP identity. Thus SIX6 status of the hESC derived FP was used to mark respecification in response to known caudalizing agents such as FGF8, Wnt-1, and Retinoic Acid. Each of these caudalizing factors was added in combination with SHH and the resulting tissue was assessed for expression of the FP markers FOXA2 and NETRIN-1, the AN marker BF1, and putative anterior FP marker SIX6. FP generation was found not compromised in the presence of caudalizing factors. In fact, the addition of Wnt-1 or RA significantly potentiated FP production based on FOXA2 and Netrin-1 expression. (FIGS. 6A and 6B). Enhanced expression of FP markers in the RA and Wnt-1 group was correlated with a dramatic reduction in BF1 expression further supporting the notion that AN commitment counteracts FP induction (FIG. 6B). Strikingly, in all conditions, there was a significant reduction in SIX6 expression, with the Wnt-1 and RA conditions being the most effective at suppressing anterior FP identity.

Example XII

This example shows exemplary experiments designed to determine whether any of the methods (conditions) used herein would lead to an upregulation of midbrain FP and DA progenitor markers. The inventors discovered that different factors had varied effects on marker expression (FIG. 6B). In particular, exposure to Wnt-1 resulted in a significant increase in the midbrain FP markers CORIN and NOV, as well as increases in the DA progenitor markers LMX1B, EN1, and NGN2. Previous studies showed that Wnt signaling was critical in the neurogenic response of the midbrain FP (Joksimovic et al., 2008).

As mentioned above, studies had identified different enhancers that directed SHH expression to different A/P region along ventral axis (Jeong et al., 2008). To further demonstrate that the addition of caudilizing factors re-specifies A/P identity of the resulting FP tissue, hESCs derived FP were generated in the presence or absence of Wnt-1 or FGF8, and transfected the resulting tissue with two SHH enhancer constructs driving LacZ expression in different A/P domains of the FP. The SBE1 construct directs SHH expression to the midbrain region of the floor plate while the SBE2 enhancer directs SHH expression to the most anterior region of the FP where Six6 has been shown to bind. In the absence of caudalizing factors (SHH C25II alone), LacZ expression was observed herein following transfection with the SBE2 but not the SBE1 enhancer supporting the hypothesis that hESC derived FP is anterior by default (FIG. 6C). In contrast SBE2 activity was abolished upon treatment with Wnt1 or FGF8 while SBE1 activity was induced under these conditions. These data indicated that FGF8 or Wnt1 treatment induces a shift in FP identity towards a more caudal, midbrain-like identity (FIG. 6C).

In conclusion, our data demonstrated that upon neural differentiation hESCs default towards an fate by upregulating DKK-1 and subsequently BF1, and that AN commitment actively represses FP competency in hESC progeny. However, an early high level of SHH reduces DKK-1 levels enabling FP induction at the expense of AN while loss-of-function of DKK-1 or BF1 increases FP production. Human ESC derived FP is anterior by default but were posteriorized in response to caudalizing factors. This is summarized in FIG. 20E.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in cellular biology, neurobiology, cancer cell biology, molecular biology, biochemistry, chemistry, organic synthesis, or related fields are intended to be within the scope of the following claims.

The invention claimed is:

1. A kit, comprising:
a first inhibitor of Small Mothers Against Decapentaplegic (SMAD) protein signaling ("first SMAD inhibitor") that comprises an inhibitor of bone morphogenetic protein (BMP) signaling,
a second inhibitor of Small Mothers Against Decapentaplegic (SMAD) protein signaling ("second SMAD inhibitor") that comprises an inhibitor of TGFβ/Activin-Nodal signaling, and
an activator of Sonic Hedgehog (SHH) signaling that comprises a SHH protein.

2. The kit of claim 1, further comprising instructions for inducing differentiation of pluripotent stem cells.

3. The kit of claim 2, wherein said instructions comprise exposing a plurality of pluripotent stem cells to said first and second SMAD inhibitors to produce a cell population comprising at least about 10% differentiated cells expressing CDX2, wherein said exposing to said first SMAD inhibitor is discontinued after about one day from the initial exposure of said pluripotent stem cells to said first SMAD inhibitor.

4. The kit of claim 3, wherein said differentiated cells are trophectodermal precursors.

5. The kit of claim 2, wherein said instructions comprise exposing a plurality of pluripotent stem cells to the first and second SMAD inhibitors to produce a cell population comprising at least about 10% differentiated cells expressing SIX1, wherein said exposing to said first SMAD inhibitor is discontinued after about two days or about three days from the initial exposure of said pluripotent stem cells to said first SMAD inhibitor.

6. The kit of claim 5, wherein said differentiated cells are placodal precursors.

7. The kit of claim 2, wherein said instructions comprise exposing a plurality of pluripotent stem cells to said first and second SMAD inhibitors to produce a cell population comprising at least about 10% differentiated cells expressing paired box homeotic gene-6 (PAX6).

8. The kit of claim 7, wherein said exposing comprises exposing said pluripotent stem cells to said first and second SMAD inhibitors for at least about 10 days.

9. The kit of claim 8, wherein said exposing comprises exposing said pluripotent stem cells to said first and second SMAD inhibitors for about 10days or about 11 days.

10. The kit of claim 1, wherein said SHH protein comprises a modified recombinant protein at least about 95% identical to a mouse Sonic Hedgehog N-terminal fragment.

11. The kit of claim 2, wherein said instructions comprise exposing a plurality of pluripotent stem cells to said first and second SMAD inhibitors and exposing said cells to the activator of SHH signaling to produce a cell population comprising at least about 10% differentiated cells expressing one or more marker selected from the group consisting of forkhead box protein A2 (FOXA2), SSH, Netrin-1, and F-Spondin.

12. The kit of claim 11, wherein said instructions comprise initially exposing said cells to said activator of SHH signaling within about 60 hours from the initial exposure of the pluripotent stem cells to said first and second SMAD inhibitors.

13. The kit of claim 11, wherein said differentiated cells are neural floor plate cells.

14. The kit of claim 13, wherein said differentiated cells are anterior floor plate cells.

15. The kit of claim 11, wherein said instructions comprise initially exposing said cells to said activator of SHH signaling no later than about 7 days from the initial exposure of said pluripotent stem cells to said first SMAD inhibitor.

16. The kit of claim 15, wherein said instructions comprise initially exposing said cells to said activator of SHH signaling about one day from the initial exposure of said pluripotent stem cells to said first SMAD inhibitor.

17. The kit of claim 1, further comprising one or more caudalizing factor.

18. The kit of claim 17, wherein said one or more caudalizing factor is selected from the group consisting of wingless-type MMTV integration site family member 1 (Wnt-I), Fibroblast Growth Factor 8 (FGF8) and Retinoic Acid (RA).

19. The kit of claim 17, further comprising instructions for inducing differentiation of pluripotent stem cells, wherein said instructions comprise exposing a plurality of pluripotent stem cells to said first and second SMAD inhibitors, and exposing said cells to said activator of SHH signaling and the one or more caudalizing factor to produce a cell population comprising at least about 10% differentiated cells expressing one or more marker selected from the group consisting of serine peptidase (CORIN), LIM homeobox transcription factor 1, beta (LMX1B), EN1, neurogenin 2 (NGN2), and nephroblastoma overexpressed gene (NOV).

20. The kit of claim 19, wherein said differentiated cells are posterior floor plate cells, dopaminergic progenitors, or a combination thereof.

21. The kit of claim 19, wherein said differentiated cells are midbrain floor plate cells.

22. The kit of claim 17, further comprising instructions for inducing differentiation of pluripotent stem cells, wherein said instructions comprise exposing a plurality of pluripotent stem cells to said first and second SMAD inhibitors, and exposing said cells to said activator of SHH signaling and said one or more caudalizing factor to produce a cell population comprising at least about 10% differentiated cells expressing Tyrosine hydroxylase (TH).

23. The kit of claim 22, wherein said differentiated cells are dopaminergic cells.

24. The kit of claim 22, further comprising brain-derived neurotrophic factor (BDNF), ascorbic acid, or a combination thereof, and wherein said caudalizing factor is FGF8.

25. The kit of claim 17, further comprising instructions for inducing differentiation of pluripotent stem cells, wherein said instructions comprise exposing a plurality of pluripotent stem cells to said first and second SMAD inhibitors, and exposing said cells to said activator of SHE signaling and said one or more caudalizing factor to produce a cell population comprising at least about 10% differentiated cells expressing one or more marker selected from the group consisting of ISL1 and HB9.

26. The kit of claim 25, wherein said differentiated cells are motor neuronal cells.

27. The kit of claim 25, further comprising BDNF, ascorbic acid, or a combination thereof, and wherein said caudalizing factor is RA.

28. The kit of claim 1, wherein said inhibitor of TGFβ/Activin-Nodal signaling comprises 4-[4-(1,3-benzodioxol-5-yl)-5-(2-pyridinyl)-1H-imidazol-2-yl] benzamide (SB431542).

29. The kit of claim 1, wherein said inhibitor of BMP signaling is selected from the group consisting of Noggin, a disulfide-linked homodimer of Noggin, Dorsomorphin, LDN-193189, and mixtures thereof.

30. The kit of claim 29, wherein said inhibitor of BMP signaling is LDN-193189.

31. The kit of claim 1, wherein said SHH protein is selected from the group consisting of Sonic hedgehog (SHH) and Sonic C25II.

* * * * *

SEQUENCE LISTING

<160> NUMBER OF SEQ ID NOS: 1

<210> SEQ ID NO 1
<211> LENGTH: 240
<212> TYPE: PRT
<213> ORGANISM: Mus musculus

<400> SEQUENCE: 1

```
Met Glu Arg Cys Pro Ser Leu Gly Val Thr Leu Tyr Ala Leu Val Val
1               5                   10                  15

Val Leu Gly Leu Arg Ala Ala Pro Ala Gly Gly Gln His Tyr Leu His
            20                  25                  30

Ile Arg Pro Ala Pro Ser Asp Asn Leu Pro Leu Val Asp Phe Thr Leu
        35                  40                  45

Ile Glu His Pro Asp Pro Ile Phe Asp Pro Lys Glu Lys Asp Leu Asn
    50                  55                  60

Glu Thr Leu Leu Arg Ser Leu Leu Gly Gly His Tyr Asp Pro Gly Phe
65                  70                  75                  80

Met Ala Thr Ser Pro Pro Glu Asp Arg Pro Gly Gly Gly Gly Gly Pro
                85                  90                  95

Ala Gly Gly Ala Glu Asp Leu Ala Glu Leu Phe Thr Asp Gln Leu Leu
            100                 105                 110

Arg Gln Arg Pro Ser Gly Ala Met Pro Ser Glu Ile Lys Gly Leu Glu
        115                 120                 125

Phe Ser Glu Gly Leu Ala Gln Gly Lys Lys Gln Arg Leu Ser Lys Lys
    130                 135                 140

Leu Arg Arg Lys Leu Gln Met Trp Leu Trp Ser Gln Thr Phe Cys Pro
145                 150                 155                 160

Val Leu Tyr Ala Trp Asn Asp Phe Thr Leu Gly Ser Arg Phe Trp Pro
                165                 170                 175

Arg Tyr Val Lys Val Gly Ser Cys Phe Ser Lys Arg Ser Cys Ser Val
            180                 185                 190

Pro Glu Gly Met Val Cys Lys Pro Ser Lys Ser Val His Leu Thr Val
        195                 200                 205

Leu Arg Trp Arg Cys Gln Arg Arg Gly Gly Gln Arg Cys Gly Trp Ile
    210                 215                 220

Pro Ile Gln Tyr Phe Thr Pro Ile Ile Ser Glu Cys Lys Cys Ser Cys
225                 230                 235                 240
```